United States Patent
Rau et al.

(10) Patent No.: US 11,298,427 B2
(45) Date of Patent: Apr. 12, 2022

(54) PRODRUGS COMPRISING A PYROGLUTAMATE LINKER

(71) Applicants: Ascendis Pharma A/S, Hellerup (DK); Ascendis Pharma Inc., Palo Alto, CA (US)

(72) Inventors: Harald Rau, Dossenheim (DE); Nicola Bisek, Heidelberg (DE); Samuel Weisbrod, Heidelberg (DE)

(73) Assignees: Ascendis Pharma A/S, Hellerup (DK); Ascendis Pharma Inc., Palo Alto, CA (US)

( * ) Notice: Subject to any disclaimer, the term of this patent is extended or adjusted under 35 U.S.C. 154(b) by 906 days.

(21) Appl. No.: 15/577,606

(22) PCT Filed: May 25, 2016

(86) PCT No.: PCT/US2016/034105
§ 371 (c)(1),
(2) Date: Nov. 28, 2017

(87) PCT Pub. No.: WO2016/196124
PCT Pub. Date: Dec. 8, 2016

(65) Prior Publication Data
US 2019/0216940 A1    Jul. 18, 2019

(30) Foreign Application Priority Data

May 29, 2015  (EP) .................................. 15169843

(51) Int. Cl.
*A61K 47/64*  (2017.01)
*A61K 47/60*  (2017.01)
*A61K 47/54*  (2017.01)

(52) U.S. Cl.
CPC ............ *A61K 47/645* (2017.08); *A61K 47/54* (2017.08); *A61K 47/60* (2017.08)

(58) Field of Classification Search
CPC ....... A61K 47/645; A61K 47/54; A61K 47/60
See application file for complete search history.

(56) References Cited

U.S. PATENT DOCUMENTS

| | | | | |
|---|---|---|---|---|
| 2011/0053848 A1* | 3/2011 | Cleemann | ............... | A61P 43/00 514/11.3 |
| 2012/0191039 A1* | 7/2012 | Rau | ........................ | A61P 25/24 604/92 |
| 2013/0072491 A1 | 3/2013 | Yasuda et al. | | |
| 2014/0323402 A1* | 10/2014 | Hersel | .................... | A61K 47/64 514/11.2 |

FOREIGN PATENT DOCUMENTS

| | | | | |
|---|---|---|---|---|
| WO | WO 2005/099768 | 10/2005 | | |
| WO | WO 2006/003014 | 1/2006 | | |
| WO | WO-2006003014 A2 * | 1/2006 | ............. | A61P 37/00 |
| WO | WO 2006/136586 | 12/2006 | | |
| WO | WO 2009/095479 | 8/2009 | | |
| WO | WO 2011/012715 | 2/2011 | | |
| WO | WO 2011/012722 | 2/2011 | | |
| WO | WO 2011/089214 | 7/2011 | | |
| WO | WO 2011/089215 | 7/2011 | | |
| WO | WO 2011/089216 | 7/2011 | | |
| WO | WO 2013/024049 | 2/2013 | | |
| WO | WO 2014/056926 | 4/2014 | | |
| WO | WO 2015/006740 | 1/2015 | | |

OTHER PUBLICATIONS

"Bioisosteric Replacements," Cambridge MedChem Consulting, <https://www.cambridgemedchemconsulting.com/resources/bioisoteres/>, published Jan. 13, 2013, p. 1-5.*
Goldstein, Alex S. et al., "Testosterone delivery using Glutamide-based Complex High Axial Ratio Microstructures" Bioorganic & Medicinal Chemistry, GB, Jun. 11, 2001, 2819-2825, 9(11) XP085061058.
International Search Report issued in corresponding PCT Application No. PCT/US2016/034105 dated Oct. 17, 2016, 4 pages.
Markus Gude, et al., *An Accurate Method for the Quantitation of Fmoc-Derivatized Solid Phase Supports*, 9(4) Letters in Peptide Science 203-206 (2002).
Pubchem, Bioassay record for AID 651631 Deposit Date: Oct. 10, 2012. Retrieved from the Internet: https://pubchem.ncbi.nlm.nih.gov/bioassay/651631.Entire document.

* cited by examiner

*Primary Examiner* — Monica A Shin
(74) *Attorney, Agent, or Firm* — Haug Partners LLP

(57) ABSTRACT

The present invention relates to novel prodrugs of primary or secondary amine-comprising biologically active moieties and pharmaceutically acceptable salts thereof, prodrug reagents, pharmaceutical compositions comprising said prodrugs and the use of prodrugs.

16 Claims, No Drawings

PRODRUGS COMPRISING A PYROGLUTAMATE LINKER

The present application claims priority from PCT/US2016/34105 filed on May 25, 2016, which claims priority from European Patent Application No. EP 15169843.8 filed on May 29, 2015, the disclosures of which are incorporated herein by reference in their entirety.

The present invention relates to novel prodrugs of primary or secondary amine-comprising biologically active moieties and pharmaceutically acceptable salts thereof, prodrug reagents, pharmaceutical compositions comprising said prodrugs and the use of said prodrugs.

To improve physicochemical or pharmacokinetic properties of a drug in vivo such drug can be conjugated to a carrier. Typically, carriers in drug delivery are either used in non-covalent complexation of drug and carrier, or by covalent attachment of a carrier reagent to one of the drug's functional groups.

However, the non-covalent approach requires a highly efficient drug-carrier complexation to prevent uncontrolled, burst-type release of the drug due to disintegration of the drug-carrier complex after administration. Restraining the diffusion of an unbound, water soluble drug molecule requires strong van der Waals contacts, frequently mediated through hydrophobic moieties and charged moieties for electrostatic binding. Many conformationally sensitive drugs, such as proteins or peptides, are rendered dysfunctional during the complexation process and/or during subsequent storage of the non-covalently bound drug.

Alternatively, a drug may be covalently conjugated to a carrier via a stable linker or a reversible prodrug linker moiety from which the drug is released. If the drug is stably connected to the carrier, such a conjugate needs to exhibit sufficient residual activity to have a pharmaceutical effect, thus the conjugate is constantly in an active form.

If the drug is conjugated to the carrier through a reversible prodrug linker, such conjugates are referred to as carrier-linked prodrugs. The advantage of this approach is that no residual activity of the conjugate is needed, because the drug exhibits its pharmacological effect upon release from the conjugate. A carrier-linked prodrug may exhibit no or little drug activity, i.e. the carrier-linked prodrug is pharmacologically inactive. This approach is applied to various classes of molecules, from so-called small molecules, through natural products up to large proteins.

The biologically active moiety of such a carrier-linked prodrug can be released by enzymatic or non-enzymatic cleavage of the linkage between the carrier and the biologically active moiety, or by a sequential combination of both. However, enzyme-dependence is usually less preferred, because enzyme levels may vary significantly between patients what makes the correct dosing difficult.

Various non-enzymatically cleavable reversible prodrug linkers are known in the art, such as for example those disclosed in WO2005/099768 A2, WO2006/136586 A2, WO2009/095479 A2, WO2011/012722 A1, WO2011/089214 A1, WO2011/089216 A1 and WO2011/089215 A1.

Given the multitude of different drugs, it is desirable to have a large portfolio of reversible prodrug linkers available to identify the one that is most suitable. Not only are different release half-lives needed, but not every linker is suitable for every type of conjugation chemistry. Especially when sensitive drugs, such as proteins, are to be converted into prodrugs the conjugation conditions (including the cleavage of potentially necessary protecting groups) need to be sufficiently mild to ensure integrity of the biologically active moiety.

It is therefore an object of the present invention to at least partially overcome the above-mentioned disadvantage.

This object is achieved with a prodrug or a pharmaceutically acceptable salt thereof comprising a conjugate D-L, wherein
-D is a primary or secondary amine-comprising biologically active moiety; and
-L comprises a linker moiety -L$^1$ represented by formula (I)

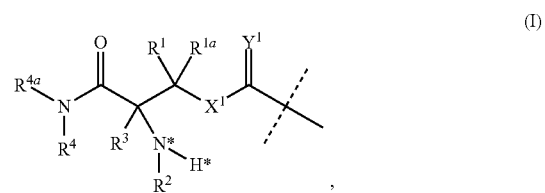

wherein
the dashed line indicates attachment to the primary or secondary amine of the biologically active moiety;
—X$^1$ is selected from the group consisting of —CR$^5$R$^{5a}$—, —O—, —NR$^5$— and —S—;
—R$^1$, —R$^{1a}$, —R$^2$, —R$^3$, —R$^4$, —R$^{4a}$, —R$^5$, and —R$^{5a}$ are independently of other selected from —H, C$_{1-6}$ alkyl, C$_{2-6}$ alkenyl, and C$_{2-6}$ alkynyl; wherein C$_{1-6}$ alkyl, C$_{2-6}$ alkenyl, and C$_{2-6}$ alkenyl are optionally substituted with one or more R$^6$, which are the same or different; and wherein C$_{1-6}$ alkyl, C$_{2-6}$ alkenyl, and C$_{2-6}$ alkynyl are optionally interrupted by one or more groups selected from the group consisting of -T-, —C(O)O—, —O—, —C(O)—, —C(O)N(R$^7$)—, —S(O)$_2$N(R$^7$)—, —S(O)N(R$^7$)—, —S(O)$_2$—, —S(O)—, —N(R$^7$)S(O)$_2$N(R$^{7a}$)—, —S—, —N(R$^7$)—, —OC(OR$^7$)(R$^{7a}$)—, —N(R$^7$)C(O)N(R$^{7a}$)—, and —OC(O)N(R$^7$)—; provided that the nitrogen marked with the asterisk is connected to —R$^2$ through an SP$^3$-hybridized carbon atom;
each T is independently of each other selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T is independently optionally substituted with one or more R$^6$, which are the same or different;
each —R$^6$, —R$^7$, —R$^{7a}$ is independently selected from the group consisting of —H, and C$_{1-6}$ alkyl; wherein C$_{1-6}$ alkyl is optionally substituted with one or more halogen, which are the same or different;
=Y' is selected from =O and =NR$^5$;
Optionally, one or more of the pairs —R$^1$/—R$^{1a}$, —R$^2$/—R$^3$, —R$^5$/—R$^{5a}$ and —R$^4$/—R$^{4a}$ are joined together with the atom to which they are attached to form a C$_{3-10}$ cycloalkyl, 3- to 10-membered heterocyclyl or a 8- to 11-membered heterobicyclyl;
Optionally, one or more of the pairs —R$^1$/—R$^2$, —R$^1$/—R$^3$, —R$^1$/—R$^5$, —R$^1$/—R$^{5a}$, —R$^{1a}$/—R$^2$, —R$^{1a}$/—R$^3$, —R$^{1a}$/—R$^5$, —R$^{1a}$/—R$^{5a}$, —R$^2$/—R$^5$, —R$^2$/—R$^{5a}$, —R$^3$/—R$^5$, —R$^3$/—R$^{5a}$ are joined together with the atoms to which they are attached to form a ring -A-;

-A- is selected from the group consisting of phenyl; naphthyl; indenyl; indanyl; tetralinyl; $C_{3-10}$ cycloalkyl; 3- to 10-membered heterocyclyl; and 8- to 11-membered heterobicyclyl;

wherein $-L^1$ is substituted with one to five moieties $-L^2-Z$, preferably $-L^1$ is substituted with one moiety $-L^2-Z$, and is optionally further substituted, provided that the hydrogen marked with the asterisk in formula (I) is not replaced by a substituent; wherein $-L^2$ is a single chemical bond or a spacer moiety; and $-Z$ is a carrier moiety.

It was surprisingly found that the reversible prodrug linker moiety $-L^1$- of formula (I) has advantageous properties, such as an increased stability of the activated corresponding reagent under conditions particularly beneficial for the conjugation of proteins.

Within the present invention the terms are used with the meaning as follows:

The term "drug" as used herein refers to a substance used in the treatment, cure, prevention, or diagnosis of a disease or used to otherwise enhance physical or mental well-being. If a drug is conjugated to another moiety, the part of the resulting product that originated from the drug is referred to as "biologically active moiety".

It is understood that the term "primary or secondary amine-comprising drug" refers to a drug having at least one primary or secondary amine functional group, respectively, which primary or secondary amine-comprising drug may optionally have one or more further functional group(s) including one or more additional primary and/or secondary amine functional group(s). If such primary or secondary amine-comprising drug is conjugated to, for example, a moiety $-L^1$, it is referred to as "primary or secondary amine-comprising biologically active moiety", even though it is understood that said primary or secondary amine functional group became part of the amide bond connecting both moieties.

As used herein the term "prodrug" or "carrier-linked prodrug" refers to a biologically active moiety reversibly and covalently connected to a specialized protective group through a reversible prodrug linker moiety comprising a reversible linkage with the biologically active moiety to alter or to eliminate undesirable properties in the parent molecule. This also includes the enhancement of desirable properties in the drug and the suppression of undesirable properties. The specialized non-toxic protective group is referred to as "carrier". A prodrug releases it reversibly and covalently bound biologically active moiety in the form of its corresponding drug.

A "biodegradable linkage" or a "reversible linkage" is a linkage that is hydrolytically degradable, i.e. cleavable, in the absence of enzymes under physiological conditions (aqueous buffer at pH 7.4, 37° C.) with a half-life ranging from one hour to twelve months.

In contrast, a "permanent linkage" is not hydrolytically degradable, i.e. cleavable, in the absence of enzymes under physiological conditions (aqueous buffer at pH 7.4, 37° C.) with a half-life of less than twelve months.

As used herein, the term "traceless prodrug linker" means a reversible prodrug linker which upon cleavage releases the drug in its free form. As used herein, the term "free form" of a drug means the drug in its unmodified, pharmacologically active form. The reversible prodrug linker of the present invention, $L^1$, is a traceless prodrug linker.

As used herein, the term "excipient" refers to a diluent, adjuvant, or vehicle with which the therapeutic is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, mannitol, trehalose, gelatin, malt, rice, flour, chalk, silica gel, sodium stearate, glycerol monostearate, talc, sodium chloride, dried skim milk, glycerol, propylene, glycol, water, ethanol and the like. The pharmaceutical composition, if desired, can also contain minor amounts of wetting or emulsifying agents, pH buffering agents, like, for example, acetate, succinate, tris, carbonate, phosphate, HEPES (4-(2-hydroxyethyl)-1-piperazineethanesulfonic acid), MES (2-(N-morpholino)ethanesulfonic acid), or can contain detergents, like Tween, poloxamers, poloxamines, CHAPS, Igepal, or amino acids like, for example, glycine, lysine, or histidine. These pharmaceutical compositions can take the form of solutions, suspensions, emulsions, tablets, pills, capsules, powders, sustained-release formulations and the like. The pharmaceutical composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Such compositions will contain a therapeutically effective amount of the drug or biologically active moiety, together with a suitable amount of excipient so as to provide the form for proper administration to the patient. The formulation should suit the mode of administration.

As used herein, the term "hydrogel" means a hydrophilic or amphiphilic polymeric network composed of homopolymers or copolymers, which is insoluble due to the presence of covalent chemical crosslinks. The crosslinks provide the network structure and physical integrity. Hydrogels exhibit a thermodynamic compatibility with water which allows them to swell in aqueous media.

As used herein, the term "reagent" means a chemical compound which comprises at least one functional group for reaction with the functional group of another chemical compound or drug. It is understood that a drug comprising a functional group (such as a primary or secondary amine functional group) is also a reagent.

As used herein, the term "backbone reagent" means a reagent, which is suitable as a starting material for forming hydrogels. As used herein, a backbone reagent preferably does not comprise biodegradable linkages. A backbone reagent may comprise a "branching core" which term refers to an atom or moiety to which more than one other moiety is attached.

As used herein, the term "crosslinker reagent" means a linear or branched reagent, which is suitable as a starting material for crosslinking backbone reagents. Preferably, the crosslinker reagent is a linear chemical compound. A crosslinker reagent preferably comprises at least one biodegradable linkage.

As used herein, the term "moiety" means a part of a molecule, which lacks one or more atom(s) compared to the corresponding reagent. If, for example, a reagent of the formula "H—X—H" reacts with another reagent and becomes part of the reaction product, the corresponding moiety of the reaction product has the structure "H—X—"

or "—X—", whereas each "—" indicates attachment to another moiety. Accordingly, a biologically active moiety is released from a prodrug as a drug.

Accordingly, the phrase "in bound form" is used to refer to the corresponding moiety of a reagent, i.e. "lysine in bound form" refers to a lysine moiety which lacks one or more atom(s) of the lysine reagent and is part of a molecule.

It is understood that if the sequence or chemical structure of a group of atoms is provided which group of atoms is attached to two moieties or is interrupting a moiety, said sequence or chemical structure can be attached to the two moieties in either orientation, unless explicitly stated otherwise. For example, a moiety "—C(O)N(R)—" can be attached to two moieties or interrupting a moiety either as "—C(O)N(R)—" or as "—N(R)C(O)—". Similarly, a moiety

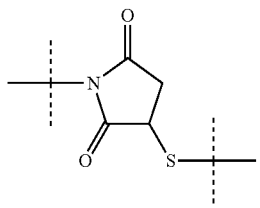

can be attached to two moieties or can interrupt a moiety either as

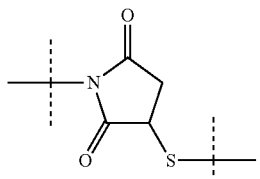

or as

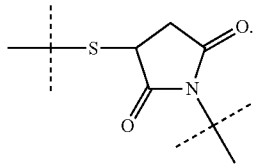

As used herein, the term "functional group" means a group of atoms which can react with other groups of atoms. Functional groups include but are not limited to the following groups: carboxylic acid (—(C=O)OH), primary or secondary amine (—NH$_2$, —NH—), maleimide, thiol (—SH), sulfonic acid (—(O=S=O)OH), carbonate, carbamate (—O(C=O)N<), hydroxyl (—OH), aldehyde (—(C=O)H), ketone (—(C=O)—), hydrazine (>N—N<), isocyanate, isothiocyanate, phosphoric acid (—O(P=O)OHOH), phosphonic acid (—O(P=O)OHH), haloacetyl, alkyl halide, acryloyl, aryl fluoride, hydroxylamine, disulfide, vinyl sulfone, vinyl ketone, diazoalkane, oxirane, and aziridine.

As used herein, the term "activated functional group" means a functional group, which is connected to an activating group, i.e. a functional group was reacted with an activating reagent. Preferred activated functional groups include but are not limited to activated ester groups, activated carbamate groups, activated carbonate groups and activated thiocarbonate groups. Preferred activating groups are selected from formulas (f-i) to (f-vii):

 (f-i)

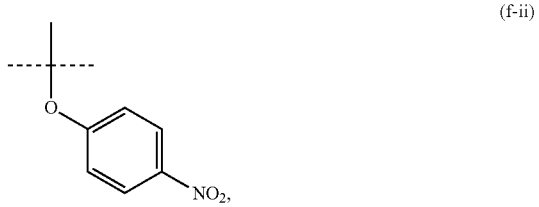 (f-ii)

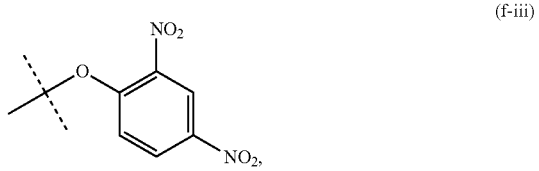 (f-iii)

 (f-iv)

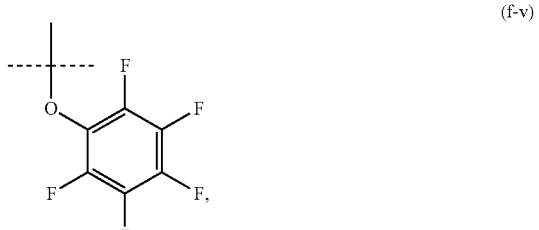 (f-v)

 (f-vi)

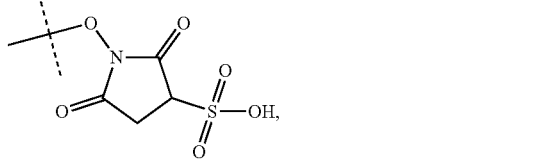 (f-vii)

wherein
the dashed lines indicate attachment to the rest of the molecule;
b is 1, 2, 3 or 4; and
$X^H$ is Cl, Br, I, or F.

Accordingly, a preferred activated ester has the formula
—(C=O)—$X^F$,
wherein
$X^F$ is selected from formula (f-i), (f-ii), (f-iii), (f-iv), (f-v), (f-vi) and (f-vii).

Accordingly, a preferred activated carbamate has the formula
—N—(C=O)—$X^F$, wherein $X^F$ is selected from formula (f-i), (f-ii), (f-iii), (f-iv), (f-v), (f-vi) and (f-vii).

Accordingly, a preferred activated carbonate has the formula

—O—(C=O)—$X^F$, wherein $X^F$ is selected from formula (f-i), (f-ii), (f-iii), (f-iv), (f-v), (f-vi) and (f-vii).

Accordingly, a preferred activated thioester has the formula

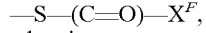
—S—(C=O)—$X^F$, wherein $X^F$ is selected from formula (f-i), (f-ii), (f-iii), (f-iv), (f-v), (f-vi) and (f-vii).

As used herein, the term "protecting group" means a moiety which is reversibly connected to a functional group to render it incapable of reacting with, for example, another functional group. Suitable alcohol (—OH) protecting groups are, for example, acetyl, benzoyl, benzyl, β-methoxyethoxymethyl ether, dimethoxytrityl, methoxymethyl ether, methoxytrityl, p-methoxybenzyl ether, methylthiomethyl ether, pivaloyl, tetrahydropyranyl, trityl, trimethylsilyl, tert-butyldimethylsilyl, tri-iso-propylsilyloxymethyl, triisopropylsilyl ether, methyl ether, and ethoxyethyl ether. Suitable amine protecting groups are, for example, ortho nitrobenzosulfonyl, carbobenzyloxy, p-methoxybenzyl carbonyl, tert-butyloxycarbonyl, 9-fluorenylmethyloxyarbonyl, acetyl, benzoyl, benzyl, carbamate, p-methoxybenzyl, 3,4-dimethoxybenzyl, p-methoxyphenyl, and tosyl. Suitable carbonyl protecting groups are, for example, acetals and ketals, acylals and dithianes. Suitable carboxylic acid protecting groups are, for example, methyl esters, benzyl esters, tert-butyl esters, 2,6-dimethylphenol, 2,6-diisopropylphenol, 2,6-di-tert-butylphenol, silyl esters, orthoesters, and oxazoline. Suitable phosphate protecting groups are, for example, 2-cyanoethyl and methyl.

In case the compounds according to formula (I) or (I') contain one or more acidic or basic groups, the invention also comprises their corresponding pharmaceutically or toxicologically acceptable salts, in particular their pharmaceutically utilizable salts. Thus, the compounds of the formula (I) or (I') which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) or (I') which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. For the person skilled in the art further methods are known for converting the basic group into a cation like the alkylation of an amine group resulting in a positively-charge ammonium group and an appropriate counterion of the salt. If the compounds of the formula (I) or (I') simultaneously contain acidic and basic groups in the molecule, the invention also includes, in addition to the salt forms mentioned, inner salts or betaines (zwitterions). The respective salts according to the formula (I) or (I') can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) or (I') which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means approved by a regulatory agency such as the EMEA (Europe) and/or the FDA (US) and/or any other national regulatory agency for use in animals, preferably in humans.

As used herein the term "small molecule biologically active moiety" refers to an organic biologically active moiety having a molecular weight of less than 1000 Da, such as less than 900 Da or less than 800 Da.

As used herein, the term "oligonucleotide" refers to double- or single-stranded RNA and DNA with preferably 2 to 1000 nucleotides and any modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited, to 2'-position sugar modifications, 5-position pyrimidine modifications, 8-position purine modifications, modifications at exocyclic amines, substitution of 4-thiouridines, substitution of 5-bromo or 5-iodo-uracil; backbone modifications, methylations, unusual base-pairing combinations such as the isobases isocytidine and isoguanidine and the like. Modifications can also include 3' and 5' modifications such as capping and change of stereochemistry. The term also includes aptamers.

The term "peptide nucleic acids" refers to organic polymers having a peptidic backbone, i.e. a backbone in which the monomers are connected to each other through peptide linkages, to which nucleobases, preferably adenine, cytosine, guanine, thymine and uracil, are attached. A preferred backbone comprises N-(2-aminoethyl)-glycine.

The term "peptide" as used herein refers to a chain of at least 2 and up to and including 50 amino acid monomer moieties linked by peptide (amide) linkages. The term "peptide" also includes peptidomimetics, such as D-peptides, peptoids or beta-peptides, and covers such peptidomimetic chains with up to and including 50 monomer moieties.

As used herein, the term "protein" refers to a chain of more than 50 amino acid monomer moieties linked by peptide linkages, in which preferably no more than 12000 amino acid monomers are linked by peptide linkages, such as no more than 10000 amino acid monomer moieties, no more than 8000 amino acid monomer moieties, no more than 5000 amino acid monomer moieties or no more than 2000 amino acid monomer moieties.

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. It is understood that a polymer may also comprise one or more other chemical group(s) and/or moiety/moieties, such as, for example, one or more functional group(s). Preferably, a soluble polymer has a molecular weight of at least 0.5 kDa, e.g. a molecular weight of at least 1 kDa, a molecular weight of at least 2 kDa, a molecular weight of at least 3 kDa or a molecular weight of at least 5 kDa. If the polymer is soluble, it preferable has a molecular weight of at most 1000 kDa, such as at most 750 kDa, such as at most 500 kDa, such as at most 300 kDa, such as at most 200 kDa, such as at most 100 kDa. It is understood that for insoluble polymers, such as hydrogels, no meaningful molecular weight ranges can be provided.

As used herein, the term "polymeric" means a reagent or a moiety comprising one or more polymer(s).

The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers. As used herein, the term "number average molecular weight" means the ordinary arithmetic means of the molecular weights of the individual polymers.

As used herein, the term "polymerization" or "polymerizing" means the process of reacting monomer or macromonomer reagents in a chemical reaction to form polymer chains or networks, including but not limited to hydrogels.

As used herein, the term "macromonomer" means a molecule that was obtained from the polymerization of monomer reagents.

As used herein, the term "condensation polymerization" or "condensation reaction" means a chemical reaction, in which the functional groups of two reagents react to form one single molecule, i.e. the reaction product, and a low molecular weight molecule, for example water, is released.

As used herein, the term "suspension polymerization" means a heterogeneous and/or biphasic polymerization reaction, wherein the monomer reagents are dissolved in a first solvent, forming the disperse phase which is emulsified in a second solvent, forming the continuous phase. In the present invention, the monomer reagents are the at least one backbone reagent and the at least one crosslinker reagent. Both the first solvent and the monomer reagents are not soluble in the second solvent. Such emulsion is formed by stirring, shaking, exposure to ultrasound or Microsieve™ emulsification, more preferably by stirring or Microsieve™ emulsification and more preferably by stirring. This emulsion is stabilized by an appropriate emulsifier. The polymerization is initiated by addition of a base as initiator which is soluble in the first solvent. A suitable commonly known base suitable as initiator may be a tertiary base, such as tetramethylethylenediamine (TMEDA).

As used herein, the term "polyamine" means a reagent or moiety comprising more than one amine (—NH— and/or —NH$_2$), e.g. from 2 to 64 amines, from 4 to 48 amines, from 6 to 32 amines, from 8 to 24 amines, or from 10 to 16 amines. Particularly preferred polyamines comprise from 2 to 32 amines.

As used herein, the term "hydrogel" means a hydrophilic or amphiphilic polymeric network composed of homopolymers or copolymers, which is insoluble due to the presence of covalent chemical crosslinks. The crosslinks provide the network structure and physical integrity.

As used herein, the term "PEG-based comprising at least X % PEG" in relation to a moiety or reagent means that said moiety or reagent comprises at least X % (w/w) ethylene glycol units (—CH$_2$CH$_2$O—), wherein the ethylene glycol units may be arranged blockwise, alternating or may be randomly distributed within the moiety or reagent and preferably all ethylene glycol units of said moiety or reagent are present in one block; the remaining weight percentage of the PEG-based moiety or reagent are other moieties preferably selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

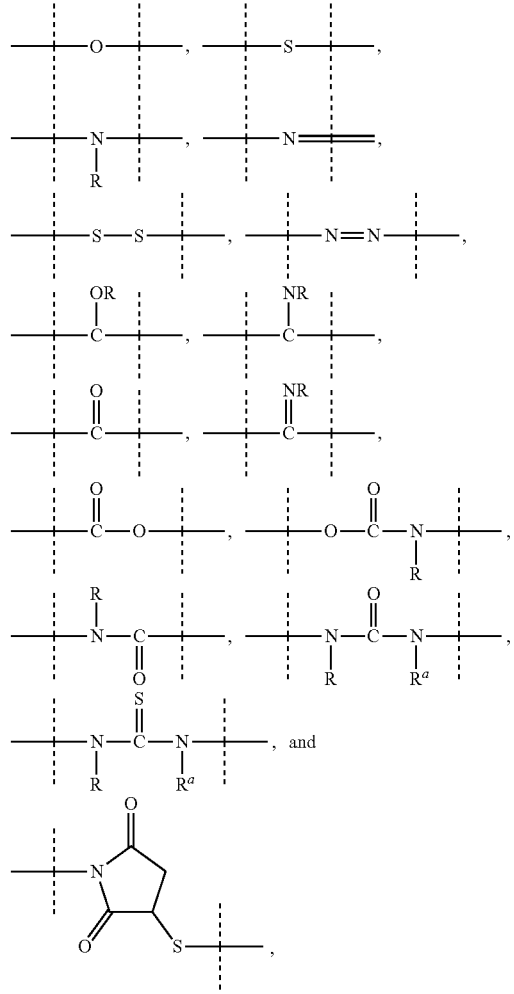

wherein
dashed lines indicate attachment to the remainder of the moiety or reagent, and R and $R^a$ are independently of each other selected from the group consisting of H, methyl, ethyl, propyl, butyl, pentyl and hexyl.

The term "hyaluronic acid-based comprising at least X % hyaluronic acid" is used accordingly.

The term "substituted" as used herein means that one or more —H atom(s) of a molecule or moiety are replaced by a different atom or a group of atoms, which are referred to as "substituent". Preferably, no more than 6 —H atoms of a molecule or moiety are replaced by a substituent, such as 5 —H atoms of a molecule or moiety are replaced by a substituent, 4 —H atoms of a molecule or moiety are replaced by a substituent, 3 —H atoms of a molecule or moiety are replaced by a substituent, 2 —H atoms of a molecule or moiety are replaced by a substituent or 1 —H atom of a molecule or moiety is replaced by a substituent.

Preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1}$a), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

—R$^{x1}$, —R$^{x1a}$, —R$^{x1b}$ are independently of each other selected from the group consisting of —H, -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—; —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each T$^0$ is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T$^0$ is independently optionally substituted with one or more —R$^{x2}$, which are the same or different;

each —R$^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4}$a), —S(O)$_2$N(R$^{x4}$R$^{x4}$a), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4}$a), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and C$_{1-6}$ alkyl; wherein C$_{1-6}$ alkyl is optionally substituted with one or more halogen, which are the same or different;

each —R$^{x3}$, —R$^{x3a}$, —R$^{x4}$, —R$^{x4a}$, —R$^{x4b}$ is independently selected from the group consisting of —H and C$_{1-6}$ alkyl; wherein C$_{1-6}$ alkyl is optionally substituted with one or more halogen, which are the same or different.

More preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1}$a), —S(O)$_2$N(R$^{x1}$R$^{x1}$a), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1}$b), —OC(O)N(R$^{x1}$R$^{x1}$a), -T$^0$, C$_{1-10}$ alkyl, C$_{2-10}$ alkenyl, and C$_{2-10}$ alkynyl; wherein -T$^0$, C$_{1-10}$ alkyl, C$_{2-10}$ alkenyl, and C$_{2-10}$ alkynyl are optionally substituted with one or more —R$^{x2}$, which are the same or different and wherein C$_{1-10}$ alkyl, C$_{2-10}$ alkenyl, and C$_{2-10}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each —R$^{x1}$, —R$^{x1a}$, —R$^{x1b}$, —R$^{x3}$, —R$^{x3a}$ is independently selected from the group consisting of —H, halogen, C$_{1-6}$ alkyl, C$_{2-6}$ alkenyl, and C$_{2-6}$ alkynyl;

each T$^0$ is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T$^0$ is independently optionally substituted with one or more —R$^{x2}$, which are the same or different;

each —R$^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4}$a), —S(O)$_2$N(R$^{x4}$R$^{x4}$a), —S(O)N(R$^{x4}$R$^{x4a}$), —S(O)$_2$R$^{x4}$, —S(O)R$^{x4}$, —N(R$^{x4}$)S(O)$_2$N(R$^{x4}$R$^{x4b}$), —SR$^{x4}$, —N(R$^{x4}$R$^{x4}$a), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and C$_{1-6}$ alkyl; wherein C$_{1-6}$ alkyl is optionally substituted with one or more halogen, which are the same or different;

each —R$^{x4}$, —R$^{x4a}$, —R$^{x4b}$ is independently selected from the group consisting of —H, halogen, C$_{1-6}$ alkyl, C$_{2-6}$ alkenyl, and C$_{2-6}$ alkynyl;

Even more preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1}$a), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1}$b), —OC(O)N(R$^{x1}$R$^{x1}$a), -T$^0$, C$_{1-6}$ alkyl, C$_{2-6}$ alkenyl, and C$_{2-6}$ alkynyl; wherein -T$^0$, C$_{1-6}$ alkyl, C$_{2-6}$ alkenyl, and C$_{2-6}$ alkynyl are optionally substituted with one or more —R$^{x2}$, which are the same or different and wherein C$_{1-6}$ alkyl, C$_{2-6}$ alkenyl, and C$_{2-6}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each —R$^{x1}$, —R$^{x1a}$, —R$^{x1b}$, —R$^{x2}$, —R$^{x2}$, —R$^{x3a}$ is independently selected from the group consisting of —H, halogen, C$_{1-6}$ alkyl, C$_{2-6}$ alkenyl, and C$_{2-6}$ alkynyl;

each T$^0$ is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T$^0$ is independently optionally substituted with one or more —R$^{x2}$, which are the same or different.

Preferably, a maximum of 6 —H atoms of an optionally substituted molecule are independently replaced by a substituent, e.g. 5 —H atoms are independently replaced by a substituent, 4 —H atoms are independently replaced by a substituent, 3 —H atoms are independently replaced by a substituent, 2 —H atoms are independently replaced by a substituent, or 1 —H atom is replaced by a substituent.

The term "interrupted" means that a moiety is inserted between two carbon atoms or—if the insertion is at one of the moiety's ends—between a carbon and a hydrogen atom.

As used herein, the term "$C_{1-4}$ alkyl" alone or in combination means a straight-chain or branched alkyl moiety having 1 to 4 carbon atoms. If present at the end of a molecule, examples of straight-chain or branched $C_{1-4}$ alkyl are methyl, ethyl, n-propyl, isopropyl, n-butyl, isobutyl, sec-butyl and tert-butyl. When two moieties of a molecule are linked by the $C_{1-4}$ alkyl, then examples for such $C_{1-4}$ alkyl groups are —$CH_2$—, —$CH_2$—$CH_2$—, —$CH(CH_3)$—, —$CH_2$—$CH_2$—$CH_2$—, —$CH(C_2H_5)$—, —$C(CH_3)_2$—. Each hydrogen of a $C_{1-4}$ alkyl carbon may optionally be replaced by a substituent as defined above. Optionally, a $C_{1-4}$ alkyl may be interrupted by one or more moieties as defined below.

As used herein, the term "$C_{1-6}$ alkyl" alone or in combination means a straight-chain or branched alkyl moiety having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the $C_{1-6}$ alkyl group, then examples for such $C_{1-6}$ alkyl groups are —$CH_2$—, —$CH_2$—$CH_2$—, —$CH(CH_3)$—, —$CH_2$—$CH_2$—$CH_2$—, —$CH(C_2H_5)$— and —$C(CH_3)_2$—. Each hydrogen atom of a $C_{1-6}$ carbon may optionally be replaced by a substituent as defined above. Optionally, a $C_{1-6}$ alkyl may be interrupted by one or more moieties as defined below.

Accordingly, "$C_{1-10}$ alkyl", "$C_{1-20}$ alkyl" or "$C_{1-50}$ alkyl" means an alkyl chain having 1 to 10, 1 to 20 or 1 to 50 carbon atoms, respectively, wherein each hydrogen atom of the $C_{1-10}$, $C_{1-20}$ or $C_{1-50}$ carbon may optionally be replaced by a substituent as defined above. Optionally, a $C_{1-10}$ or $C_{1-50}$ alkyl may be interrupted by one or more moieties as defined below.

As used herein, the term "$C_{2-6}$ alkenyl" alone or in combination means a straight-chain or branched hydrocarbon moiety comprising at least one carbon-carbon double bond having 2 to 6 carbon atoms. If present at the end of a molecule, examples are —$CH=CH_2$, —$CH=CH$—$CH_3$, —$CH_2$—$CH=CH_2$, —$CH=CHCH_2$—$CH_3$ and —$CH=CH$—$CH=CH_2$. When two moieties of a molecule are linked by the $C_{2-6}$ alkenyl group, then an example for such $C_{2-6}$ alkenyl is —$CH=CH$—. Each hydrogen atom of a $C_{2-6}$ alkenyl moiety may optionally be replaced by a substituent as defined above. Optionally, a $C_{2-6}$ alkenyl may be interrupted by one or more moieties as defined below.

Accordingly, the term "$C_{2-10}$ alkenyl", "$C_{2-20}$ alkenyl" or "$C_{2-50}$ alkenyl" alone or in combination means a straight-chain or branched hydrocarbon moiety comprising at least one carbon-carbon double bond having 2 to 10, 2 to 20 or 2 to 50 carbon atoms. Each hydrogen atom of a $C_{2-10}$ alkenyl, $C_{2-20}$ alkenyl or $C_{2-50}$ alkenyl group may optionally be replaced by a substituent as defined above. Optionally, a $C_{2-10}$ alkenyl, $C_{2-20}$ alkenyl or $C_{2-50}$ alkenyl may be interrupted by one or more moieties as defined below.

As used herein, the term "$C_{2-6}$ alkynyl" alone or in combination means straight-chain or branched hydrocarbon moiety comprising at least one carbon-carbon triple bond having 2 to 6 carbon atoms. If present at the end of a molecule, examples are —$C\equiv CH$, —$CH_2$—$C\equiv CH$, $CH_2$—$CH_2$—$C\equiv CH$ and $CH_2$—$C\equiv C$—$CH_3$. When two moieties of a molecule are linked by the alkynyl group, then an example is —$C\equiv C$—. Each hydrogen atom of a $C_{2-6}$ alkynyl group may optionally be replaced by a substituent as defined above. Optionally, one or more double bond(s) may occur. Optionally, a $C_{2-6}$ alkynyl may be interrupted by one or more moieties as defined below.

Accordingly, as used herein, the term "$C_{2-10}$ alkynyl", "$C_{2-20}$ alkynyl" and "$C_{2-50}$ alkynyl" alone or in combination means a straight-chain or branched hydrocarbon moiety comprising at least one carbon-carbon triple bond having 2 to 10, 2 to 20 or 2 to 50 carbon atoms, respectively. Each hydrogen atom of a $C_{2-10}$ alkynyl, $C_{2-20}$ alkynyl or $C_{2-50}$ alkynyl group may optionally be replaced by a substituent as defined above. Optionally, one or more double bond(s) may occur. Optionally, a $C_{2-10}$ alkynyl, $C_{2-20}$ alkynyl or $C_{2-50}$ alkynyl may be interrupted by one or more moieties as defined below.

As mentioned above, a $C_{1-4}$ alkyl, $C_{1-6}$ alkyl, $C_{1-10}$ alkyl, $C_{1-20}$ alkyl, $C_{1-50}$ alkyl, $C_{2-6}$ alkenyl, $C_{2-10}$ alkenyl, $C_{2-20}$ alkenyl, $C_{2-50}$ alkenyl, $C_{2-6}$ alkynyl, $C_{2-10}$ alkynyl, $C_{2-20}$ alkynyl or $C_{2-50}$ alkynyl may optionally be interrupted by one or more of the following moieties:

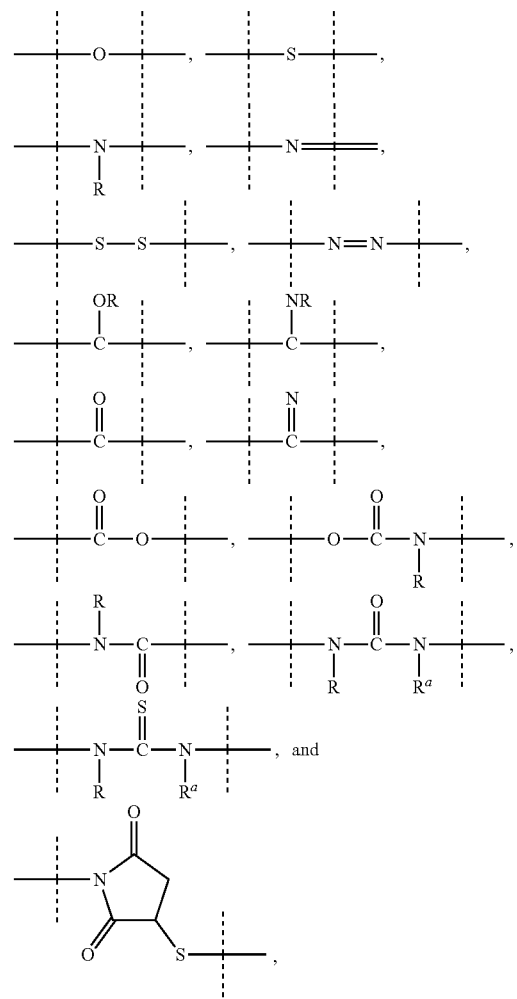

wherein
dashed lines indicate attachment to the remainder of the moiety or reagent; and
R and $R^a$ are independently of each other selected from the group consisting of H, methyl, ethyl, propyl, butyl, pentyl and hexyl.

As used herein, the term "$C_{3-10}$ cycloalkyl" means a cyclic alkyl chain having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl or cyclodecyl. Each hydrogen atom of a $C_{3-10}$ cycloalkyl carbon may be replaced by a substituent as defined above. The term "$C_{3-10}$ cycloalkyl" also includes bridged bicycles like norbornane or norbornene.

The term "8- to 30-membered carbopolycyclyl" or "8- to 30-membered carbopolycycle" means a cyclic moiety of two or more rings with 8 to 30 ring atoms, where two neighboring rings share at least one ring atom and that may contain up to the maximum number of double bonds (aromatic or non-aromatic ring which is fully, partially or un-saturated). Preferably a 8- to 30-membered carbopolycyclyl means a cyclic moiety of two, three, four or five rings, more preferably of two, three or four rings.

As used herein, the term "3- to 10-membered heterocyclyl" or "3- to 10-membered heterocycle" means a ring with 3, 4, 5, 6, 7, 8, 9 or 10 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for 3- to 10-membered heterocycles include but are not limited to aziridine, oxirane, thiirane, azirine, oxirene, thiirene, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 3- to 10-membered heterocyclyl or 3- to 10-membered heterocyclic group may be replaced by a substituent as defined below.

As used herein, the term "8- to 11-membered heterobicyclyl" or "8- to 11-membered heterobicycle" means a heterocyclic moiety of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for an 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

Similarly, the term "8- to 30-membered heteropolycyclyl" or "8- to 30-membered heteropolycycle" means a heterocyclic moiety of more than two rings with 8 to 30 ring atoms, preferably of three, four or five rings, where two neighboring rings share at least one ring atom and that may contain up to the maximum number of double bonds (aromatic or non-aromatic ring which is fully, partially or unsaturated), wherein at least one ring atom up to 10 ring atoms are replaced by a heteroatom selected from the group of sulfur (including —S(O)—, —S(O)$_2$—), oxygen and nitrogen (including =N(O)—) and wherein the ring is linked to the rest of a molecule via a carbon or nitrogen atom.

It is understood that that phrase "the pair —R$^1$/—R$^{1a}$ is joined together with the atom to which they are attached to form a $C_{3-10}$ cycloalkyl, 3- to 10-membered heterocyclyl or a 8- to 11-membered heterobicyclyl" refers to a moiety having the following structure:

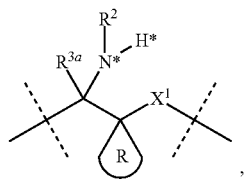

wherein <R is the $C_{3-10}$ cycloalkyl or a 3- to 10-membered heterocyclyl. This applies analogously to the pairs —R$^2$/—R$^3$, —R$^5$/—R$^{5a}$ and —R$^4$/—R$^{4a}$.

It is understood that the phrase "the pair —R$^1$/—R$^5$ is joined together with the atoms to which they are attached to form a ring A" refers to a moiety having the following structure:

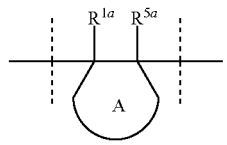

This applies analogously to the pairs —R$^1$/—R$^2$, —R$^1$/—R$^3$, —R$^1$/—R$^{5a}$, —R$^{1a}$/—R$^2$, —R$^{1a}$/—R$^3$, —R$^{1a}$/—R$^5$, —R$^{1a}$/—R$^{5a}$, —R$^2$/—R$^5$, —R$^2$/—R$^{5a}$, —R$^3$/—R$^5$, —R$^3$/—R$^{5a}$.

As used herein, the term "terminal alkyne" means a moiety

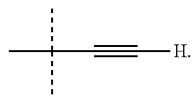

As used herein, "halogen" means fluoro, chloro, bromo or iodo. It is generally preferred that halogen is fluoro or chloro.

In general, the term "comprise" or "comprising" also encompasses "consist of" or "consisting of".

In one embodiment -D of formula (I) is a primary or secondary amine-comprising biologically active moiety which is connected to -L$^1$ through an amide linkage, i.e. —X$^1$— is —CR$^5$R$^{5a}$—.

-D of formula (I) is preferably selected from the group consisting of small molecule biologically active moiety, oligonucleotide moiety, peptide nucleic acid moiety, peptide moiety and protein moiety. More preferably -D of formula (I) is selected from the group consisting of small molecule biologically active moiety, peptide moiety and protein moiety.

In one preferred embodiment -D of formula (I) is a small molecule biologically active moiety.

In another preferred embodiment -D of formula (I) is a peptide moiety.

In another preferred embodiment -D of formula (I) is a protein moiety. In one preferred embodiment such protein moiety is a monoclonal or polyclonal antibody or fragment or fusion thereof.

Another aspect of the present invention is a prodrug reagent comprising a conjugate L'-Q, wherein
-Q is —OH or a leaving group; and
-L' comprises, preferably consists of, a linker moiety -L$^1$ represented by formula (I')

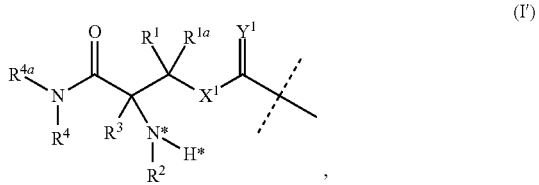

wherein
the dashed line indicates attachment to -Q;
—X$^1$ is selected from the group consisting of —CR$^5$R$^{5a}$—, —O—, —NR$^5$— and —S—;
—R$^1$, —R$^{1a}$, —R$^2$, —R$^3$, —R$^4$, —R$^{4a}$, —R$^5$, and —R$^{5a}$ are independently of other selected from —H, C$_{1-6}$ alkyl, C$_{2-6}$ alkenyl, and C$_{2-6}$ alkynyl; wherein C$_{1-6}$ alkyl, C$_{2-6}$ alkenyl, and C$_{2-6}$ alkenyl are optionally substituted with one or more —R$^6$, which are the same or different; and wherein C$_{1-6}$ alkyl, C$_{2-6}$ alkenyl, and C$_{2-6}$ alkynyl are optionally interrupted by one or more groups selected from the group consisting of -T-, —C(O)O—, —O—, —C(O)—, —C(O)N(R$^7$)—, —S(O)$_2$N(R$^7$)—, —S(O)N(R)—, —S(O)$_2$—, —S(O)—, —N(R$^7$)S(O)$_2$N(R$^{7a}$)—, —S—, —N(R$^7$)—, —OC(OR$^7$)(R$^{7a}$)—, —N(R$^7$)C(O)N (R$^{7a}$)—, and —OC(O)N(R$^7$)—; provided that the nitrogen marked with the asterisk is connected to —R$^2$ through an SP$^3$-hybridized carbon atom;
each T is independently of each other selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T is independently optionally substituted with one or more —R$^6$, which are the same or different;
each —R$^6$, —R$^7$, —R$^{7a}$ is independently selected from the group consisting of —H, and C$_{1-6}$ alkyl; wherein C$_{1-6}$ alkyl is optionally substituted with one or more halogen, which are the same or different;
=Y$^1$ is selected from =O and =NR$^5$;
Optionally, one or more of the pairs —R$^1$/—R$^{1a}$, —R$^2$/—R$^3$, —R$^5$/—R$^{5a}$ and —R$^4$/—R$^{4a}$ are joined together with the atom to which they are attached to form a C$_{3-10}$ cycloalkyl, 3- to 10-membered heterocyclyl or a 8- to 11-membered heterobicyclyl;

Optionally, one or more of the pairs —R$^1$/—R$^2$, —R$^1$/—R$^3$, —R$^1$/—R$^5$, —R$^1$/—R$^{5a}$, —R$^{1a}$/—R$^2$, —R$^{1a}$/—R$^3$, —R$^{1a}$/—R$^5$, —R$^{1a}$/—R$^{5a}$, —R$^2$/—R$^5$, —R$^2$/—R$^{5a}$, —R$^3$/—R$^5$, —R$^3$/—R$^{5a}$ are joined together with the atoms to which they are attached to form a ring -A-;

A is selected from the group consisting of phenyl; naphthyl; indenyl; indanyl; tetralinyl; C$_{3-10}$ cycloalkyl; 3- to 10-membered heterocyclyl; and 8- to 11-membered heterobicyclyl;

wherein -L$^1$ is substituted with one to five moieties -L$^2$-Z and/or -L$^{2'}$-Y, preferably -L$^1$ is substituted with one moiety -L$^2$-Z or -L$^{2'}$-Y, and is optionally further substituted, provided that the hydrogen marked with the asterisk in formula (I') is not replaced by a substituent;

wherein -L$^2$- and -L$^{2'}$- are independently of each other a single chemical bond or a spacer moiety;

-Z is a carrier moiety; and

—Y is a functional group which may optionally be present in its protected form.

Preferably, -Q of formula (I') is selected from the group consisting of chloride, bromide, fluoride, nitrophenoxy, imidazolyl, N-hydroxysuccinimidyl, N-hydroxybenzotriazolyl, N-hydroxyazobenzotriazolyl, pentafluorphenoxy, N-hydroxysulfosuccinimidyl, diphenylphosphinomethanethiyl, 2-diphenylphosphinophenoxy, norbornene-N-hydroxysuccinimidyl, N-hydroxyphthalimide, pyridinoxy, nonafluoro tert-butyloxy and hexafluoro isopropyloxy.

Preferably, —Y of formula (I') is selected from the group consisting of thiol, maleimide, amine, hydroxyl, carboxylic acid and derivatives, carbonate and derivatives, carbamate and derivatives, isothiocyanate, disulfide, pyridyl disulfide, methylthiosulfonyl, vinylsulfone, aldehyde, ketone, haloacetyl, selenide, azide, —NH—NH$_2$, —O—NH$_2$, a terminal alkyne, a compound of formula (z'i)

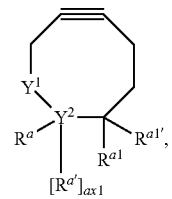

wherein
—Y$^1$—, —Y$^2$— are independently of each other —C— or —N—;
—R$^a$, —R$^{a'}$, —R$^{a1}$, —R$^{a1}$ are independently of each other —H or C$_{1-6}$ alkyl,
ax1 is 0, if —Y$^2$— is —N—; ax1 is 1, if —Y$^2$— is —C—,
optionally the pair —R$^a$/—R$^{a1}$ forms a chemical bond, if —Y$^2$— is —C—,
optionally, the pair —R$^{a'}$/—R$^{a1}$ are joined together with the atom to which they are attached to form a ring A', if —Y$^2$— is —C—,
A' is cyclopropyl or phenyl;
a compound of formula (z'ii)

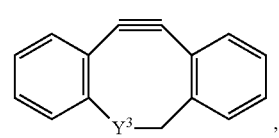

wherein
—$Y^3$— is —$CH_2$— or —NH—;

a compound of formula (z'iii)

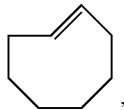

a compound of formula (z'iv)

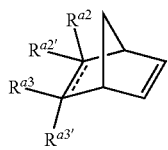

wherein
—$R^{a2}$ and —$R^{a3}$ are —H,
—$R^{a2'}$ and —$R^{a3'}$ are —H or are joined together with the atoms to which they are attached to form a 5-membered heterocyclyl ring A', and
----- indicates a single or double bond;

a compound of formula (z'v)

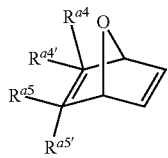

wherein
—$R^{a4}$, —$R^{a4'}$, $R^{a5}$, $R^{a5'}$ are —H,
optionally the pair —$R^{a4}$/—$R^{a5}$ forms a chemical bond,
optionally, the pair —$R^{a4'}$/—$R^{a5'}$ are joined together with the atoms to which they are attached to form a ring $A^{2'}$,
$A^{2'}$ is 5-membered heterocyclyl;

a compound of formula (z'vi)

wherein
—$R^{a6}$, —$R^{a6'}$ are either both $C_{1-6}$ alkyl or one of —$R^{a6}$, —$R^{a6'}$ is —H and the other one is selected from $C_{1-6}$ alkyl, —$COOR^{a7}$; —$CONHR^{a7'}$, and —$CH_2OR^{a7''}$, —$R^{a7}$, —$R^{a7'}$, —$R^{a7''}$ are independently of each other —H or $C_{1-4}$ alkyl;

a compound of formula (z'vii)

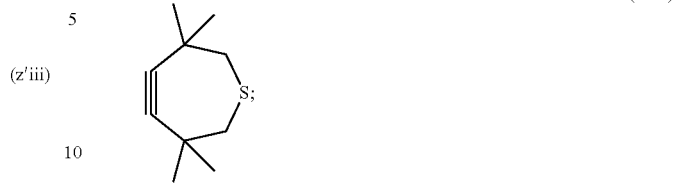

a compound of formula (z'viii)

wherein
—$R^{a8}$, —$R^{a8'}$, —$R^{a8''}$ are independently of each other selected from the group consisting of —H and $C_{1-4}$ alkyl;

a compound of formula (z'ix)

wherein
—$R^{a9}$ is —H or $C_{1-4}$ alkyl;

a compound of formula (z'x)

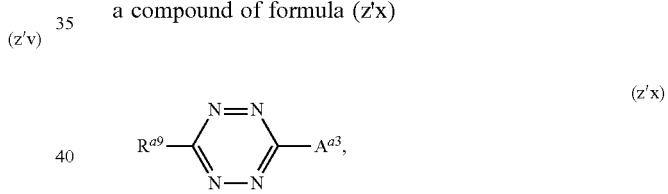

wherein
—$R^{a9}$ is selected from —$COOR^{a11}$, —$CONHR^{a11}$, and

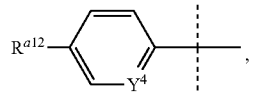

wherein
—$Y^4$— is —C— or —N—,
—$R^{a12}$ is selected from the group consisting of —H, —$COOR^{a13}$, —$CONR^{a13}R^{a13'}$, —$CH_2NR^{a13}R^{a13'}$, and —$NR^{a13}COR^{a13'}$, —$R^{a13}$, —$R^{a13'}$ are independently of each other selected from the group consisting of —H and $C_{1-4}$ alkyl,
-$A^{a3}$ is selected from —H, methyl, tert-butyl, —$CF_3$, —COOR,

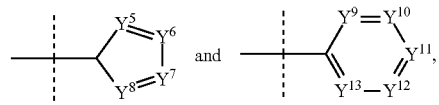

wherein
each —Y$^5$—, —Y$^6$—, —Y$^7$—, —Y$^8$— is independently of each other —C— or —N—, provided that no more than 3 of —Y$^5$—, —Y$^6$—, —Y$^7$—, —Y$^8$— are —N—,
each of —Y$^9$—, —Y$^{10}$—, —Y$^{11}$—, —Y$^{12}$—, —Y$^{13}$— is either —C—, —N—, —S— or —O—, provided that no more than 4 of —Y$^9$—, —Y$^{10}$—, —Y$^{11}$—, —Y$^{12}$—, —Y$^{13}$— are —N—, —S—, or —O—;

a compound of formula (z'xi)

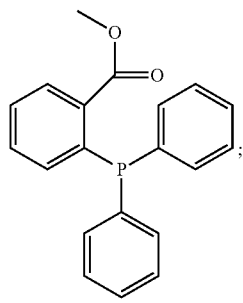

(z'xi)

a compound of formula (z'xii)

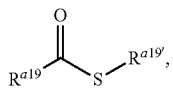

(z'xii)

wherein
—R$^{a9}$, —R$^{a18'}$ are independently of each other selected from the group consisting of —H, C$_{1-6}$ alkyl, C$_{2-6}$ alkenyl, C$_{2-6}$ alkynyl, C$_{3-8}$ cycloalkyl, 3- to 10-membered heterocyclyl, 8- to 11-membered heterobicyclyl, phenyl, naphthyl, indenyl, indanyl, and tetralinyl;

a compound of formula (z'xiii)

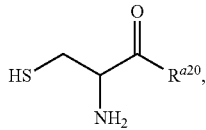

(z'xiii)

wherein
R$^{a20}$ is selected from the group consisting of —H, C$_{1-6}$ alkyl, C$_{2-6}$ alkenyl, C$_{2-6}$ alkynyl, C$_{3-8}$ cycloalkyl, 3- to 10-membered heterocyclyl, 8- to 11-membered heterobicyclyl, phenyl, naphthyl, indenyl, indanyl, and tetralinyl;

a compound of formula (z'xiv)

 (z'xiv), wherein
Ar is selected from phenyl, naphthyl, indenyl, indanyl, and tetralinyl,
—Y$^{14}$ is selected from halogen,
—R$^{a22}$, —R$^{a23}$, —R$^{a23'}$ are independently of each other selected from the group consisting of —H, C$_{1-6}$ alkyl, C$_{2-6}$ alkenyl, C$_{2-6}$ alkynyl, C$_{3-8}$ cycloalkyl, 3- to 10-membered heterocyclyl, 8- to 11-membered heterobicyclyl, phenyl, naphthyl, indenyl, indanyl, and tetralinyl;

a compound of formula (z'xv)

(z'xv)

Ar is selected from phenyl, naphthyl, indenyl, indanyl, and tetralinyl,
—R$^{a24}$, —R$^{a24'}$, —R$^{a24''}$, —R$^{a24'''}$ are independently of each other selected from the group consisting of —H, C$_{1-6}$ alkyl, C$_{2-6}$ alkenyl, C$_{2-6}$ alkynyl, C$_{3-8}$ cycloalkyl, 3- to 10-membered heterocyclyl, 8- to 11-membered heterobicyclyl, phenyl, naphthyl, indenyl, indanyl, and tetralinyl;

a compound of formula (z'xvi)

(z'xvi)

wherein
—R$^{a25}$ is selected from the group consisting of —H, C$_{1-6}$ alkyl, C$_{2-6}$ alkenyl, C$_{2-6}$ alkynyl, C$_{3-8}$ cycloalkyl, 3- to 10-membered heterocyclyl, 8- to 11-membered heterobicyclyl, phenyl, naphthyl, indenyl, indanyl, and tetralinyl;

a compound of formula (z'xvii)

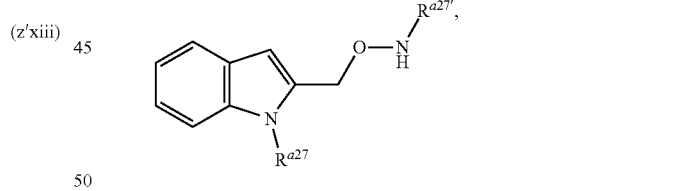

(z'xvii)

wherein
—R$^{a27}$, —R$^{a27'}$ are independently of each other —H or C$_{1-6}$ alkyl;

a compound of formula (z'xviii)

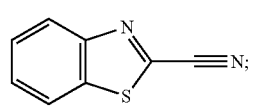

(z'xviii)

a compound of formula (z'xix)

 (z'xix), wherein
—PPh$_2$ represents a group having the following formula

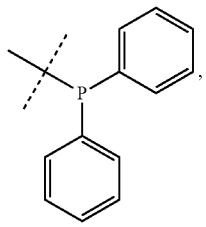

wherein the dashed line indicates attachment to the rest of the moiety of formula (z'xix),
—R$^{a12}$ is selected from

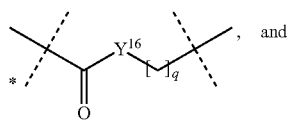

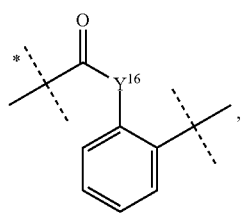

wherein
the unmarked dashed line indicates attachment to the rest of the moiety of formula (z'xix),
the dashed line with the asterisk indicates attachment to -L$^{2'}$-,
q is 1 or 2, and
—Y$^{14}$— is —O— or —S—;
and a compound of formula (z'xx)

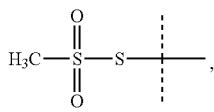

(z'xx)

wherein
the dashed line indicates attachment to -L$^{2'}$-;
wherein the moieties of formula (z'i), (z'ii), (z'iii), (z'iv), (z'v), (z'vi), (z'vii), (z'viii), (z'ix), (z'x), (z'xi), (z'xii), (z'xiii), (z'xiv), (z'xv), (z'xvi), (z'xvii) and (z'xviii) are substituted with a moiety -L$^{2'}$- and are optionally further substituted.
Preferably, —Y$^1$— of formula (z'i) is —C—.
Preferably, —R$^a$, —R$^{a'}$, —R$^{a1}$, —R$^{a1'}$ of formula (z'i) are —H.
Preferred embodiments of formula (z'i) are selected from the group consisting of

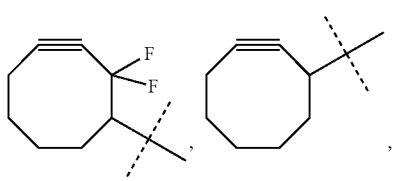

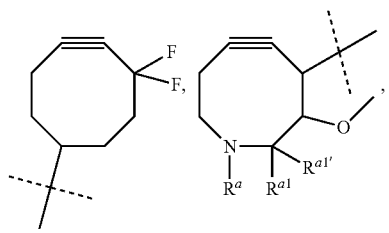

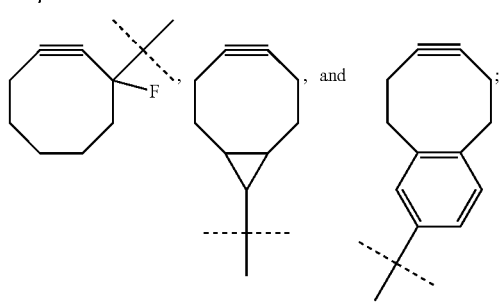

wherein
the dashed line indicates attachment to -L$^{2'}$-, and
—R$^a$, —R$^{a1}$, —R$^{a1'}$ are used as defined in formula (z'i).
Preferred embodiments of formula (z'ii) are

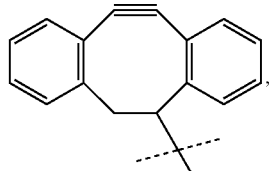

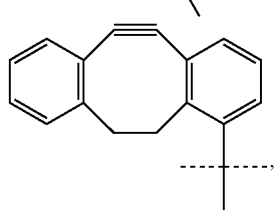

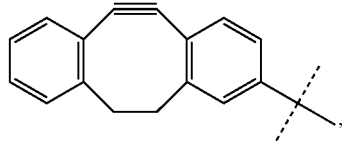

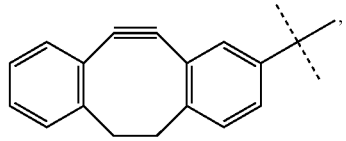

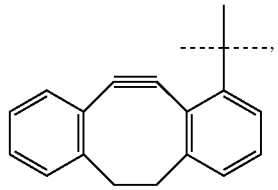

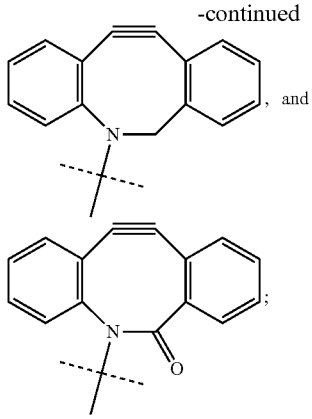, and

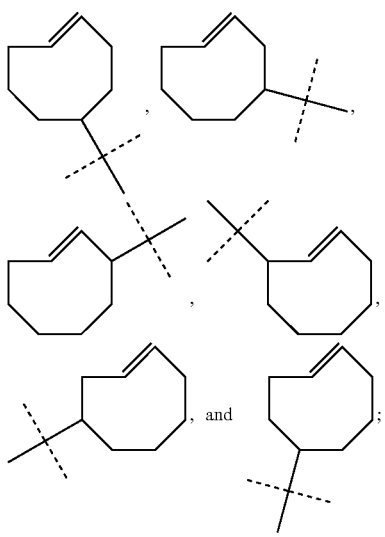;

wherein
the dashed line indicates attachment to -L$^{2'}$-.
Preferred embodiments of formula (z'iii) are

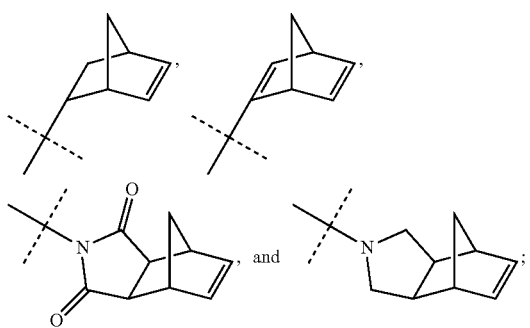

wherein
the dashed line indicates attachment to -L$^{2'}$-.
Preferred embodiments of formula (z'iv) are A preferred embodiment of formula (z'v) is

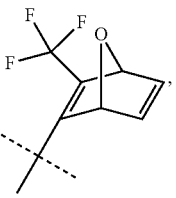, wherein
the dashed line indicates attachment to -L$^{2'}$-.
Preferred embodiments of formula (z'vi) are

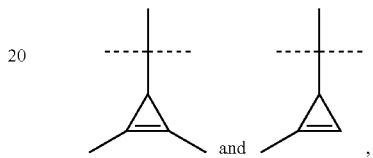

wherein
the dashed line indicates attachment to -L$^{2'}$-.
A preferred embodiments of formula (z'vii) is

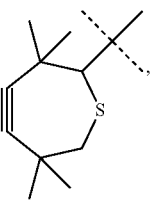, wherein
the dashed line indicates attachment to -L$^{2'}$-.
Preferred embodiments of formula (z'viii) are

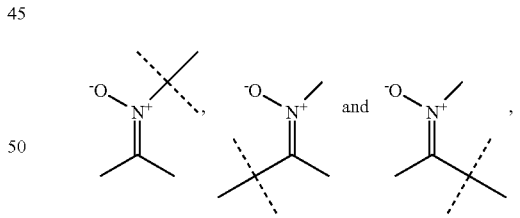

wherein
the dashed line indicates attachment to -L$^{2'}$-.
A preferred embodiment of formula (z'ix) is

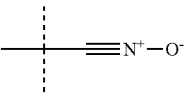

wherein
the dashed line indicates attachment to -L$^{2'}$-.

Preferred embodiments of $A^{a3}$ of formula (z'x) are

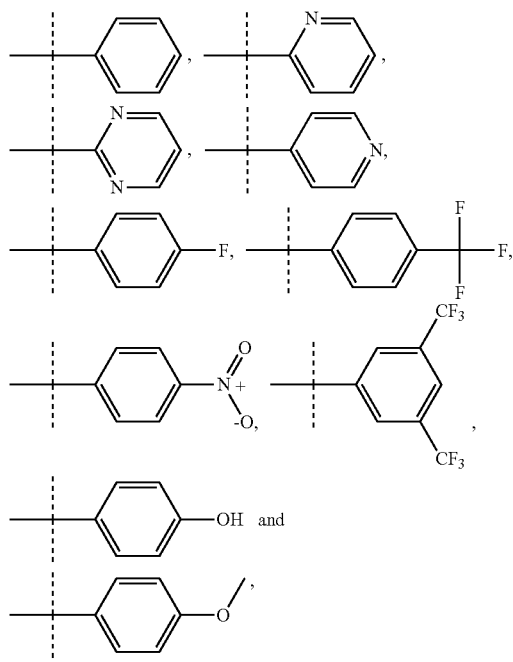

wherein
the dashed line indicates attachment to the remainder of (z'x).

Preferred embodiments of the moiety

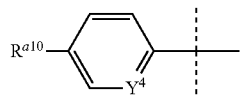

of formula (z'x) are

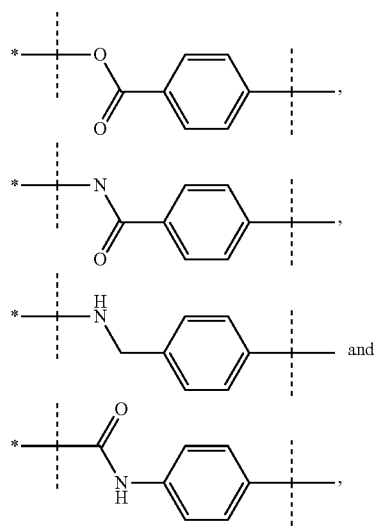

wherein
the unmarked dashed line indicates attachment to the remainder of (z'x) and
the dashed line marked with the asterisk indicates attachment to -$L^{2'}$-.

A preferred embodiment of formula (z'xii) is

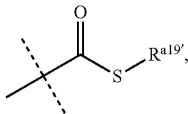

wherein
the dashed line indicates attachment to -$L^{2'}$-, and
—$R^{a19}$ is H, methyl, ethyl, propyl or butyl.

A preferred embodiment of formula (z'xiii) is

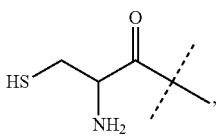

wherein
the dashed line indicates attachment to -$L^{2'}$-.

A preferred embodiment of formula (z'xiv) is

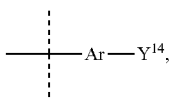

wherein
the dashed line indicates attachment to -$L^{2'}$-,
Ar is selected from phenyl, naphthyl, indenyl, indanyl, and tetralinyl, and —$Y^{14}$ is halogen.

A preferred embodiment of formula (z'xv) is

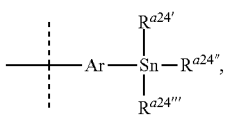

wherein
the dashed line indicates attachment to -$L^{2'}$-.
Ar is selected from the group consisting of phenyl, naphthyl, indenyl, indanyl, and tetralinyl; and
$R^{a24'}$, —$R^{a24''}$, —$R^{a24'''}$ are independently of each other selected from the group consisting of —H, methyl, ethyl, propyl and butyl.

A preferred embodiment of formula (z'xvi) is

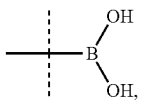

wherein
the dashed line indicates attachment to -$L^{2'}$-.

A preferred embodiment of formula (z'xvii) is

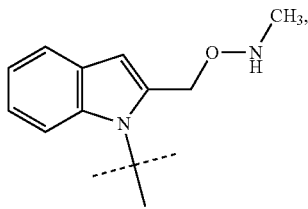

wherein
the dashed line indicates attachment to -L²-.

In a preferred embodiment —$X^1$— of formula (I) or (I') is —$CR^5R^{5a}$—.

In a preferred embodiment —$R^{4a}$ of formula (I) or (I') is —H which is substituted with -$L^2$-Z or -$L^2$-Y.

In a preferred embodiment =$Y^1$ of formula (I) or (I') is =O.

In one embodiment —$R^1$, —$R^{1a}$; —$R^2$, —$R^3$, —$R^4$, —$R^{4a}$, $R^5$, and —$R^{5a}$ are independently of other selected from —H, $C_{1-6}$ alkyl; $C_{2-6}$ alkenyl, and $C_{2-6}$ alkynyl.

In a preferred embodiment —$R^1$ of formula (I) or (I') is selected from —H, $C_{1-6}$ alkyl, $C_{2-6}$ alkenyl, and $C_{2-6}$ alkynyl; more preferably, —$R^1$ of formula (I) or (I') is selected from —H and $C_{1-6}$ alkyl. Even more preferably, —$R^1$ of formula (I) or (I') is selected from —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methybutyl, 1-methylbutyl and 1-ethylpropyl.

In a preferred embodiment —$R^{1a}$ of formula (I) or (I') is selected from —H, $C_{1-6}$ alkyl, $C_{2-6}$ alkenyl, and $C_{2-6}$ alkynyl; more preferably, —$R^{1a}$ of formula (I) or (I') is selected from —H and $C_{1-6}$ alkyl. Even more preferably, —$R^{1a}$ of formula (I) or (I') is selected from —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methybutyl, 1-methylbutyl and 1-ethylpropyl.

In a preferred embodiment —$R^2$ of formula (I) or (I') is selected from —H, $C_{1-6}$ alkyl, $C_{2-6}$ alkenyl, and $C_{2-6}$ alkynyl; more preferably, —$R^2$ of formula (I) or (I') is selected from —H and $C_{1-6}$ alkyl. Even more preferably, —$R^2$ of formula (I) or (I') is selected from —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methybutyl, 1-methylbutyl and 1-ethylpropyl.

In a preferred embodiment —$R^3$ of formula (I) or (I') is selected from —H, $C_{1-6}$ alkyl, $C_{2-6}$ alkenyl, and $C_{2-6}$ alkynyl; more preferably, —$R^3$ of formula (I) or (I') is selected from —H and $C_{1-6}$ alkyl. Even more preferably, —$R^3$ of formula (I) or (I') is selected from —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methybutyl, 1-methylbutyl and 1-ethylpropyl.

In a preferred embodiment —$R^4$ of formula (I) or (I') is selected from —H, $C_{1-6}$ alkyl, $C_{2-6}$ alkenyl, and $C_{2-6}$ alkynyl; more preferably, —$R^4$ of formula (I) or (I') is selected from —H and $C_{1-6}$ alkyl. Even more preferably, —$R^4$ of formula (I) or (I') is selected from —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methybutyl, 1-methylbutyl and 1-ethylpropyl.

In a preferred embodiment —$R^5$ of formula (I) or (I') is selected from —H, $C_{1-6}$ alkyl, $C_{2-6}$ alkenyl, and $C_{2-6}$ alkynyl; more preferably, —$R^5$ of formula (I) or (I') is selected from —H and $C_{1-6}$ alkyl. Even more preferably, —$R^5$ of formula (I) or (I') is selected from —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methybutyl, 1-methylbutyl and 1-ethylpropyl.

In a preferred embodiment —$R^{5a}$ of formula (I) or (I') is selected from —H, $C_{1-6}$ alkyl, $C_{2-6}$ alkenyl, and $C_{2-6}$ alkynyl; more preferably, —$R^{5a}$ of formula (I) or (I') is selected from —H and $C_{1-6}$ alkyl. Even more preferably, —$R^{5a}$ of formula (I) or (I') is selected from —H, methyl, ethyl, n-propyl, iso-propyl, n-butyl, sec-butyl, iso-butyl, tert-butyl, n-pentyl, 1,1-dimethylpropyl, 2,2-dimethylpropyl, 3-methybutyl, 1-methylbutyl and 1-ethylpropyl.

A preferred moiety -$L^1$ of formula (I) is of formula (Ia):

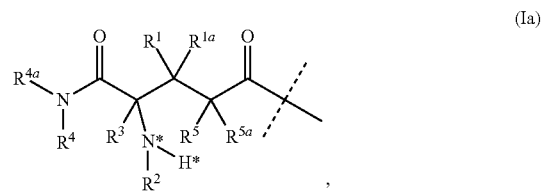

(Ia)

wherein
the dashed line indicates attachment to the primary or secondary amine of the biologically active moiety; and —$R^1$, —$R^a$, —$R^2$, —$R^3$, —$R^4$, —$R^{4a}$, —$R^5$ and —$R^{5a}$ are used as defined in formula (I).

In one embodiment —$R^5$ and —$R^{5a}$ of formula (Ia) are both —H.

In one embodiment —$R^1$ and —$R^{1a}$ of formula (Ia) are both —H.

In one embodiment —$R^2$ of formula (Ia) is —$CH_3$.

In one embodiment —$R^3$ of formula (Ia) is —$CH_3$.

In one embodiment —$R^4$ of formula (Ia) is —$CH_3$. In another embodiment —$R^4$ and —$R^{4a}$ of formula (Ia) are both —$CH_3$.

In one embodiment —$R^1$, —$R^{1a}$, —$R^2$, —$R^3$, —$R^4$, —$R^{4a}$, —$R^5$ and —$R^{5a}$ of formula (Ia) are —H.

In one embodiment —$R^1$, —$R^2$, —$R^3$, —$R^4$, —$R^{4a}$, —$R^5$ and —$R^{5a}$ of formula (Ia) are —H and —$R^{1a}$ is —$CH_3$.

In one embodiment —$R^1$, —$R^{1a}$, —R, —$R^{44}$, —$R^{4a}$, —$R^5$ and —$R^{5a}$ of formula (Ia) are —H and —$R^2$ is —$CH_3$.

In one embodiment —$R^1$, —$R^{1a}$, —$R^2$, —$R^4$, —$R^{4a}$, —$R^5$ and —$R^{5a}$ of formula (Ia) are —H and —$R^3$ is —$CH_3$.

In one embodiment —$R^1$, —$R^{1a}$, —$R^2$, —$R^3$, —$R^{4a}$, —$R^5$ and —$R^{5a}$ of formula (Ia) are —H and —$R^4$ is —$CH_3$.

In one embodiment —$R^1$, —$R^{1a}$, —$R^2$, —$R^3$, —$R^4$, —$R^{4a}$ and —$R^{5a}$ of formula (Ia) are —H and —$R^5$ is —$CH_3$.

In one embodiment —$R^1$, —$R^{1a}$, —$R^2$, —$R^3$, —$R^5$ and —$R^{5a}$ of formula (Ia) are —H and —$R^4$ and —$R^{4a}$ are —$CH_3$.

In one embodiment —$R^1$, —$R^{1a}$, —$R^3$, —$R^5$ and —$R^{5a}$ of formula (Ia) are —H and —$R^2$, —$R^4$ and —$R^{4a}$ are —$CH_3$.

In one embodiment —$R^1$, —$R^{1a}$, —$R^2$, —$R^5$ and —$R^{5a}$ of formula (Ia) are —H and —$R^3$, —$R^4$ and —$R^{4a}$ are —$CH_3$.

In one embodiment —$R^1$, —$R^{1a}$, —$R^5$ and —$R^{5a}$ of formula (Ia) are —H and —$R^2$, —$R^3$, —$R^4$ and —$R^{4a}$ are —$CH_3$.

A preferred moiety -L¹ of formula (I') is of formula (I'a):

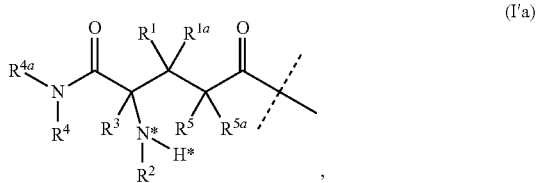

wherein
the dashed line indicates attachment to -Q; and
—R¹, —R¹ᵃ, —R², —R³, —R⁴, —R⁴ᵃ, —R⁵ and —R⁵ᵃ are used as defined in formula (I').

In a preferred embodiment, —R⁵ and —R⁵ᵃ of formula (I'a) are both —H.

In one embodiment —R¹ and —R¹ᵃ of formula (I'a) are both —H.

In one embodiment —R² of formula (I'a) is —CH₃.
In one embodiment —R³ of formula (I'a) is —CH₃.
In one embodiment —R⁴ of formula (I'a) is —CH₃. In another embodiment —R⁴ and —R⁴ᵃ of formula (Ia) are both —CH₃.

In one embodiment —R¹, —R¹ᵃ, —R², —R³, —R⁴, —R⁴ᵃ, —R⁵ and —R⁵ᵃ of formula (I'a) are —H.

In one embodiment —R¹, —R², —R³, —R⁴, —R⁴ᵃ, —R⁵ and —R⁵ᵃ of formula (I'a) are —H and —R¹ᵃ is —CH₃.

In one embodiment —R¹, —R¹ᵃ, —R³, —R⁴, —R⁴ᵃ, —R⁵ and —R⁵ᵃ of formula (I'a) are —H and —R² is —CH₃.

In one embodiment —R¹, —R¹ᵃ, —R², —R⁴, —R⁴ᵃ, —R⁵ and —R⁵ᵃ of formula (I'a) are —H and —R³ is —CH₃.

In one embodiment —R¹, —R¹ᵃ, —R², —R³, —R⁴ᵃ, —R⁵ and —R⁵ᵃ of formula (I'a) are —H and —R⁴ is —CH₃.

In one embodiment —R¹, —R¹ᵃ, —R², —R³, —R⁴, —R⁴ᵃ and —R⁵ᵃ of formula (I'a) are —H and —R⁵ is —CH₃.

In one embodiment —R¹, —R¹ᵃ, —R², —R³, —R⁵ and —R⁵ᵃ of formula (I'a) are —H and —R⁴ and —R⁴ᵃ are —CH₃.

In one embodiment —R¹, —R¹ᵃ, —R³, —R⁵ and —R⁵ᵃ of formula (I'a) are —H and —R², —R⁴ and —R⁴ᵃ are —CH₃.

In one embodiment —R¹, —R¹ᵃ, —R², —R⁵ and —R⁵ᵃ of formula (I'a) are —H and —R³, —R⁴ and —R⁴ᵃ are —CH₃.

In one embodiment —R¹, —R¹ᵃ, —R⁵ and —R⁵ᵃ of formula (I'a) are —H and —R², —R³, —R⁴ and —R⁴ᵃ are —CH₃.

Another preferred moiety -L of formula (I) is of formula (Ib):

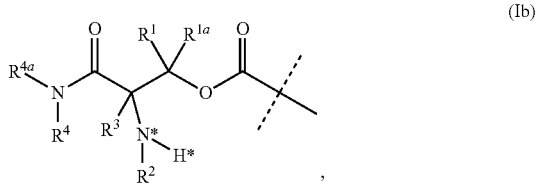

wherein
the dashed line indicates attachment to the primary or secondary amine of the biologically active moiety; and
—R¹, —R¹ᵃ, —R², —R³, —R⁴ and —R⁴ᵃ are used as defined in formula (I).

In one embodiment —R¹ and —R¹ᵃ of formula (Ib) are both —H.

In one embodiment —R² of formula (Ib) is —CH₃.
In one embodiment —R³ of formula (Ib) is —CH₃.
In one embodiment —R⁴ of formula (Ib) is —CH₃. In another embodiment —R⁴ and —R⁴ᵃ of formula (Ib) are both —CH₃.

In one embodiment —R¹, —R¹ᵃ, —R², —R³, —R⁴ and —R⁴ᵃ of formula (Ib) are —H.

In one embodiment —R¹, —R², —R³, —R⁴ and —R⁴ᵃ of formula (Ib) are —H and —R¹ᵃ is —CH₃.

In one embodiment —R¹, —R¹ᵃ, —R³, —R⁴ and —R⁴ᵃ of formula (Ib) are —H and —R² is —CH₃.

In one embodiment —R¹, —R¹ᵃ, —R², —R⁴ and —R⁴ᵃ of formula (Ib) are —H and —R³ is —CH₃.

In one embodiment —R¹, —R¹ᵃ, —R², —R³ and —R⁴ᵃ of formula (Ib) are —H and —R⁴ is —CH₃.

In one embodiment —R¹, —R¹ᵃ, —R and —R³ of formula (Ib) are —H and —R⁴ and —R⁴ᵃ are —CH₃.

In one embodiment —R¹, —R¹ᵃ and —R³ of formula (Ib) are —H and —R², —R⁴ and —R⁴ᵃ are —CH₃.

In one embodiment —R¹, —R¹ᵃ and —R² of formula (Ib) are —H and —R³, —R⁴ and —R⁴ᵃ are —CH₃.

In one embodiment —R¹ and —R¹ᵃ of formula (Ib) are —H and —R², —R³, —R⁴ and —R⁴ᵃ are —CH₃.

A preferred moiety -L¹ of formula (I') is of formula (I'b):

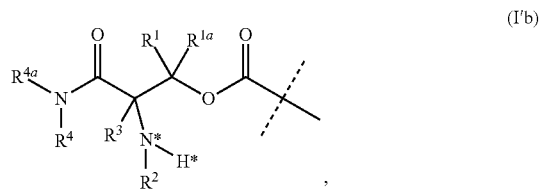

wherein
the dashed line indicates attachment to -Q; and
—R¹, —R¹ᵃ, —R², —R³, —R⁴ and —R⁴ᵃ are used as defined in formula (I').

In one embodiment —R¹ and —R¹ᵃ of formula (I'b) are both —H.

In one embodiment —R² of formula (I'b) is —CH₃.
In one embodiment —R³ of formula (I'b) is —CH₃.
In one embodiment —R⁴ of formula (I'b) is —CH₃. In another embodiment —R⁴ and —R⁴ᵃ of formula (I'b) are both —CH₃.

In one embodiment —R¹, —R¹ᵃ, —R², —R³, —R⁴ and —R⁴ᵃ of formula (I'b) are —H.

In one embodiment —R¹, —R², —R³, —R⁴ and —R⁴ᵃ of formula (I'b) are —H and —R¹ᵃ is —CH₃.

In one embodiment —R¹, —R¹ᵃ, —R³, —R⁴ and —R⁴ᵃ of formula (I'b) are —H and —R² is —CH₃.

In one embodiment —R¹, —R¹ᵃ, —R², —R⁴ and —R⁴ᵃ of formula (I'b) are —H and —R³ is —CH₃.

In one embodiment —R¹, —R¹ᵃ, —R², —R³ and —R⁴ᵃ of formula (I'b) are —H and —R⁴ is —CH₃.

In one embodiment —R¹, —R¹ᵃ, —R² and —R³ of formula (I'b) are —H and —R⁴ and —R⁴ᵃ are —CH₃.

In one embodiment —R¹, —R¹ᵃ and —R³ of formula (I'b) are —H and —R², —R⁴ and —R⁴ᵃ are —CH₃.

In one embodiment —R¹, —R¹ᵃ and —R² of formula (I'b) are —H and —R³, —R⁴ and —R⁴ᵃ are —CH₃.

In one embodiment —R¹ and —R¹ᵃ of formula (I'b) are —H and —R², —R³, —R⁴ and —R⁴ᵃ are —CH₃.

Another preferred moiety -L$^1$ of formula (I) is of formula (Ic):

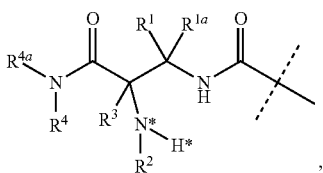

wherein
the dashed line indicates attachment to the primary or secondary amine of the biologically active moiety; and
—R$^1$, —R$^{1a}$, —R$^2$, —R$^3$, —R$^4$ and —R$^{4a}$ are used as defined in formula (I).

In one embodiment —R$^1$ and —R$^{1a}$ of formula (Ic) are both —H.
In one embodiment —R$^2$ of formula (Ic) is —CH$_3$.
In one embodiment —R$^3$ of formula (Ic) is —CH$_3$.
In one embodiment —R$^4$ of formula (Ic) is —CH$_3$. In another embodiment —R$^4$ and —R$^{4a}$ of formula (Ic) are both —CH$_3$.
In one embodiment —R$^1$, —R$^{22}$, —R$^3$, —R$^4$ and —R$^{4a}$ of formula (Ic) are —H.
In one embodiment —R$^1$, —R$^2$, —R$^3$, —R$^4$ and —R$^{4a}$ of formula (Ic) are —H and —R$^{1a}$ is —CH$_3$.
In one embodiment —R$^1$, —R$^{1a}$, —R$^3$, —R$^4$ and —R$^{4a}$ of formula (Ic) are —H and —R$^2$ is —CH$_3$.
In one embodiment —R$^1$, —R$^{1a}$, —R$^2$, —R$^4$ and —R$^{4a}$ of formula (Ic) are —H and —R is —CH$_3$.
In one embodiment —R$^1$, —R$^{1a}$, —R$^2$, —R$^3$ and —R$^{4a}$ of formula (Ic) are —H and —R$^4$ is —CH$_3$.
In one embodiment —R$^1$, —R$^{1a}$, —R$^2$ and —R$^3$ of formula (Ic) are —H and —R$^4$ and —R$^{4a}$ are —CH$_3$.
In one embodiment —R$^1$, —R$^{1a}$ and —R$^3$ of formula (Ic) are —H and —R$^2$, —R$^4$ and —R$^{4a}$ are —CH$_3$.
In one embodiment —R$^1$, —R$^{1a}$ and —R$^2$ of formula (Ic) are —H and —R$^3$, —R$^4$ and —R$^{4a}$ are —CH$_3$.
In one embodiment —R$^1$ and —R$^{1a}$ of formula (Ic) are —H and —R$^2$, —R$^3$, —R$^4$ and —R$^{4a}$ are —CH$_3$.

A preferred moiety -L$^1$ of formula (I') is of formula (I'c):

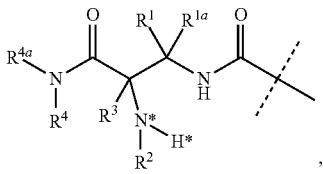

wherein
the dashed line indicates attachment to -Q; and
—R$^1$, —R$^{1a}$, —R$^2$, —R$^3$, —R$^4$ and —R$^{4a}$ are used as defined in formula (I').

In one embodiment —R$^1$ and —R$^{1a}$ of formula (I'c) are both —H.
In one embodiment —R$^2$ of formula (I'c) is —CH$_3$.
In one embodiment —R$^3$ of formula (I'c) is —CH$_3$.
In one embodiment —R$^4$ of formula (I'c) is —CH$_3$. In another embodiment —R$^4$ and —R$^{4a}$ of formula (I'c) are both —CH$_3$.
In one embodiment —R$^1$, —R$^{1a}$, —R$^2$, —R$^3$, —R$^4$ and —R$^{4a}$ of formula (I'c) are —H.

In one embodiment —R$^1$, —R$^2$, —R$^3$, —R$^4$ and —R$^{4a}$ of formula (I'c) are —H and —R$^{1a}$ is —CH$_3$.
In one embodiment —R$^1$, —R$^{1a}$, —R$^3$, —R$^4$ and —R$^{4a}$ of formula (I'c) are —H and —R$^2$ is —CH$_3$.
In one embodiment —R$^1$, —R$^{1a}$, —R$^2$, —R$^4$ and —R$^{4a}$ of formula (I'c) are —H and —R$^3$ is —CH$_3$.
In one embodiment —R$^1$, —R$^{1a}$, —R$^2$, —R$^3$ and —R$^{4a}$ of formula (I'c) are —H and —R$^4$ is —CH$_3$.
In one embodiment —R$^1$, —R$^{1a}$, —R$^2$ and —R$^3$ of formula (I'c) are —H and —R$^4$ and —R$^{4a}$ are —CH$_3$.
In one embodiment —R$^1$, —R$^{1a}$ and —R$^3$ of formula (I'c) are —H and —R$^2$, —R$^4$ and —R$^{4a}$ are —CH$_3$.
In one embodiment —R$^1$, —R$^a$ and —R$^2$ of formula (I'c) are —H and —R$^3$, —R$^4$ and —R$^{4a}$ are —CH$_3$.
In one embodiment —R$^1$ and —R$^{1a}$ of formula (I'c) are —H and —R$^2$, —R$^3$, —R$^4$ and —R$^{4a}$ are —CH$_3$.

-Z is a carrier. Preferably, -Z comprises a C$_{8-18}$ alkyl group or a polymer with a molecular weight of at least 0.5 kDa.

In one embodiment -Z comprises a C$_{8-18}$ alkyl group.
In another embodiment -Z comprises a polymer with a molecular weight of at least 0.5 kDa.

Preferably, a polymeric carrier -Z comprises at least one of the polymers selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyloxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In a preferred embodiment the poly(amide) is a peptide or protein.

In a preferred embodiment -Z comprises a protein. Even more preferably, -Z comprises a protein selected from the group consisting of albumin, transferrin, and immunoglobulin.

In another preferred embodiment -Z comprises a protein carrier as disclosed in WO2013/024049A1, which is hereby incorporated by reference.

In another preferred embodiment -Z comprises a PEG-based polymer comprising at last 10% PEG, such as at least 20% PEG, at least 30% PEG, at least 40% PEG or at least 50% PEG; or a hyaluronic acid-based polymer comprising at least 10% hyaluronic acid, such as at least 20% hyaluronic acid, at least 30% hyaluronic acid, at least 40% hyaluronic acid or at least 50% hyaluronic acid.

In one embodiment -Z comprises a water-soluble polymer with a molecular weight of at least 0.5 kDa.

Preferably, -Z comprises a linear, branched or dendritic PEG-based polymer comprising at least 10% PEG (such as at least 20% PEG, at least 30% PEG, at least 40% PEG or at least 50% PEG) with a molecular weight from 2,000 Da to 150,000 Da. Even more preferably -Z comprises a PEG-based carrier as disclosed in WO2103/024047 A1 and WO2013/024047 A1, which are hereby incorporated by reference.

A preferred water-soluble PEG-based carrier -Z is a multi-arm PEG derivative as, for instance, detailed in the products list of JenKem Technology (USA), such as a 4-arm-PEG derivative, in particular a 4-arm-PEG comprising a pentaerythritol core, an 8-arm-PEG derivative comprising a hexaglycerin core, and an 8-arm-PEG derivative comprising a tripentaerythritol core. More preferably, such water-soluble PEG-based carrier -Z comprises a moiety selected from:

a 4-arm PEG Amine comprising a pentaerythritol core:

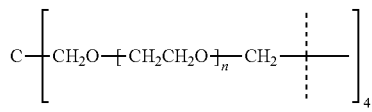

with n ranging from 20 to 500;
an 8-arm PEG Amine comprising a hexaglycerin core:

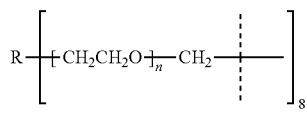

with n ranging from 20 to 500; and
—R=hexaglycerin or tripentaerythritol core structure; and
a 6-arm PEG Amine comprising a sorbitol or dipentaerythritol core:

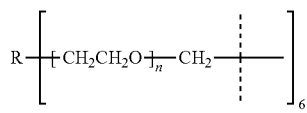

with n ranging from 20 to 500; and
—R=comprising a sorbitol or dipentaerythritol core;
wherein dashed lines indicate attachment to the rest of the prodrug.

In another embodiment -Z comprises a water-insoluble polymer.

Preferably, -Z comprises a water-insoluble hydrogel, more preferably a PEG-based hydrogel comprising at least 10% PEG (such as at least 20% PEG, at least 30% PEG, at least 40% PEG or at least 50% PEG) or a hyaluronic acid-based hydrogel comprising at least 10% hyaluronic acid (such as at least 20% hyaluronic acid, at least 30% hyaluronic acid, at least 40% hyaluronic acid or at least 50% hyaluronic acid) and most preferably -Z comprises a hydrogel as disclosed in WO2006/003014 A2, WO2011/012715 A1 or WO2014/056926 A1, which are hereby incorporated by reference.

In an even more preferred embodiment -Z comprises a hydrogel obtained from a process for the preparation of a hydrogel comprising the steps of:

(a) providing a mixture comprising
(a-i) at least one backbone reagent, wherein the at least one backbone reagent has a molecular weight ranging from 1 to 100 kDa, and comprises at least three functional groups $A^{x0}$, wherein each $A^{x0}$ is a maleimide, amine (—NH$_2$ or —NH—), hydroxyl (—OH), thiol (—SH), carboxyl (—COOH) or activated carboxyl (—COY$^1$, wherein Y$^1$ is selected from formulas (f-i) to (f-vii):

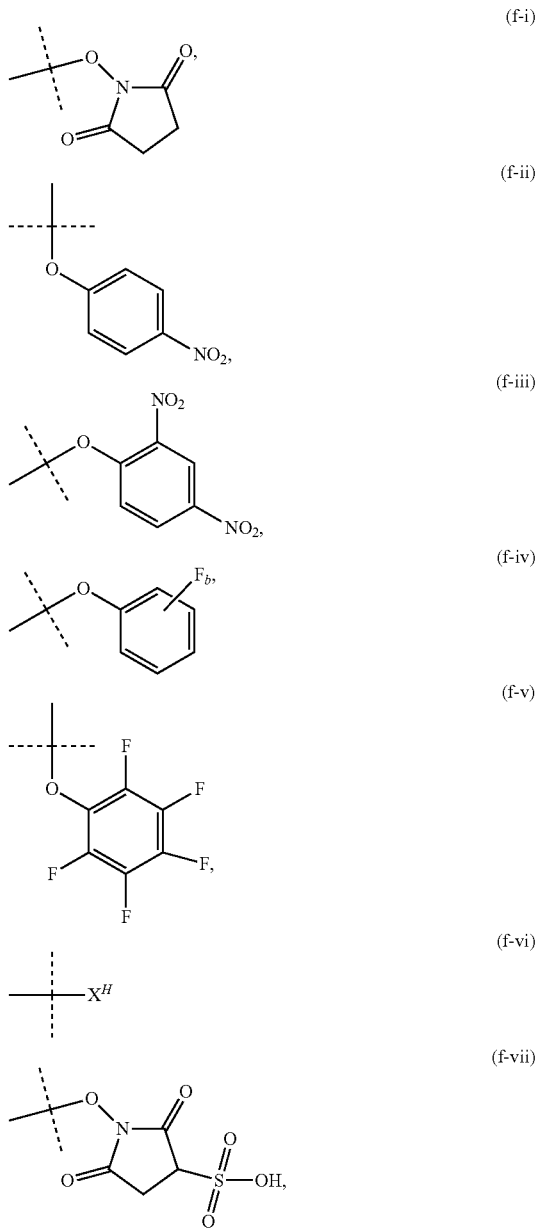

wherein
the dashed lines indicate attachment to the rest of the molecule,
b is 1, 2, 3 or 4,
$X^H$ is Cl, Br, I, or F);
(a-ii) at least one crosslinker reagent, wherein the at least one crosslinker reagent has a molecular weight ranging from 0.2 to 40 kDa and comprises at least two functional end groups selected from the group consisting of activated ester groups, activated carbamate groups, activated carbonate groups, activated thiocarbonate groups, amine groups and thiol groups;

in a weight ratio of the at least one backbone reagent to the at least one crosslinker reagent ranging from 1:99 to 99:1 and wherein the molar ratio of $A^{x0}$ to functional end groups is >1;

(b) polymerizing the mixture of step (a) in a suspension polymerization to a hydrogel.

Preferably, the crosslinker reagent of step (a-ii) comprises at least one reversible linkage.

Even more preferably, such at least one reversible linkage is an ester and/or carbonate.

The mixture of step (a) comprises a first solvent and at least a second solvent. Said first solvent is preferably selected from the group comprising dichloromethane, chloroform, tetrahydrofuran, ethyl acetate, dimethylformamide, acetonitrile, dimethyl sulfoxide, propylene carbonate, N-methylpyrrolidone, methanol, ethanol, isopropanol and water and mixtures thereof.

The at least one backbone reagent and at least one crosslinker reagent are dissolved in the first solvent, i.e. the disperse phase of the suspension polymerization. In one embodiment the backbone reagent and the crosslinker reagent are dissolved separately, i.e. in different containers, using either the same or different solvent and preferably using the same solvent for both reagents. In another embodiment, the backbone reagent and the crosslinker reagent are dissolved together, i.e. in the same container and using the same solvent.

A suitable solvent for the backbone reagent is an organic solvent. Preferably, the solvent is selected from the group consisting of dichloromethane, chloroform, tetrahydrofuran, ethyl acetate, dimethylformamide, acetonitrile, dimethyl sulfoxide, propylene carbonate, N-methylpyrrolidone, methanol, ethanol, isopropanol and water and mixtures thereof. More preferably, the backbone reagent is dissolved in a solvent selected from the group comprising acetonitrile, dimethyl sulfoxide, methanol or mixtures thereof. Most preferably, the backbone reagent is dissolved in dimethylsulfoxide.

In one embodiment the backbone reagent is dissolved in the solvent in a concentration ranging from 1 to 300 mg/ml, more preferably from 5 to 60 mg/ml and most preferably from 10 to 40 mg/ml.

A suitable solvent for the crosslinker reagent is an organic solvent. Preferably, the solvent is selected from the group comprising dichloromethane, chloroform, tetrahydrofuran, ethyl acetate, dimethylformamide, acetonitrile, dimethyl sulfoxide, propylene carbonate, N-methylpyrrolidone, methanol, ethanol, isopropanol, water or mixtures thereof. More preferably, the crosslinker reagent is dissolved in a solvent selected from the group comprising dimethylformamide, acetonitrile, dimethyl sulfoxide, methanol or mixtures thereof. Most preferably, the crosslinker reagent is dissolved in dimethylsulfoxide.

In one embodiment the crosslinker reagent is dissolved in the solvent in a concentration ranging from 5 to 500 mg/ml, more preferably from 25 to 300 mg/ml and most preferably from 50 to 200 mg/ml.

The at least one backbone reagent and the at least one crosslinker reagent are mixed in a weight ratio ranging from 1:99 to 99:1, e.g. in a ratio ranging from 2:98 to 90:10, in a weight ratio ranging from 3:97 to 88:12, in a weight ratio ranging from 3:96 to 85:15, in a weight ratio ranging from 2:98 to 90:10 and in a weight ratio ranging from 5:95 to 80:20; particularly preferred in a weight ratio from 5:95 to 80:20, wherein the first number refers to the backbone reagent and the second number to the crosslinker reagent.

Preferably, the ratios are selected such that the mixture of step (a) comprises a molar excess of functional groups $A^{x0}$ from the backbone reagent compared to the activated functional end groups of the crosslinker reagent. Consequently, the hydrogel resulting from the process has free functional groups $A^{x0}$ which can be used to couple other moieties to the hydrogel, such as spacers, and/or reversible prodrug linker moieties $L^1$.

The at least one second solvent, i.e. the continuous phase of the suspension polymerization, is preferably an organic solvent, more preferably an organic solvent selected from the group comprising linear, branched or cyclic $C_{5-30}$ alkanes; linear, branched or cyclic $C_{5-30}$ alkenes; linear, branched or cyclic $C_{5-30}$ alkynes; linear or cyclic poly (dimethylsiloxanes); aromatic $C_{6-20}$ hydrocarbons; and mixtures thereof. Even more preferably, the at least second solvent is selected from the group comprising linear, branched or cyclic $C_{5-16}$ alkanes; toluene; xylene; mesitylene; hexamethyldisiloxane; or mixtures thereof. Most preferably, the at least second solvent selected from the group comprising linear $C_{7-11}$ alkanes, such as heptane, octane, nonane, decane and undecane.

Preferably, the mixture of step (a) further comprises a detergent. Preferred detergents are Cithrol DPHS, Hypermer 70A, Hypermer B246, Hypermer 1599A, Hypermer 2296, and Hypermer 1083.

Preferably, the detergent has a concentration of 0.1 g to 100 g per 1 L total mixture, i.e. disperse phase and continuous phase together. More preferably, the detergent has a concentration of 0.5 g to 10 g per 1 L total mixture, and most preferably, the detergent has a concentration of 0.5 g to 5 g per 1 L total mixture.

Preferably, the mixture of step (a) is an emulsion.

The polymerization in step (b) is initiated by adding a base. Preferably, the base is a non-nucleophilic base soluble in alkanes, more preferably the base is selected from N,N,N',N'-tetramethylethylene diamine (TMEDA), 1,4-dimethylpiperazine, 4-methylmorpholine, 4-ethylmorpholine, 1,4-diazabicyclo[2.2.2]octane, 1,1,4,7,10,10-hexamethyltriethylenetetramine, 1,4,7-trimethyl-1,4,7-triazacyclononane, tris[2-(dimethylamino)ethyl]amine, triethylamine, DIPEA, trimethylamine, N,N-dimethylethylamine, N,N,N',N'-tetramethyl-1,6-hexanediamine, N,N,N',N'',N''-pentamethyldiethylenetriamine, 1,8-diazabicyclo [5.4.0]undec-7-ene, 1,5-diazabicyclo[4.3.0]non-5-ene, and hexamethylenetetramine. Even more preferably, the base is selected from TMEDA, 1,4-dimethylpiperazine, 4-methylmorpholine, 4-ethylmorpholine, 1,4-diazabicyclo[2.2.2]octane, 1,1,4,7,10,10-hexamethyltriethylenetetramine, 1,4,7-trimethyl-1,4,7-triazacyclononane, tris[2-(dimethylamino) ethyl]amine, 1,8-diazabicyclo[5.4.0]undec-7-ene, 1,5-diazabicyclo[4.3.0]non-5-ene, and hexamethylenetetramine. Most preferably, the base is TMEDA.

The base is added to the mixture of step (a) in an amount of 1 to 500 equivalents per activated functional end group in the mixture, preferably in an amount of 5 to 50 equivalents, more preferably in an amount of 5 to 25 equivalents and most preferably in an amount of 10 equivalents.

In process step (b), the polymerization of the hydrogel is a condensation reaction, which preferably occurs under continuous stirring of the mixture of step (a). Preferably, the tip speed (tip speed=π×stirrer rotational speed×stirrer diameter) ranges from 0.2 to 10 meter per second (m/s), more preferably from 0.5 to 4 m/s and most preferably from 1 to 2 m/s.

In a preferred embodiment of step (b), the polymerization reaction is carried out in a cylindrical vessel equipped with baffles. The diameter to height ratio of the vessel may range from 4:1 to 1:2, more preferably the diameter to height ratio of the vessel ranges from 2:1 to 1:1.

Preferably, the reaction vessel is equipped with an axial flow stirrer selected from the group comprising pitched blade stirrer, marine type propeller, or Lightnin A-310. More preferably, the stirrer is a pitched blade stirrer.

Step (b) can be performed in a broad temperature range, preferably at a temperature from −10° C. to 100° C., more preferably at a temperature of 0° C. to 80° C., even more preferably at a temperature of 10° C. to 50° C. and most preferably at ambient temperature. "Ambient temperature" refers to the temperature present in a typical laboratory environment and preferably means a temperature ranging from 17 to 25° C.

Preferably, the hydrogel obtained from the polymerization is a shaped article, such as a coating, mesh, stent, nanoparticle or a microparticle. More preferably, the hydrogel is in the form of microparticular beads having a diameter from 1 to 500 micrometer, more preferably with a diameter from 10 to 300 micrometer, even more preferably with a diameter from 20 and 150 micrometer and most preferably with a diameter from 30 to 130 micrometer. The afore-mentioned diameters are measured when the hydrogel microparticles are fully hydrated in water.

In one embodiment the process for the preparation of a hydrogel further comprises the step of:

(c) working-up the hydrogel.

Step (c) comprises one or more of the following step(s):

(c1) removing excess liquid from the polymerization reaction,
(c2) washing the hydrogel to remove solvents used during polymerization,
(c3) transferring the hydrogel into a buffer solution,
(c4) size fractionating/sieving of the hydrogel,
(c5) transferring the hydrogel into a container,
(c6) drying the hydrogel,
(c7) transferring the hydrogel into a specific solvent suitable for sterilization, and
(c8) sterilizing the hydrogel, preferably by gamma radiation Preferably, step (c) comprises all of the following steps (c1) removing excess liquid from the polymerization reaction,
(c2) washing the hydrogel to remove solvents used during polymerization,
(c3) transferring the hydrogel into a buffer solution,
(c4) size fractionating/sieving of the hydrogel,
(c5) transferring the hydrogel into a container,
(c7) transferring the hydrogel into a specific solvent suitable for sterilization, and
(c8) sterilizing the hydrogel, preferably by gamma radiation.

The at least one backbone reagent has a molecular weight ranging from 1 to 100 kDa, preferably from 2 to 50 kDa, more preferably from 5 and 30 kDa, even more preferably from 5 to 25 kDa and most preferably from 5 to 15 kDa.

Preferably, the backbone reagent is PEG-based comprising at least 10% PEG, more preferably comprising at least 20% PEG, even more preferably comprising at least 30% PEG and most preferably comprising at least 40% PEG.

In one embodiment the backbone reagent of step (a-i) is present in the form of its acidic salt, preferably in the form of an acid addition salt. Suitable acid addition salts are formed from acids which form non-toxic salts. Examples include but are not limited to the acetate, aspartate, benzoate, besylate, bicarbonate, carbonate, bisulphate, sulphate, borate, camsylate, citrate, edisylate, esylate, formate, fumarate, gluceptate, gluconate, glucuronate, hexafluorophosphate, hibenzate, hydrochloride, hydrobromide, hydroiodide, isethionate, lactate, malate, maleate, malonate, mesylate, methylsulphate, naphthylate, nicotinate, nitrate, orotate, oxalate, palmitate, pamoate, phosphate, hydrogen phosphate, dihydrogen phosphate, sacharate, stearate, succinate, tartrate and tosylate. Particularly preferred, the backbone reagent is present in the form of its hydrochloride salt.

In one embodiment, the at least one backbone reagent is selected from the group consisting of a compound of formula (aI)

$$B(-(A^0)_{x1}-(SP)_{x2}-A^1-P-A^2-Hyp^1)_x \qquad (aI),$$

wherein

B is a branching core,

SP is a spacer moiety selected from the group consisting of $C_{1-6}$ alkyl, $C_{2-6}$ alkenyl and $C_{2-6}$ alkynyl, P is a PEG-based polymeric chain comprising at least 80% PEG, preferably at least 85% PEG, more preferably at least 90% PEG and most preferably at least 95% PEG, $Hyp^1$ is a moiety comprising an amine ($-NH_2$ and/or $-NH-$) or a polyamine comprising at least two amines ($-NH_2$ and/or $-NH-$), x is an integer from 3 to 16, x1, x2 are independently of each other 0 or 1, provided that x1 is 0, if x2 is 0, $A^0, A^1, A^2$ are independently of each other selected from the group consisting of

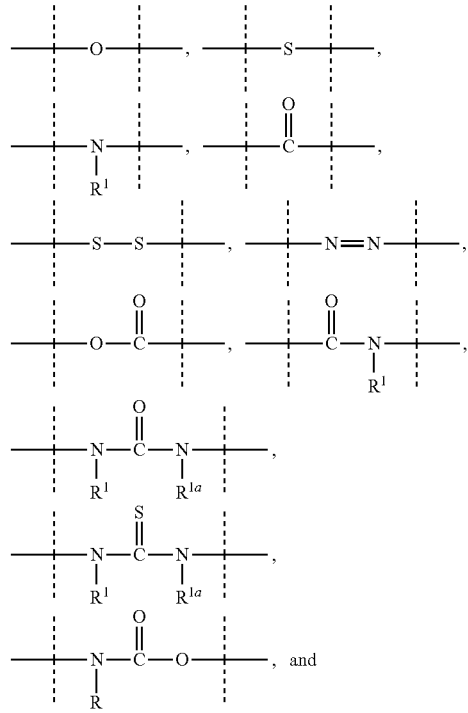

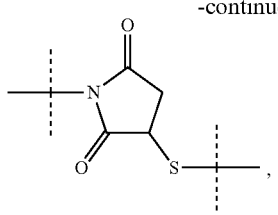

wherein $R^1$ and $R^{1a}$ are independently of each other selected from H and $C_{1-6}$ alkyl;

a compound of formula (aII)

$$\text{Hyp}^2\text{-}A^3\text{-}P\text{-}A^4\text{-}\text{Hyp}^3 \quad \text{(aII)},$$

wherein

P is defined as above in the compound of formula (aI), $\text{Hyp}^2$, $\text{Hyp}^3$ are independently of each other a polyamine comprising at least two amines (—$NH_2$ and/or —NH—), and $A^3$ and $A^4$ are independently selected from the group consisting of

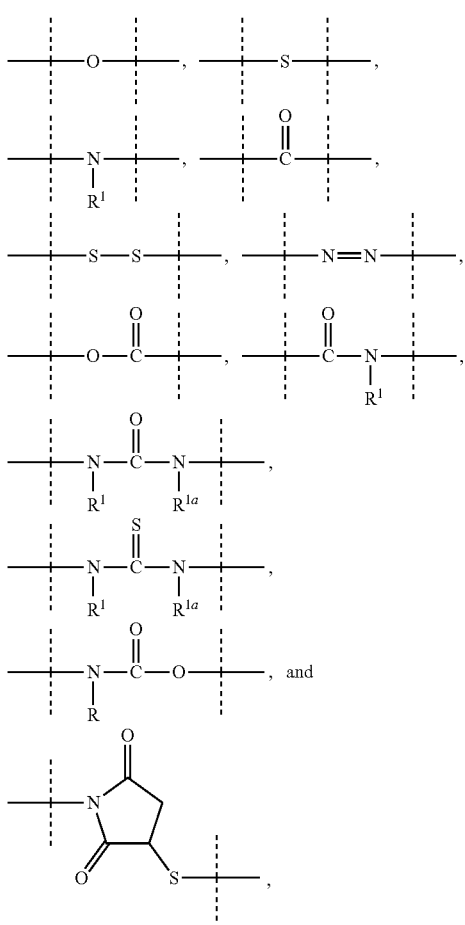

wherein $R^1$ and $R^{1a}$ are independently of each other selected from H and $C_{1-6}$ alkyl;

a compound of formula (aIII)

$$P^1\text{-}A^5\text{-}\text{Hyp}^4 \quad \text{(aIII)},$$

wherein $P^1$ is a PEG-based polymeric chain comprising at least 80% PEG, preferably at least 85% PEG, more preferably at least 90% PEG and most preferably at least 95% PEG, $\text{Hyp}^4$ is a polyamine comprising at least three amines (—$NH_2$ and/or —NH), and $A^5$ is selected from the group consisting of

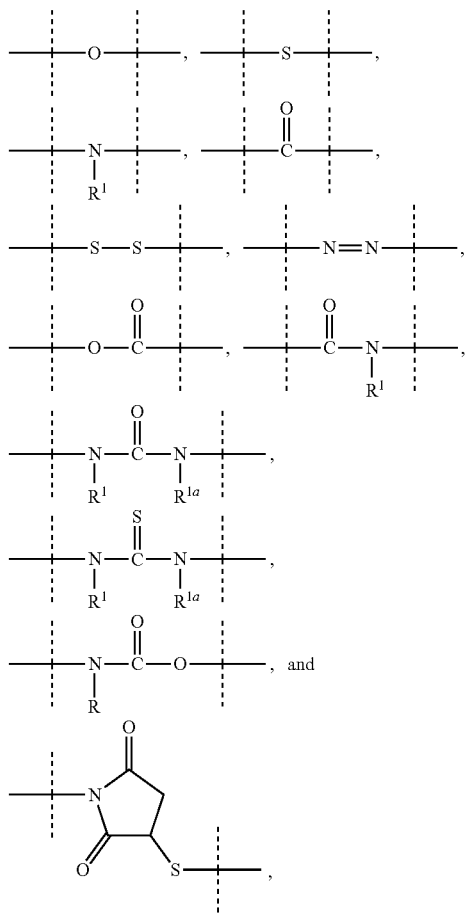

wherein $R^1$ and $R^{1a}$ are independently of each other selected from H and $C_{1-6}$ alkyl; and a compound of formula (aIV), $$T^1\text{-}A^6\text{-}\text{Hyp}^5 \quad \text{(aIV)},$$

wherein $\text{Hyp}^5$ is a polyamine comprising at least three amines (—$NH_2$ and/or —NH), and $A^6$ is selected from the group consisting of

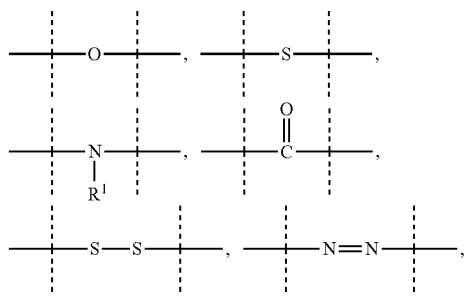

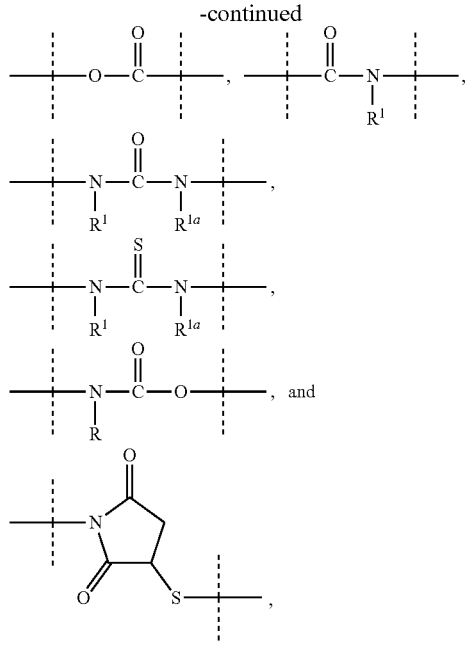

wherein $R^1$ and $R^{1a}$ are independently of each other selected from H and $C_{1-6}$ alkyl; and $T^1$ is selected from the group consisting of $C_{1-50}$ alkyl, $C_{2-50}$ alkenyl and $C_{2-50}$ alkynyl, which fragment is optionally interrupted by one or more group(s) selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 3- to 10-membered heterocyclyl, phenyl and naphthyl.

In the following sections the term "Hyp$^x$" refers to Hyp$^1$, Hyp$^2$, Hyp$^3$, Hyp$^4$ and Hyp$^5$ collectively.

Preferably, the backbone reagent is a compound of formula (aI), (aII) or (aIII), more preferably the backbone reagent is a compound of formula (aI) or (aIII), and most preferably the backbone reagent is a compound of formula (aI).

In a preferred embodiment, in a compound of formula (aI), x is 4, 6 or 8. Preferably, in a compound of formula (aI) x is 4 or 8, most preferably, x is 4.

In a preferred embodiment in the compounds of the formulas (aI) to (aIV), $A^0$, $A^1$, $A^2$, $A^3$, $A^4$, $A^5$ and $A^6$ are selected from the group comprising

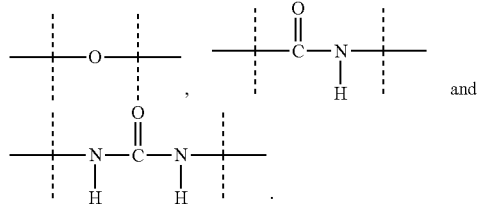

Preferably, in a compound of formula (aI) $A^0$ is

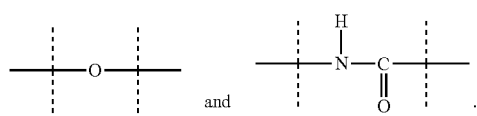

Preferably, in a compound of formula (aI) $A^1$ is

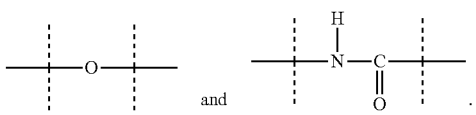

Preferably, in a compound of formula (aI) $A^2$ is

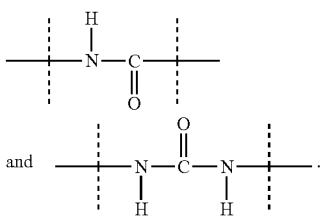

Preferably, in a compound of formula (aII) $A^3$ is

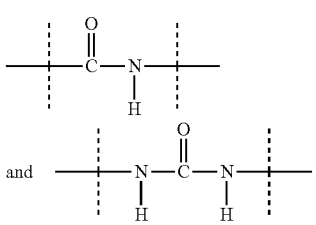

and $A^4$ is

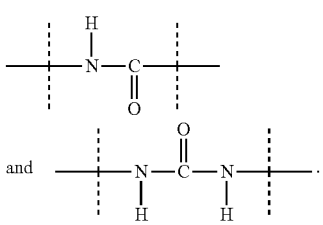

Preferably, in a compound of formula (aII) $A^5$ is

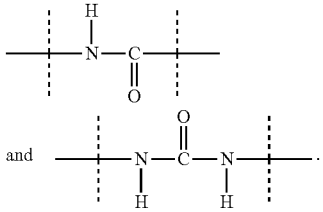

Preferably, in a compound of formula (aIV) $A^6$ is

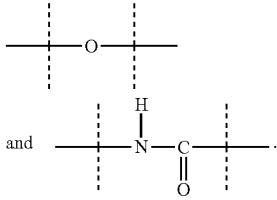

Preferably, in a compound of formula (aIV), $T^1$ is selected from H and $C_{1-6}$ alkyl.
In one embodiment, in a compound of formula (aI), the branching core B is selected from the following structures:
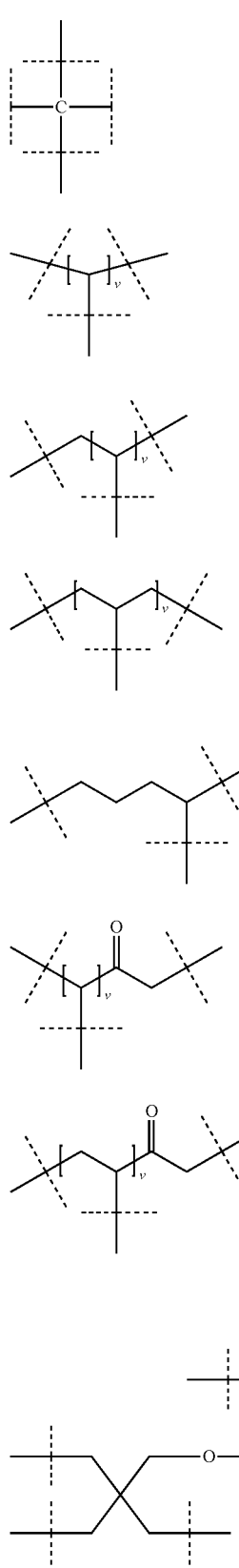
(a-i)
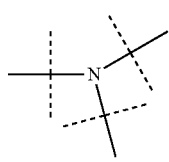
(a-ii)
(a-iii)
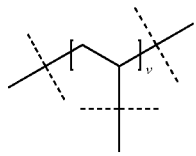
(a-iv)
(a-v)
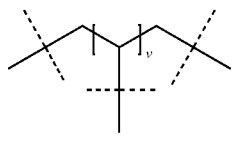
(a-vi)
(a-vii)
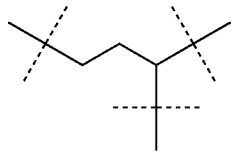
(a-viii)
(a-ix)
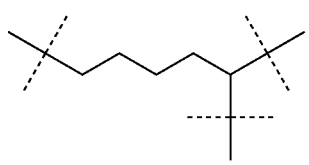
(a-x)
(a-xi)
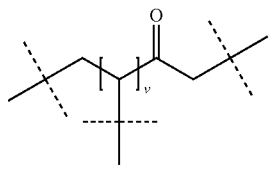
(a-xii)
(a-xiii)
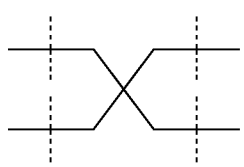
(a-xiv)
(a-xv)
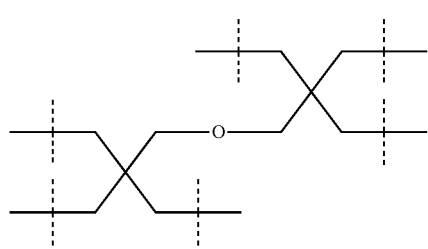

-continued
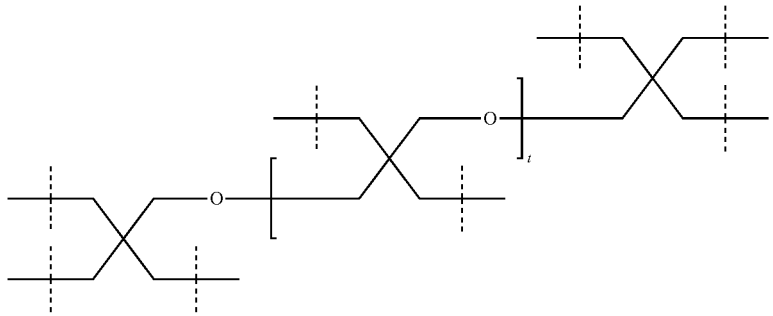
(a-xvi)
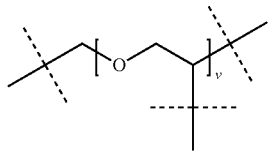
(a-xvii)
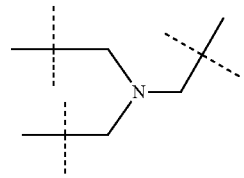
(a-xviii)
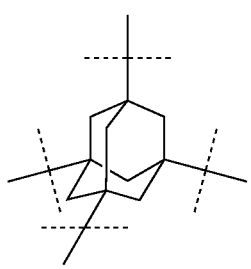
(a-xix)
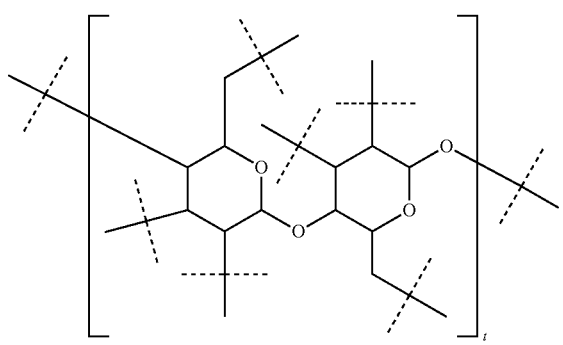
(a-xx)
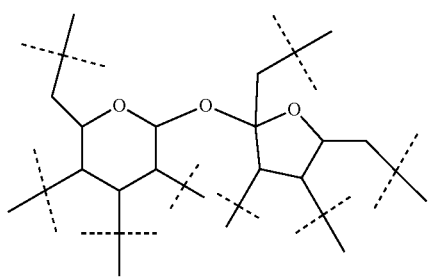
(a-xxi)
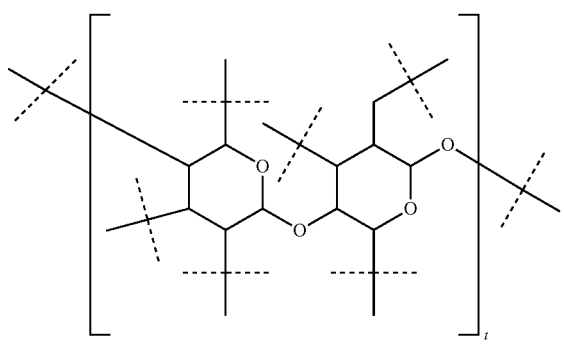
(a-xxii)
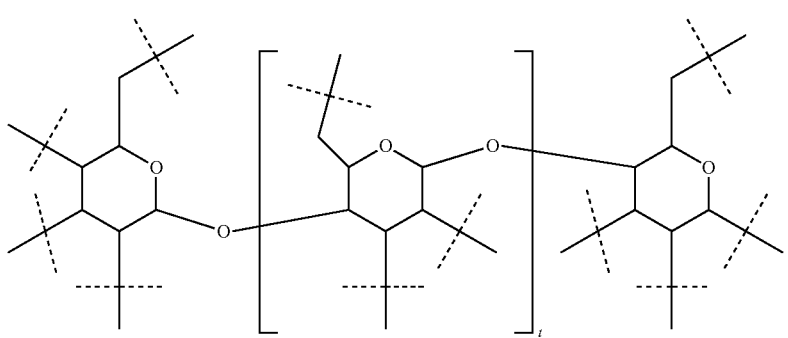
(a-xxiii)

wherein dashed lines indicate attachment to $A^0$ or, if x1 and x2 are both 0, to $A^1$, t is 1 or 2; preferably t is 1, v is 1, 2, 3, 4, 5, 6, 7, 8, 9, 10, 11, 12, 13 or 14; preferably, v is 2, 3, 4, 5, 6;

more preferably, v is 2, 4 or 6; most preferably, v is 2.

In a preferred embodiment, B has a structure of formula (a-i), (a-ii), (a-iii), (a-iv), (a-v), (a-vi), (a-vii), (a-viii), (a-ix), (a-x), (a-xiv), (a-xv) or (a-xvi). More preferably, B has a structure of formula (a-iii), (a-iv), (a-v), (a-vi), (a-vii), (a-viii), (a-ix), (a-x) or (a-iv). Most preferably, B has a structure of formula (a-xiv).

A preferred embodiment is a combination of B and $A^0$, or, if x1 and x2 are both 0 a preferred combination of B and $A^1$, which is selected from the following structures:

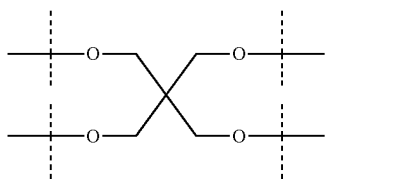
(b-i)

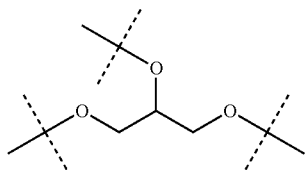
(b-ii)

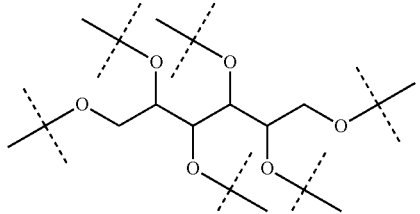
(b-iii)

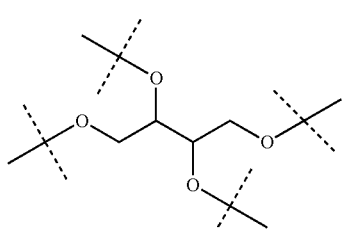
(b-iv)

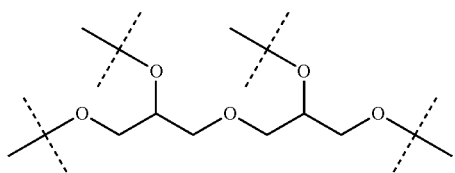
(b-v)

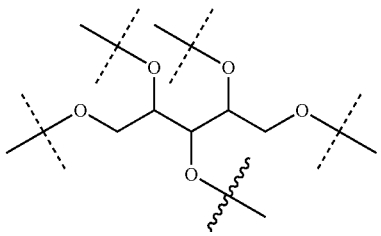
(b-vi)

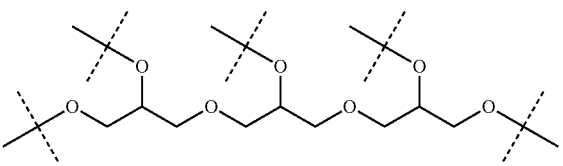
(b-vii)

wherein dashed lines indicate attachment to SP or, if x1 and x2 are both 0, to P.

More preferably, the combination of B and $A^0$ or, if x1 and x2 are both 0, the combination of B and $A^1$, has a structure of formula of formula (b-i), (b-iv), (b-vi) or (b-viii) and most preferably has a structure of formula of formula (b-i).

In one embodiment, x1 and x2 of formula (aI) are 0.

In one embodiment, the PEG-based polymeric chain P has a molecular weight from 0.3 kDa to 40 kDa; e.g. from 0.4 to 35 kDa, from 0.6 to 38 kDA, from 0.8 to 30 kDa, from 1 to 25 kDa, from 1 to 15 kDa or from 1 to 10 kDa. Most preferably P has a molecular weight from 1 to 10 kDa.

In one embodiment, the PEG-based polymeric chain $P^1$ has a molecular weight from 0.3 kDa to 40 kDa; e.g. from 0.4 to 35 kDa, from 0.6 to 38 kDA, from 0.8 to 30 kDa, from 1 to 25 kDa, from 1 to 15 kDa or from 1 to 10 kDa. Most preferably $P^1$ has a molecular weight from 1 to 10 kDa.

In one embodiment, in the compounds of formulas (aI) or (aII), P has the structure of formula (c-i):

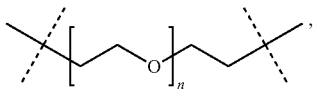
(c-i)

wherein n ranges from 6 to 900, more preferably n ranges from 20 to 700 and most preferably n ranges from 20 to 250.

In one embodiment, in the compounds of formulas (aIII), $P^1$ has the structure of formula (c-ii):

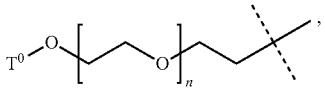
(c-ii)

wherein n ranges from 6 to 900, more preferably n ranges from 20 to 700 and most preferably n ranges from 20 to 250;

$T^0$ is selected from the group comprising $C_{1-6}$ alkyl, $C_{2-6}$ alkenyl and $C_{2-6}$ alkynyl, which is optionally interrupted by one or more group(s) selected from —NH—, —N($C_{1-4}$ alkyl)-, —O—, —S—, —C(O)—, —C(O)NH—, —C(O)N($C_{1-4}$ alkyl)-, —O—C(O)—, —S(O)— and —S(O)$_2$—.

In one embodiment, in the compounds of formulas (aI) to (aIV), the moiety $Hyp^x$ is a polyamine and preferably comprises in bound form and, where applicable, in R- and/or S-configuration a moiety of the formulas (d-i), (d-ii), (d-iii) and/or (d-vi):

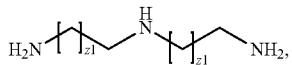
(d-i)

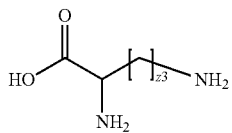
(d-ii)

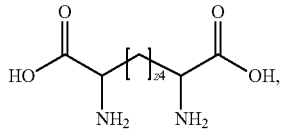
(d-iii)

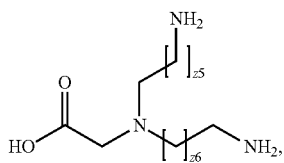
(d-iv)

wherein
z1, z2, z3, z4, z5, z6 are independently of each other 1, 2, 3, 4, 5, 6, 7 or 8.

More preferably, $Hyp^x$ comprises in bound form and in R- and/or S-configuration lysine, ornithine, diaminoproprionic acid and/or diaminobutyric acid. Most preferably, $Hyp^x$ comprises in bound form and in R- and/or S-configuration lysine.

$Hyp^x$ has a molecular weight from 40 Da to 30 kDa, preferably from 0.3 kDa to 25 kDa, more preferably from 0.5 kDa to 20 kDa, even more preferably from 1 kDa to 20 kDa and most preferably from 2 kDa to 15 kDa.

$Hyp^x$ is preferably selected from the group consisting of a moiety of formula (e-i)

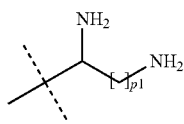
(e-i)

wherein
p1 is an integer from 1 to 5, preferably p1 is 4, and
the dashed line indicates attachment to $A^2$ if the backbone reagent has a structure of (aI) and to $A^3$ or $A^4$ if the backbone reagent has the structure of formula (aII);

a moiety of formula (e-ii)

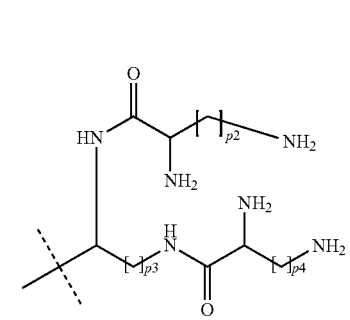
(e-ii)

wherein
p2, p3 and p4 are identical or different and each is independently of the others an integer from 1 to 5, preferably p2, p3 and p4 are 4, and
the dashed line indicates attachment to $A^2$ if the backbone reagent has a structure of formula (aI), to $A^3$ or $A^4$ if the backbone reagent has a structure of formula (aII), to $A^5$ if the backbone reagent has a structure of formula (aII) and to $A^6$ if the backbone reagent has a structure of formula (aIV);

a moiety of formula (e-iii)

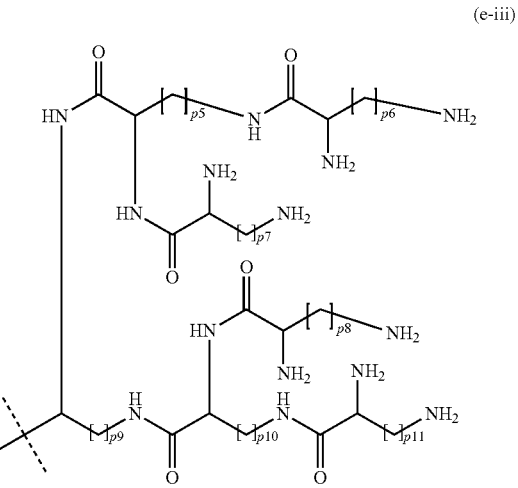
(e-iii)

wherein
p5 to p11 are identical or different and each is independently of the others an integer from 1 to 5, preferably p5 to p11 are 4, and
the dashed line indicates attachment to $A^2$ if the backbone reagent is of formula (aI), to $A^3$ or $A^4$ if the backbone reagent is of formula (aII), to $A^5$ if the backbone reagent is of formula (aIII) and to $A^6$ if the backbone reagent is of formula (aIV);

a moiety of formula (e-iv)

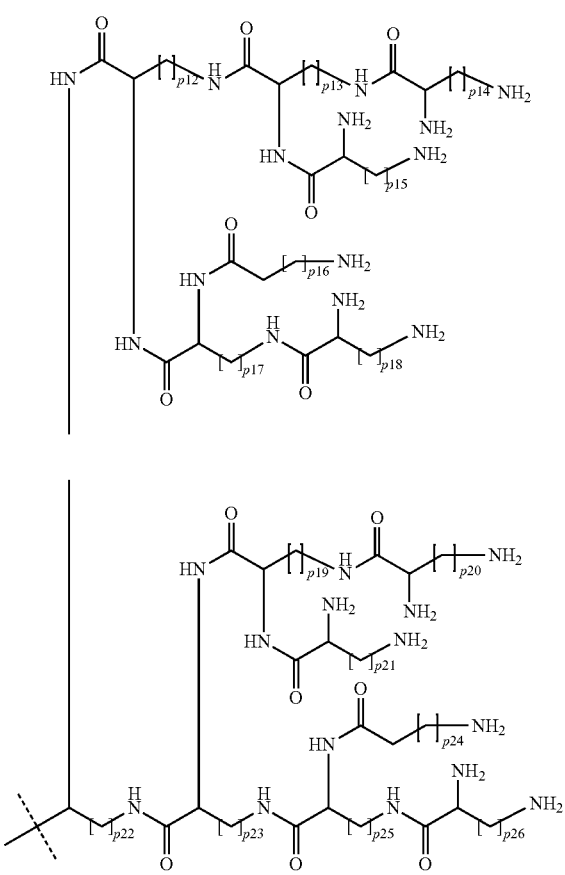

wherein p12 to p26 are identical or different and each is independently of the others an integer from 1 to 5, preferably p12 to p26 are 4, and the dashed line indicates attachment to $A^2$ if the backbone reagent has a structure of formula (aI), to $A^3$ or $A^4$ if the backbone reagent has a structure of formula (aII), to $A^5$ if the backbone reagent has a structure of formula (aIII) and to $A^6$ if the backbone reagent has a structure of formula (aIV);

a moiety of formula (e-v)

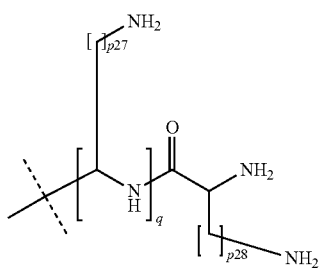

wherein p27 and p28 are identical or different and each is independently of the other an integer from 1 to 5, preferably p27 and p28 are 4, q is an integer from 1 to 8, preferably q is 2 or 6 and most preferably 1 is 6, and the dashed line indicates attachment to $A^2$ if the backbone reagent has a structure of formula (aI), to $A^3$ or $A^4$ if the backbone reagent has a structure of formula (aII), to $A^5$ if the backbone reagent has a structure of formula (aIII) and to $A^6$ if the backbone reagent has a structure of formula (aIV);

a moiety of formula (e-vi)

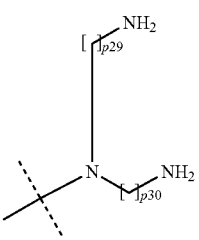

wherein p29 and p30 are identical or different and each is independently of the other an integer from 2 to 5, preferably p29 and p30 are 3, and the dashed line indicates attachment to $A^2$ if the backbone reagent has the structure of formula (aI), to $A^3$ or $A^4$ if the backbone reagent has the structure of formula (aII), to $A^5$ if the backbone reagent has the structure of formula (aIII) and to $A^6$ if the backbone reagent has the structure of formula (aIV);

a moiety of formula (e-vii)

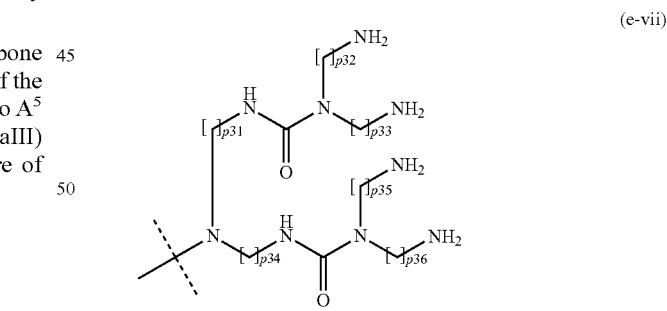

wherein p31 to p36 are identical or different and each is independently of the others an integer from 2 to 5, preferably p31 to p36 are 3, and the dashed line indicates attachment to $A^2$ if the backbone reagent has a structure of formula (aI), to $A^3$ or $A^4$ if the backbone reagent has a structure of formula (aII), to $A^5$ if the backbone reagent has a structure of formula (aIII) and to $A^6$ if the backbone reagent has a structure of formula (aIV);

a moiety of formula (e-viii)

(e-viii)

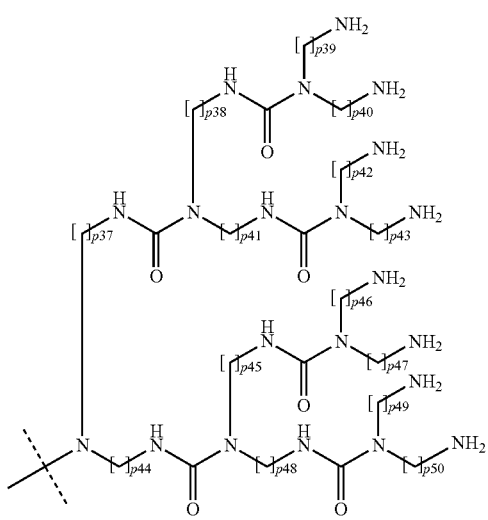

wherein
p37 to p50 are identical or different and each is independently of the others an integer from 2 to 5, preferably p37 to p50 are 3, and
the dashed line indicates attachment to $A^2$ if the backbone reagent has a structure of formula (aI), to $A^3$ or $A^4$ if the backbone reagent has a structure of formula (aII), to $A^5$ if the backbone reagent has a structure of formula (aIII) and to $A^6$ if the backbone reagent has a structure of formula (aIV); and
a moiety of formula (e-ix):

(e-ix)

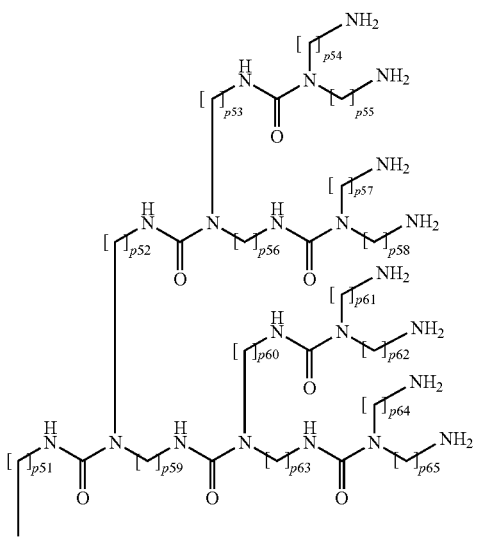

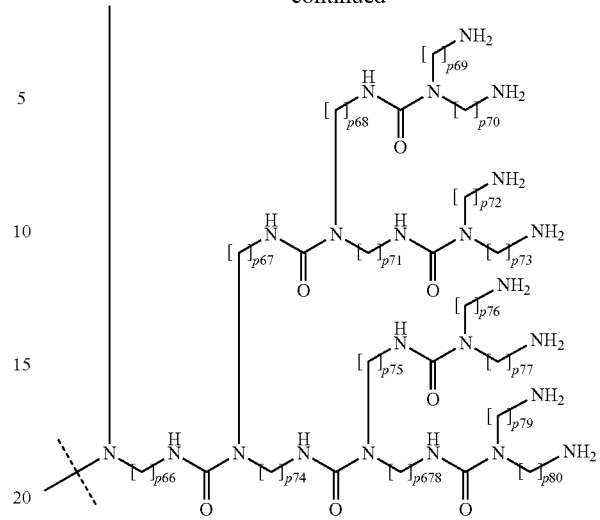

wherein
p51 to p80 are identical or different and each is independently of the others an integer from 2 to 5, preferably p51 to p80 are 3, and
the dashed line indicates attachment to $A^2$ if the backbone reagent has a structure of formula (aI), to $A^3$ or $A^4$ if the backbone reagent has a structure of formula (aII), to $A^5$ if the backbone reagent has a structure of formula (aIII) and to $A^6$ if the backbone reagent has a structure of formula (aIV); and
wherein the moieties (e-i) to (e-v) may at each chiral center be in either R- or S-configuration, preferably, all chiral centers of a moiety (e-i) to (e-v) are in the same configuration.

Preferably, $Hyp^x$ is has a structure of formulas (e-i), (e-ii), (e-iii), (e-iv), (e-vi), (e-vii), (e-viii) or (e-ix). More preferably, $Hyp^x$ has a structure of formulas (e-ii), (e-iii), (e-iv), (e-vii), (e-viii) or (e-ix), even more preferably $Hyp^x$ has a structure of formulas (e-ii), (e-iii), (e-vii) or (e-viii) and most preferably $Hyp^x$ has the structure of formula (e-iii).

If the backbone reagent has a structure of formula (aI), a preferred moiety -$A^2$-$Hyp^1$ is a moiety of the formula

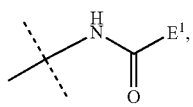

wherein
the dashed line indicates attachment to P; and
$E^1$ is selected from formulas (e-i) to (e-ix).
If the backbone reagent has a structure of formula (aII) a preferred moiety $Hyp^2$-$A^3$- is a moiety of the formula

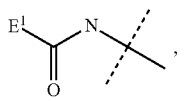

wherein
the dashed line indicates attachment to P; and
$E^1$ is selected from formulas (e-i) to (e-ix);

and a preferred moiety -A⁴-Hyp³ is a moiety of the formula

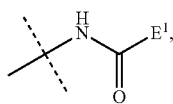

wherein
the dashed line indicates attachment to P; and
E¹ is selected from formulas (e-i) to (e-ix).
If the backbone reagent has a structure of formula (aII), a preferred moiety -A⁵-Hyp⁴ is a moiety of the formula

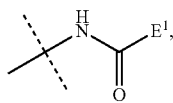

wherein
the dashed line indicates attachment to P¹; and
E¹ is selected from formulas (e-i) to (e-ix).
More preferably, the backbone reagent has a structure of formula (aI) and B has a structure of formula (a-xiv).
Even more preferably, the backbone reagent has the structure of formula (aI), B has the structure of formula (a-xiv), x1 and x2 are 0, and A¹ is —O—.
Even more preferably, the backbone reagent has the structure of formula (aI), B has the structure of formula (a-xiv), A¹ is —O—, and P has a structure of formula (c-i).
Even more preferably, the backbone reagent is formula (aI), B is of formula (a-xiv), x1 and x2 are 0, A¹ is —O—, P is of formula (c-i), A² is —NH—(C=O)— and Hyp¹ is of formula (e-iii).
Most preferably, the backbone reagent has the following formula:

wherein
n ranges from 10 to 40, preferably from 10 to 30, more preferably from 20 to 30 and most preferably n is 28.
SP is a spacer moiety selected from the group comprising $C_{1-6}$ alkyl, $C_{2-6}$ alkenyl and $C_{2-6}$ alkynyl, preferably SP is —CH₂—, —CH₂—CH₂—, —CH(CH₃)—, —CH₂—CH₂—CH₂—, —CH(C₂H₅)—, —C(CH₃)₂—, —CH=CH— and —CH=CH—, most preferably SP is —CH₂—, —CH₂—CH₂— or —CH=CH—.
The at least one crosslinker reagent of step (a-ii) comprises at least one carbonyloxy group (—(C=O)—O— or —O—(C=O)—), which is/are (a) biodegradable linkage(s). Such biodegradable linkage renders the hydrogel biodegradable. Additionally, the at least one crosslinker reagent comprises at least two activated functional end groups which during the polymerization of step (b) react with the functional groups $A^{x0}$ of the at least one backbone reagent.
The crosslinker reagent has a molecular weight ranging from 0.5 to 40 kDa, more preferably ranging from 0.75 to 30 kDa, even more preferably ranging from 1 to 20 kDa, even more preferably ranging from 1 to 10 kDa, even more preferably ranging from 1 to 7.5 kDa and most preferably ranging from 2 kDa to 4 kDa.
The crosslinker reagent comprises at least two activated functional end groups selected from the group comprising activated ester groups, activated carbamate groups, activated carbonate groups and activated thiocarbonate groups, which during polymerization react with the amine groups of the backbone reagents, forming amide linkages.
In one preferred embodiment, the crosslinker reagent is a compound of formula (V-I):

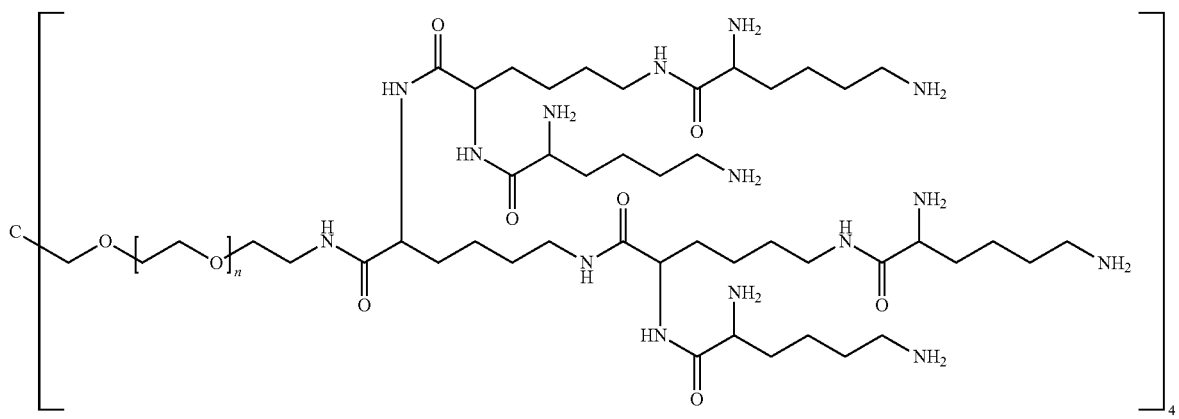

(V-I)

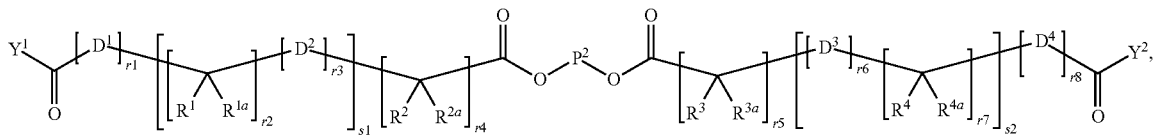

wherein each $D^1$, $D^2$, $D^3$ and $D^4$ are identical or different and each is independently of the others selected from the group comprising —O—, —$NR^5$—, —S— and —$CR^6R^{6a}$—;

each $R^1$, $R^{1a}$, $R^2$, $R^{2a}$, $R^3$, $R^{3a}$, $R^4$, $R^{4a}$, $R^6$ and $R^{6a}$ are identical or different and each is independently of the others selected from the group comprising —H, —$OR^7$, —$NR^7R^{7a}$, —$SR^7$ and $C_{1-6}$ alkyl; optionally, each of the pair(s) $R^1/R^2$, $R^3/R^4$, $R^{1a}/R^{2a}$, and $R^{3a}/R^{4a}$ may independently form a chemical bond and/or each of the pairs $R^1/R^{1a}$, $R^2/R^{2a}$, $R^3/R^{3a}$, $R^4/R^{4a}$, $R^6/R^{6a}$, $R^1/R^2$, $R^3/R^4$, $R^{1a}/R^{2a}$, and $R^{3a}/R^{4a}$ are independently of each other joined together with the atoms to which they are attached to form a $C_{3-8}$ cycloalkyl or to form a ring A or are joined together with the atoms to which they are attached to form a 3- to 10-membered heterocyclyl or 8- to 11-membered heterobicyclyl or adamantyl;

each $R^5$ is independently selected from —H and $C_{1-6}$ alkyl; optionally, each of the pair(s) $R^1/R^5$, $R^2/R^5$, $R^3/R^5$, $R^4/R^5$ and $R^5/R^6$ may independently form a chemical bond and/or are joined together with the atoms to which they are attached to form a 3- to 10-membered heterocyclyl or 8- to 11-membered heterobicyclyl;

each $R^7$, $R^{7a}$ is independently selected from H and $C_{1-6}$ alkyl;

A is selected from the group consisting of indenyl, indanyl and tetralinyl;

$P^2$ is

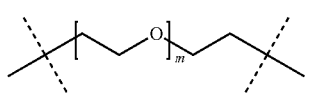

m ranges from 120 to 920, preferably from 120 to 460 and more preferably from 120 to 230, r1, r2, r7, r8 are independently 0 or 1;

r3, r6 are independently 0, 1, 2, 3, or 4;

r4, r5 are independently 1, 2, 3, 4, 5, 6, 7, 8, 9 or 10;

s1, s2 are independently 1, 2, 3, 4, 5 or 6;

$Y^1$, $Y^2$ are identical or different and each is independently of the other selected from formulas (f-i) to (f-vii):

(f-i)

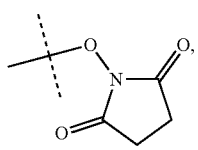

(f-ii)

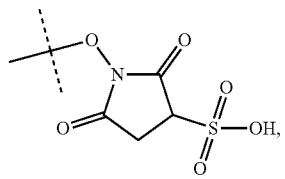

(f-iii)

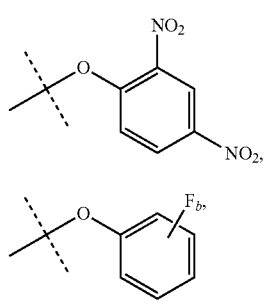

(f-iv)

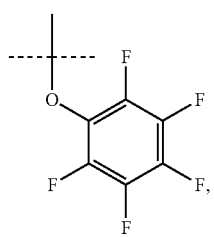

(f-v)

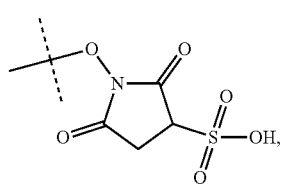

(f-vi)

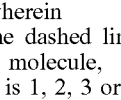

(f-vii)

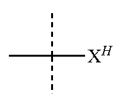

wherein
the dashed lines indicate attachment to the rest of the molecule,
b is 1, 2, 3 or 4
$X^H$ is Cl, Br, I, or F.

Preferably, the crosslinker reagent is a compound of formula (V-II):

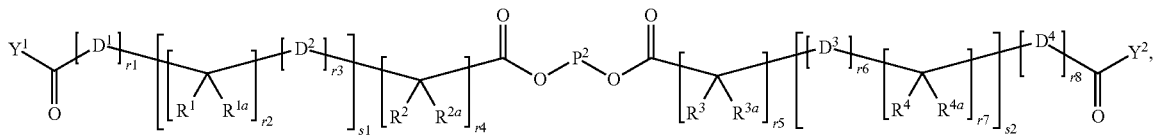
(V-II)

wherein
$D^1$, $D^2$, $D^3$ and $D^4$ are identical or different and each is independently of the others selected from the group comprising O, $NR^5$, S and $CR^5R^{5a}$; $R^1$, $R^{1a}$, $R^2$, $R^{2a}$, $R^3$, $R^{3a}$, $R^4$, $R^{4a}$, $R^5$ and $R^{5a}$ are identical or different and each is independently of the others selected from the group comprising H and $C_{1-6}$ alkyl; optionally, one or more of the pair(s) $R^1/R^{1a}$, $R^2/R^{2a}$, $R^3/R^{3a}$, $R^4/R^{4a}$, $R^1/R^2$, $R^3/R^4$, $R^{1a}/R^{2a}$, and $R^{3a}/R^{4a}$ form a chemical bond or are joined together with the atom to which they are attached to form a $C_{3-8}$ cycloalkyl or to form a ring A or are joined together with the atom to which they are attached to form a 3- to 10-membered heterocyclyl or 8- to 11-membered heterobicyclyl or adamantyl;

A is selected from the group consisting of phenyl, naphthyl, indenyl, indanyl and tetralinyl;

$P^2$ is

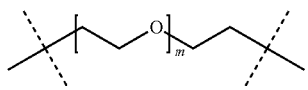

m ranges from 11 to 908, preferably from 17 to 680, even more preferably from 22 to 454, even more preferably from 22 to 227, even more preferably from 22 to 170 and more preferably from 45 to 90;

r1, r2, r7, r8 are independently 0 or 1;
r3, r6 are independently 0, 1, 2, 3, or 4;
r4, r5 are independently 1, 2, 3, 4, 5, 6, 7, 8, 9 or 10;
s1, s2 are independently 1, 2, 3, 4, 5 or 6;
$Y^1$, $Y^2$ are identical or different and each is independently of the other selected from formulas (f-i) to (f-vii):

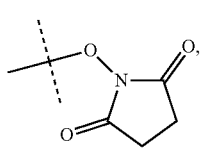
(f-i)

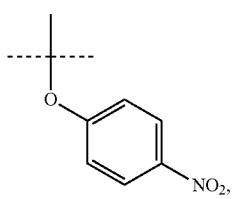
(f-ii)

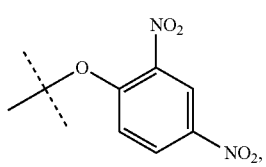
(f-iii)

-continued

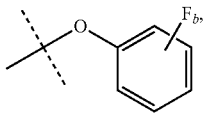
(f-iv)

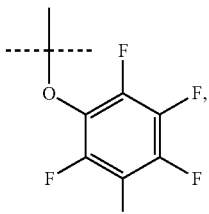
(f-v)

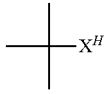
(f-vi)

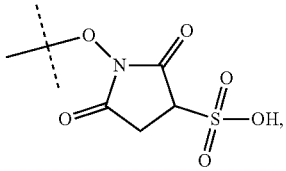
(f-vii)

wherein
the dashed lines indicate attachment to the rest of the molecule,
b is 1, 2, 3 or 4
$X^H$ is Cl, Br, I, or F.
It is understood that the moieties

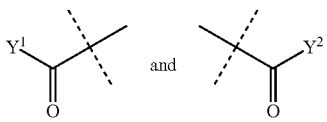

represent the at least two activated functional end groups.

Preferably, $Y^1$ and $Y^2$ of formula (V-I) or (V-II) have a structure of formula (f-i), (f-ii) or (f-v). More preferably, $Y^1$ and $Y^2$ of formula (V-I) or (V-II) have a structure of formula (f-i) or (f-ii) and most preferably, $Y^1$ and $Y^2$ have a structure of formula (f-i).

Preferably, both moieties $Y^1$ and $Y^2$ of formula (V-I) or (V-II) have the same structure. More preferably, both moieties $Y^1$ and $Y^2$ have the structure of formula (f-i).

Preferably, r1 of formula (V-I) or (V-II) is 0.
Preferably, r1 and s1 of formula (V-I) or (V-II) are both 0.
Preferably, one or more of the pair(s) $R^1/R^{1a}$, $R^2/R^{2a}$, $R^3/R^{3a}$, $R^4/R^{4a}$, $R^1/R^2$, $R^3/R^4$, $R^{1a}/R^{2a}$, and $R^{3a}/R^{4a}$ of formula (V-I) or (V-II) form a chemical bond or are joined together with the atom to which they are attached to form a C$_{3-8}$ cycloalkyl or form a ring A.

Preferably, one or more of the pair(s) R$^1$/R$^2$, R$^{1a}$/R$^{2a}$, R$^3$/R$^4$, R$^{3a}$/R$^{4a}$ of formula (V-I) or (V-II) are joined together with the atoms to which they are attached to form a 3- to 10-membered heterocyclyl or 8- to 11-membered heterobicyclyl.

Preferably, the crosslinker reagent of formula (V-I) and (V-II) is symmetric, i.e. the moiety

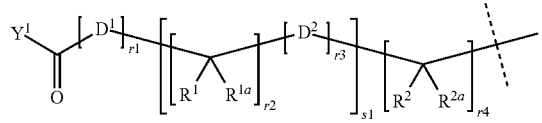

has the same structure as the moiety

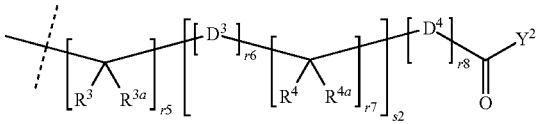

In one preferred embodiment s1, s2, r1 and r8 of formula (V-I) and (V-II) are 0.

In another preferred embodiment s1, s2, r1 and r8 of formula (V-I) and (V-II) are 0 and r4 of formula (V-I) and (V-II) and r5 are 1.

Preferred crosslinker reagents are of formula (V-1) to (V-54):

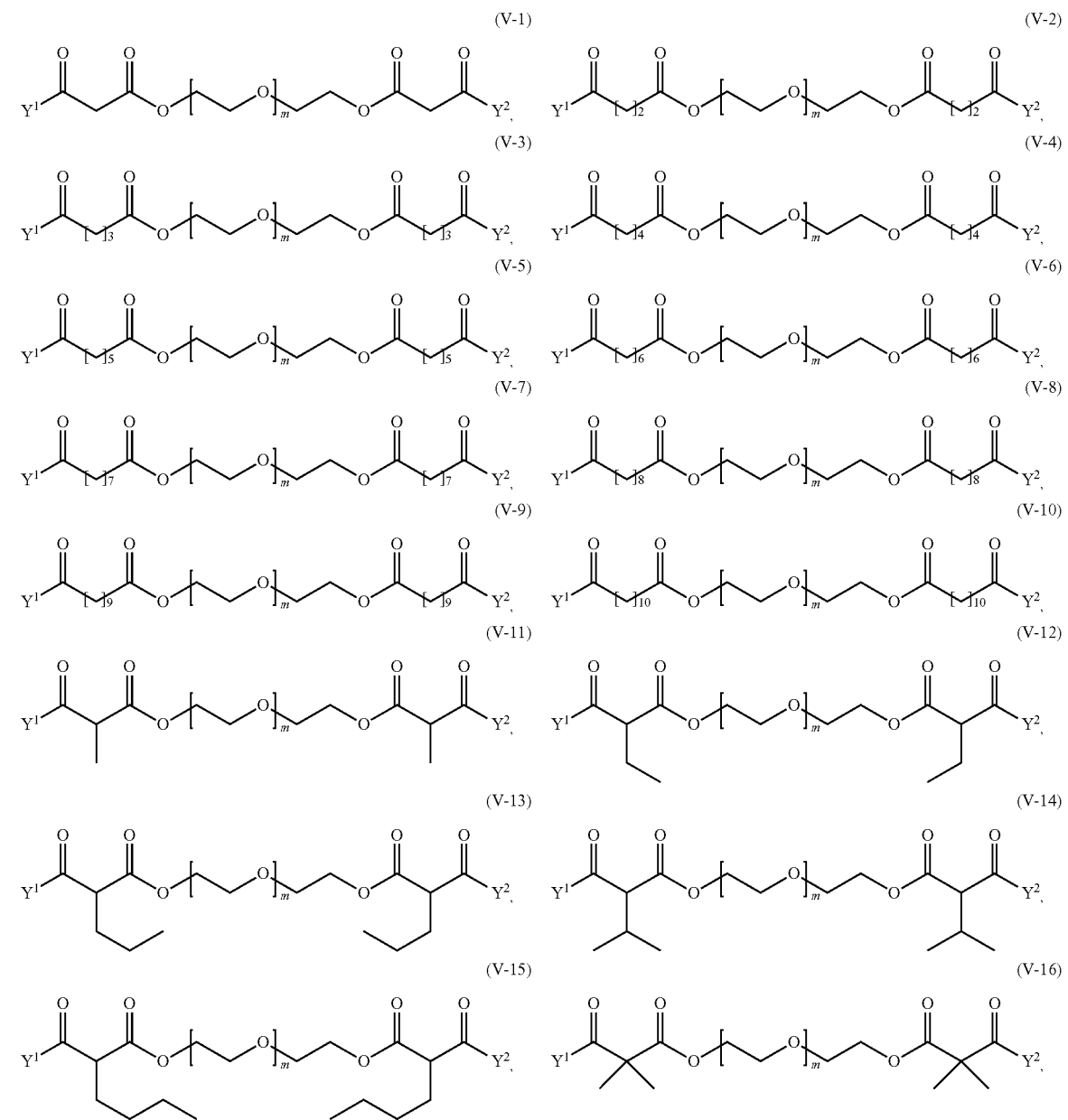

(V-17) 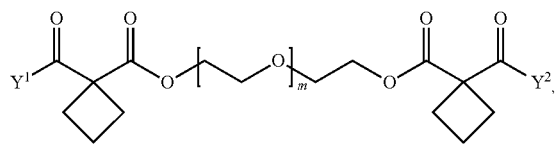
(V-18) 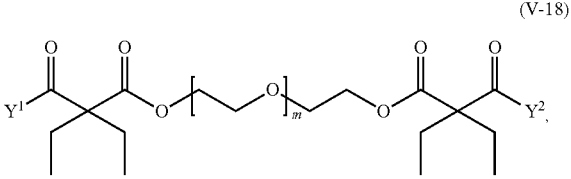
(V-19) 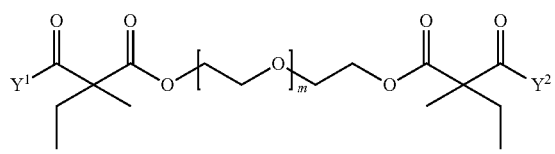
(V-20) 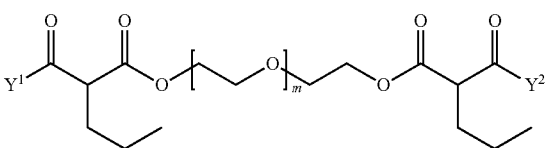
(V-21) 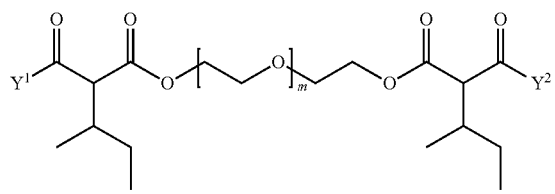
(V-22) 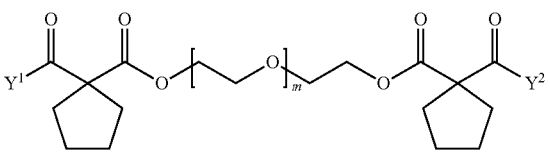
(V-23) 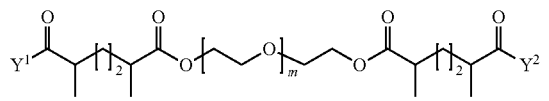
(V-24) 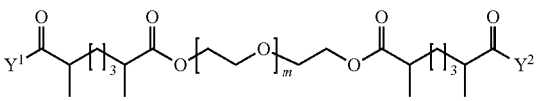
(V-25) 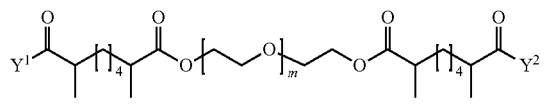
(V-26) 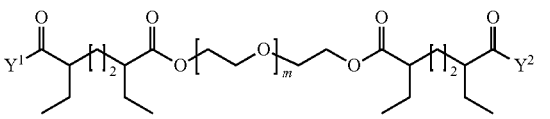
(V-27) 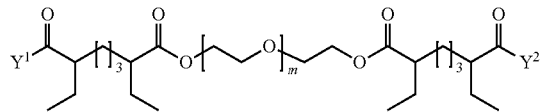
(V-28) 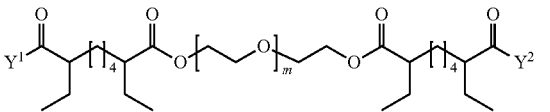
(V-29) 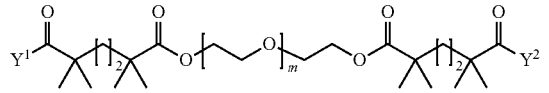
(V-30) 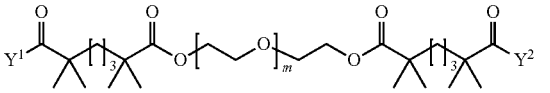
(V-31) 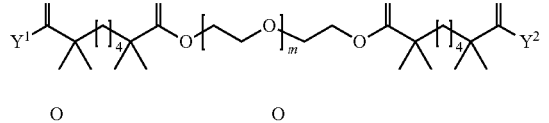

-continued
(V-34)
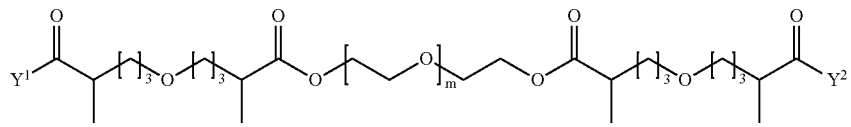
(V-35)
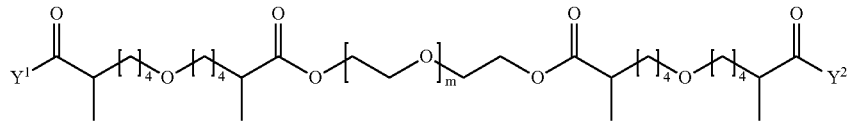
(V-36) (V-37)
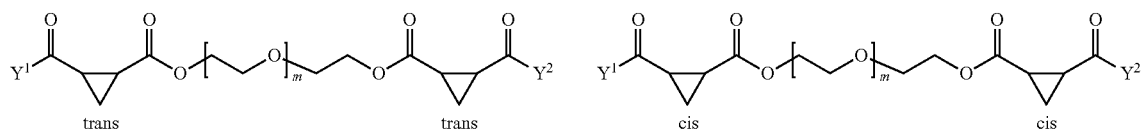
(V-38) (V-39)
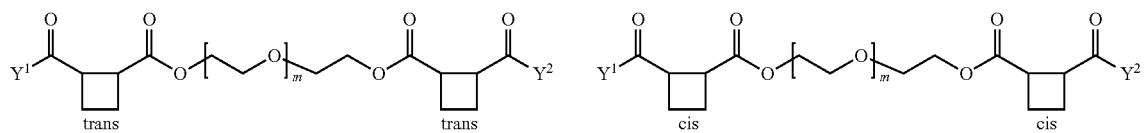
(V-40) (V-41)
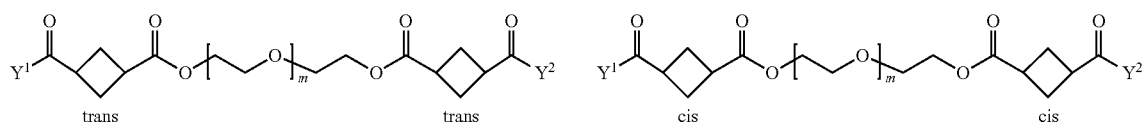
(V-42) (V-43)
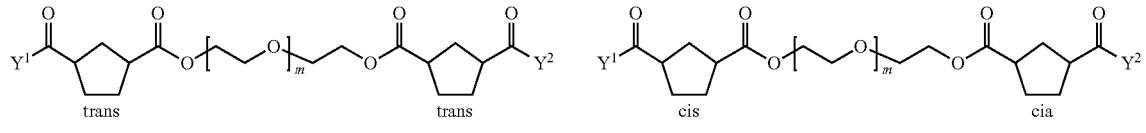
(V-44) (V-45)
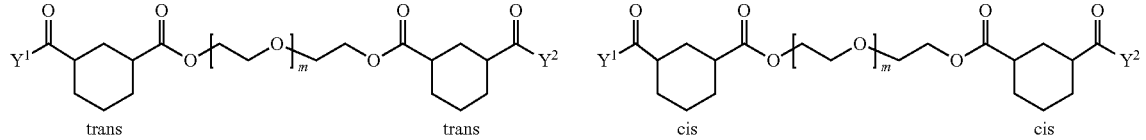
(V-46) (V-47)
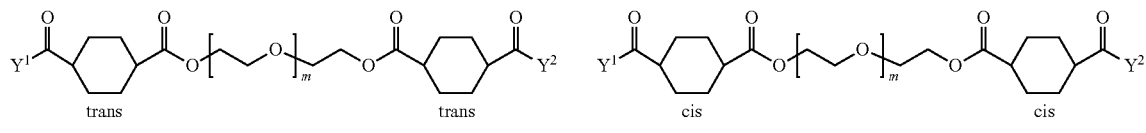
(V-48)
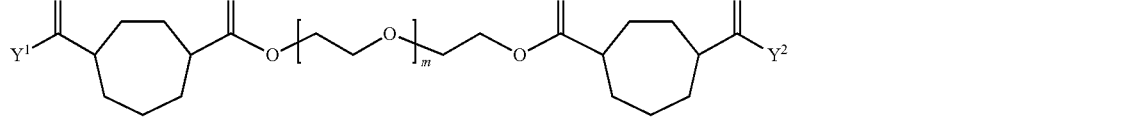
(V-49)
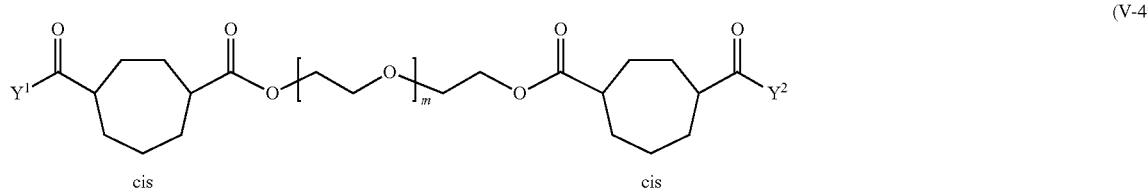

-continued

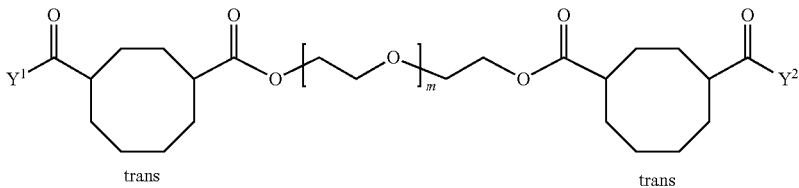
(V-50)

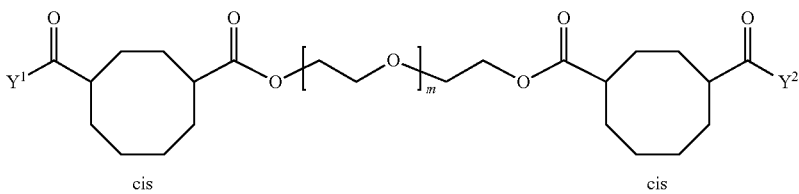
(V-51)

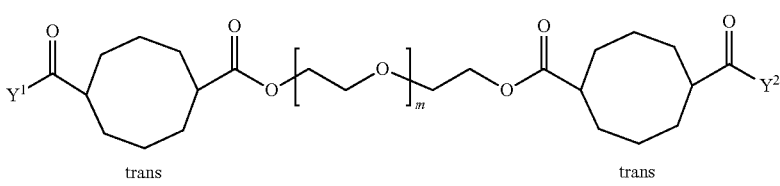
(V-52)

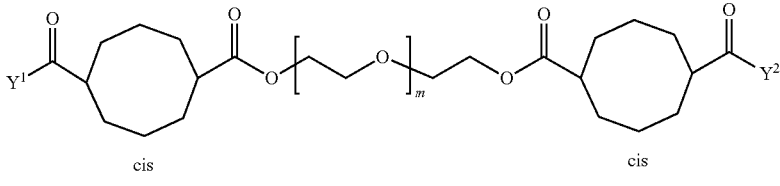
(V-53)

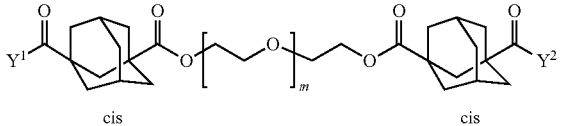
(V-54)

wherein
each crosslinker reagent may be in the form of its racemic mixture, where applicable; and m, $Y^1$ and $Y^2$ are defined as above.

Crosslinker reagents V-11 to V-54, V-1 and V-2 are preferred crosslinker reagents.

Crosslinker reagents Va-11 to Va-54, Va-1 and Va-2 are most preferred crosslinker reagents. Most preferred is crosslinker reagent Va-14.

In another embodiment, crosslinker reagents V-1, V-2, V-5, V-6, V-7, V-8, V-9, V-10, V-11, V-12, V-13, V-14, V-15, V-16, V-17, V-18, V-19, V-20, V-21, V-22, V-23, V-24, V-25, V-26, V-27, V-28, V-29, V-30, V-31, V-32, V-33, V-34, V-35, V-36, V-37, V-38, V-39, V-40, V-41, V-42, V-43, V-44, V-45, V-46, V-47, V-48, V-49, V-50, V-51, V-52, V-53 an V-54 are preferred crosslinker reagents. More preferably, the at least one crosslinker reagent is of formula V-5, V-6, V-7, V-8, V-9, V-10, V-14, V-22, V-23, V-43, V-44, V-45 or V-46, and most preferably, the at least one crosslinker reagent is of formula V-5, V-6, V-9 or V-14.

The preferred embodiments of the compound of formula (V-I) and (V-II) as mentioned above apply accordingly to the preferred compounds of formulas (V-1) to (V-53).

In a preferred embodiment, the hydrogel comprises $A^{x0}$ in the form of primary or secondary amine functional groups. Preferably, such hydrogel contains from 0.01 to 1 mmol/g primary amine groups (—$NH_2$), more preferably, from 0.02 to 0.5 mmol/g primary amine groups and most preferably from 0.05 to 0.3 mmol/g primary amine groups. The term "X mmol/g primary amine groups" means that 1 g of dry hydrogel comprises X mmol primary amine groups. Measurement of the amine content of the hydrogel is carried out according to Gude et al. (Letters in Peptide Science, 2002, 9(4): 203-206, which is incorporated by reference in its entirety).

Preferably, the term "dry" as used herein means having a residual water content of a maximum of 10%, preferably less than 5% and more preferably less than 2% (determined according to Karl Fischer). The preferred method of drying is lyophilization.

It is understood that the hydrogel may be modified by conjugating certain moieties other than $L^1$ to remaining functional groups $A^{x0}$, such as for example spacer moieties and/or polymers and that also such modified hydrogel may be one embodiment of Z.

In a preferred embodiment -Z is a hydrogel obtainable from the process for the preparation of a hydrogel as detailed above which is optionally modified by conjugating a spacer moiety-fatty acid or polymer moiety conjugate —$SP^0$-$Z^0$ to remaining functional groups $A^{x0}$.

Such spacer moiety —$SP^0$— is preferably selected from the group consisting of -T-, —C(O)O—, —O—, —C(O)—, —C(O)N($R^{z1}$)—, —S(O)$_2$N($R^{z1}$)—, —S(O)N($R^{z1}$)—, —S(O)$_2$—, —S(O)—, —N($R^{z1}$)S(O)$_2$N($R^{z1a}$)—, —S—, —N($R^{z1}$)—, —OC(O$R^{z1}$)($R^{z1a}$)—, —N($R^{z1}$)C(O)N($R^{z1a}$)—, —OC(O)N($R^{z1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{z2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{z3}$)—, —S(O)$_2$N($R^{z3}$)—, —S(O)N($R^{z3}$)—, —S(O)$_2$—, —S(O)—, —N($R^{z3}$)S(O)$_2$N($R^{z3}$a), —S—, —N($R^{z3}$)—, —OC(O$R^{z3}$)($R^{z3a}$)—, —N($R^{z3}$)C(O)N($R^{z3a}$)—, and —OC(O)N($R^{z3}$)—;

—$R^{z1}$ and —$R^{z1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more —$R^{z2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{z4}$)—, —S(O)$_2$N($R^{z4}$)—, —S(O)N($R^{z4}$)—, —S(O)$_2$—, —S(O)—, —N($R^{z4}$)S(O)$_2$N($R^{z4a}$)—, —S—, —N($R^{z4}$)—, —OC(O$R^{z4}$)($R^{z4a}$)—, —N($R^{z4}$)C(O)N($R^{z4a}$)—, and —OC(O)N($R^{z4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{z2}$, which are the same or different;

each —$R^{z2}$ is independently selected from the group consisting of halogen, —CN, oxo (=O), —COO$R^{z5}$, —O$R^5$, —C(O)$R^{z5}$, —C(O)N($R^{z5}R^{z5a}$), —S(O)$_2$N($R^{z5}R^{z5a}$), —S(O)N($R^{z5}R^{z5a}$), —S(O)$_2R^{z5}$, —S(O)$R^{z5}$, —N($R^{z5}$)S(O)$_2$N($R^{z5a}R^{z5b}$), —S$R^{z5}$, —N($R^{z5}R^{z5a}$), —NO$_2$, —OC(O)$R^{z5}$, —N($R^{z5}$)C(O)$R^{z5a}$, —N($R^{z5}$)S(O)$_2R^{z5a}$, —N($R^{z5}$)S(O)$R^{z5a}$, —N($R^{z5}$)C(O)O$R^{z5a}$, —N($R^{z5}$)C(O)N($R^{z5a}R^{z5b}$), —OC(O)N($R^{z5}R^{z5a}$), and $C_{1-6}$ alkyl; wherein $C_{1-6}$ alkyl is optionally substituted with one or more halogen, which are the same or different;

each —$R^{z3}$, —$R^{z3a}$, —$R^{z4}$, —$R^{z4a}$, —$R^{z5}$, —$R^{z5a}$ and —$R^{z5b}$ is independently selected from the group consisting of —H, and $C_{1-6}$ alkyl; wherein $C_{1-6}$ alkyl is optionally substituted with one or more halogen, which are the same or different.

In one embodiment -$Z^0$ comprises a $C_{8-18}$ alkyl group.

In another embodiment -$Z^0$ comprises a water-soluble polymer with a molecular weight of at least 0.5 kDa.

Preferably, -$Z^0$ comprises at least one of the polymers selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropyl-methacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In a preferred embodiment the poly(amide) is a peptide or protein.

In another preferred embodiment -$Z^0$ comprises a PEG-based polymer comprising at last 10% PEG, such as at least 20% PEG, at least 30% PEG, at least 40% PEG or at least 50% PEG; or a hyaluronic acid-based polymer comprising at least 10% hyaluronic acid, such as at least 20% hyaluronic acid, at least 30% hyaluronic acid, at least 40% hyaluronic acid or at least 50% hyaluronic acid.

In the prodrugs, their pharmaceutically acceptable salts and the prodrug reagents of the present invention -$L^2$- and -$L^{2'}$- of formula (I) and (I') are independently of each other a chemical bond or a spacer moiety.

When -$L^2$- and -$L^{2'}$- are other than a single chemical bond, -$L^2$- and -$L^{2'}$- are preferably independently of each other selected from the group consisting of -T-, —C(O)O—, —O—, —C(O)—, —C(O)N($R^{y1}$)—, —S(O)$_2$N($R^{y1}$)—, —S(O)N($R^{y1}$)—, —S(O)$_2$—, —S(O)—, —N($R^{y1}$)S(O)$_2$N($R^{y1a}$)—, —S—, —N($R^{y1}$)—, —OC(O$R^{y1}$)($R^{y1a}$)—, —N($R^{y1}$)C(O)N($R^{y1a}$)—, —OC(O)N($R^{y1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—, —OC(O$R^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more —$R^{y2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y4}$)—, —S(O)$_2$N($R^{y4}$)—, —S(O)N($R^{y4}$)—, —S(O)$_2$—, —S(O)—, —N($R^{y4}$)S(O)$_2$N($R^{y4a}$)—, —S—, —N($R^{y4}$)—, —OC(O$R^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

each —$R^{y2}$ is independently selected from the group consisting of halogen, —CN, oxo (=O), —COO$R^5$, —O$R^{y5}$, —C(O)$R^{y5}$, —C(O)N($R^5R^{y5a}$), —S(O)$_2$N($R^{y5}R^{y5a}$), —S(O)N($R^{y5}R^{y5a}$), —S(O)$_2R^{y5}$, —S(O)$R^{y5}$, —N($R^{y5}$)S(O)$_2$N($R^{y5a}R^{y5b}$), —S$R^{y5}$, —N($R^{y5}R^{y5a}$), —NO$_2$, —OC(O)R$^{y5}$, —N(R$^{y5}$) C(O)R$^{y5a}$, —N(R$^{y5}$)S(O)$_2$R$^{y5a}$, —N(R$^{y5}$)S(O)R$^{y5a}$, —N(R$^{y5}$)C(O)OR$^{y5a}$, —N(R$^{y5}$)C(O)N(R$^{y5a}$R$^{y5b}$), —OC(O)N(R$^{y5}$R$^{y5a}$), and C$_{1-6}$ alkyl; wherein C$_{1-6}$ alkyl is optionally substituted with one or more halogen, which are the same or different; and each —R$^{y3}$, —R$^{y3a}$, —R$^{y4}$, —R$^{y4a}$, —R$^{y5}$, —R$^{y5a}$ and —R$^{y5b}$ is independently selected from the group consisting of —H, and C$_{1-6}$ alkyl, wherein C$_{1-6}$ alkyl is optionally substituted with one or more halogen, which are the same or different.

When -L$^2$- and -L$^{2'}$- are other than a single chemical bond, -L$^2$- and -L$^{2'}$- are even more preferably independently of each other selected from -T-, —C(O)O—, —O—, —C(O)—, —C(O)N(R$^{y1}$)—, —S(O)$_2$N(R)—, —S(O)N(R')—, —S(O)$_2$—, —S(O)—, —N(R$^{y1}$)S(O)$_2$N(R$^{y1a}$)—, —S—, —N(R$^{y1}$)—, —OC(OR$^{y1}$)(R$^{y1a}$)—, —N(R$^{y1}$)C(O)N(R$^{y1a}$)—, —OC(O)N(R$^{y1}$)—, C$_{1-50}$ alkyl, C$_{2-50}$ alkenyl, and C$_{2-50}$ alkynyl; wherein -T-, C$_{1-20}$ alkyl, C$_{2-20}$ alkenyl, and C$_{2-20}$ alkynyl are optionally substituted with one or more —R$^{y2}$, which are the same or different and wherein C$_{1-20}$ alkyl, C$_{2-20}$ alkenyl, and C$_{2-20}$ alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^3$)—;

—R$^{y1}$ and —R$^{y1a}$ are independently of each other selected from the group consisting of —H, -T, C$_{1-10}$ alkyl, C$_{2-10}$ alkenyl, and C$_{2-10}$ alkynyl; wherein -T, C$_{1-10}$ alkyl, C$_{2-10}$ alkenyl, and C$_{2-10}$ alkynyl are optionally substituted with one or more —R$^{y2}$, which are the same or different, and wherein C$_{1-10}$ alkyl, C$_{2-10}$ alkenyl, and C$_{2-10}$ alkynyl are optionally interrupted by one or more groups selected from the group consisting of -T-, —C(O)O—, —O—, —C(O)—, —C(O)N(R$^{y4}$)—, —S(O)$_2$N(R$^{y4}$)—, —S(O)N(R$^{y4}$)—, —S(O)$_2$—, —S(O)—, —N(R$^{y4}$)S(O)$_2$N(R$^{y4a}$)—, —S—, —N(R$^{y4}$)—, —OC(OR$^{y4}$)(R$^{y4a}$)—, —N(R$^{y4}$)C(O)N(R$^{y4a}$)—, and —OC(O)N(R$^{y4}$)—;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —R$^{y2}$, which are the same or different;

—R$^{y2}$ is selected from the group consisting of halogen, —CN, oxo (=O), —COOR$^5$, —OR$^{y5}$, —C(O)R$^{y5}$, —C(O)N(R$^{y5}$R$^{y5a}$), —S(O)$_2$N(R$^{y5}$R$^{y5a}$), —S(O)N(R$^{y5}$R$^{y5a}$), —S(O)$_2$R$^{y5}$, —S(O)R$^{y5}$, —N(R$^{y5}$)S(O)$_2$N(R$^{y5a}$R$^{y5b}$), —SR$^{y5}$, —N(R$^{y5}$R$^{y5a}$), —NO$_2$, —OC(O)R$^{y5}$, —N(R$^{y5}$)C(O)R$^{y5a}$, —N(R$^{y5}$)S(O)$_2$R$^{y5a}$, —N(R$^{y5}$)S(O)R$^{y5a}$, —N(R$^{y5}$)C(O)OR$^{y5a}$, —N(R$^{y5}$)C(O)N(R$^{y5a}$R$^{y5b}$), —OC(O)N(R$^{y5}$R$^{y5a}$), and C$_{1-6}$ alkyl; wherein C$_{1-6}$ alkyl is optionally substituted with one or more halogen, which are the same or different; and each —R$^{y3}$, —R$^{y3a}$, —R$^{y4}$, —R$^{y4a}$, —R$^{y5}$, —R$^{y5a}$ and —R$^{y5b}$ is independently of each other selected from the group consisting of —H, and C$_{1-6}$ alkyl; wherein C$_{1-6}$ alkyl is optionally substituted with one or more halogen, which are the same or different.

When -L$^2$- and -L$^{2'}$- are other than a single chemical bond, -L$^2$- and -L$^{2'}$- are even more preferably independently of each other selected from the group consisting of -T-, —C(O)O—, —O—, —C(O)—, —C(O)N(R$^{y1}$)—, —S(O)$_2$N(R$^{y1}$)—, —S(O)N(R$^{y1}$)—, —S(O)$_2$—, —S(O)—, —N(R$^{y1}$)S(O)$_2$N(R$^{y1a}$)—, —S—, —N(R$^{y1}$)—, —OC(OR$^{y1}$)(R$^{y1a}$)—, —N(R$^{y1}$)C(O)N(R$^{y1a}$)—, —OC(O)N(R$^{y1}$)—, C$_{1-50}$ alkyl, C$_{2-50}$ alkenyl, and C$_{2-50}$ alkynyl; wherein -T-, C$_{1-20}$ alkyl, C$_{2-20}$ alkenyl, and C$_{2-20}$ alkynyl are optionally substituted with one or more —R$^{y2}$, which are the same or different and wherein C$_{1-20}$ alkyl, C$_{2-20}$ alkenyl, and C$_{2-20}$ alkynyl are optionally interrupted by one or more groups selected from the group consisting of -T-, —C(O)O—, —O—, —C(O)—, —C(O)N(R$^{y3}$)—, —S(O)$_2$N(R$^{y3}$)—, —S(O)N(R$^{y3}$)—, —S(O)$_2$—, —S(O)—, —N(R$^{y3}$)S(O)$_2$N(R$^{y3a}$)—, —S—, —N(R$^{y3}$)—, —OC(OR$^{y3}$)(R$^{y3a}$)—, —N(R$^{y3}$)C(O)N(R$^{y3a}$)—, and —OC(O)N(R$^{y3}$)—;

—R$^{y1}$ and —R$^{y1a}$ are independently selected from the group consisting of —H, -T, C$_{1-10}$ alkyl, C$_{2-10}$ alkenyl, and C$_{2-10}$ alkynyl;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each —R$^{y2}$ is independently selected from the group consisting of halogen, and C$_{1-6}$ alkyl; and each —R$^{y3}$, —R$^{y3a}$, —R$^{y4}$, —R$^{y4a}$, —R$^{y5}$, —R$^{y5a}$ and —R$^{y5b}$ is independently of each other selected from the group consisting of —H, and C$_{1-6}$ alkyl; wherein C$_{1-6}$ alkyl is optionally substituted with one or more halogen, which are the same or different.

Even more preferably, -L$^2$- and -L$^{2'}$- are a C$_{1-20}$ alkyl chain, which is optionally interrupted by one or more groups independently selected from —O—, -T- and —C(O)N(R$^{1aa}$)—; and which C$_{1-20}$ alkyl chain is optionally substituted with one or more groups independently selected from —OH, -T and —C(O)N(R$^{y6}$R$^{y6a}$); wherein —R$^{y6}$, —R$^{y6a}$ are independently selected from the group consisting of H and C$_{1-4}$ alkyl and wherein -T- is selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl.

Preferably, -L$^2$- and -L$^{2'}$- have a molecular weight in the range of from 14 g/mol to 750 g/mol.

Preferably, -L$^2$- comprises a moiety selected from

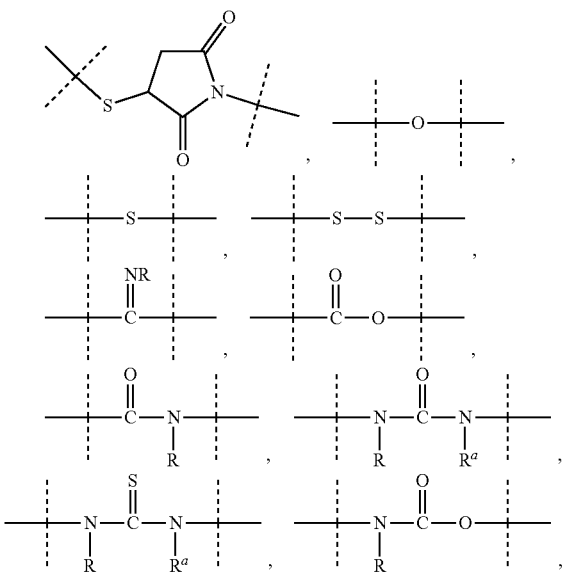

-continued

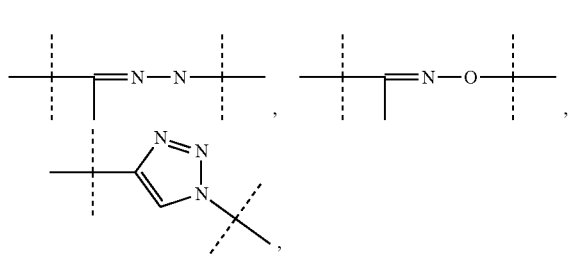

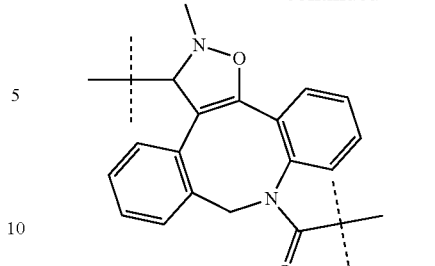

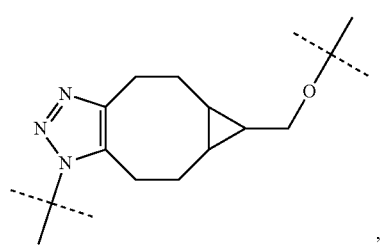

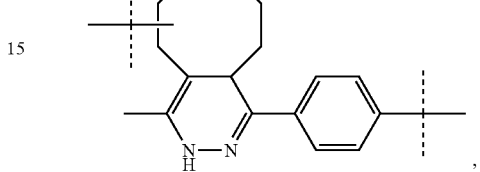

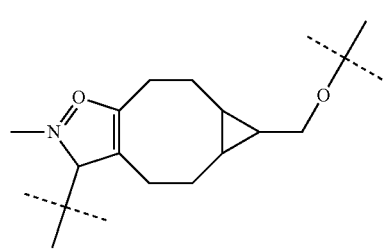

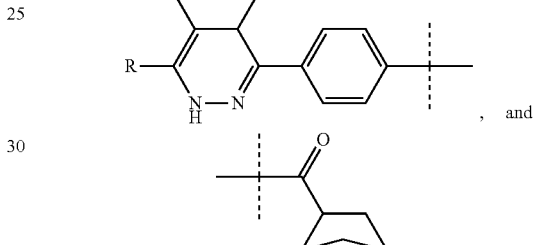

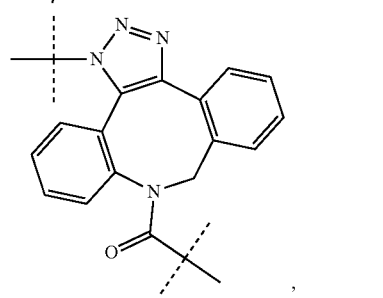

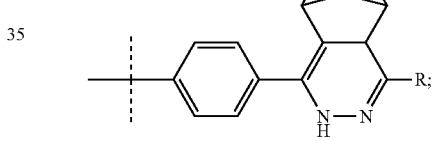, and wherein
dashed lines indicate attachment to the rest of -L²-; and
—R and —R$^a$ are independently of each other selected from the group consisting of —H, methyl, ethyl, propyl, butyl, pentyl and hexyl.

-L²-Z and -L²'-Y can be attached to -L¹- of formula (I) or (I') by replacing any —H present.

Preferably, one to five of the hydrogen given by —R¹, —R¹$^a$, —R², —R³, —R⁴, —R⁴$^a$, —R⁵, —R⁵$^a$, —R⁶, —R⁷ and —R⁷$^a$ are replaced by -L²-Z and/or -L²'-Y. More preferably, only one hydrogen of -L¹- of formula (I) or (I') is replaced by -L²-Z or -L²'-Y. In other words, it is preferred that -L¹- of formula (I) is substituted with one moiety -L²-Z and that -L- of formula (I') is substituted with one moiety -L²-Z or -L²'-Y.

In a preferred embodiment —R⁴$^a$ of formula (I) is substituted with -L²-Z, i.e. any one of the —H present in —R⁴$^a$ is replaced by -L²-Z. Preferably, —R⁴$^a$ is —H which is replaced by -L²-Z.

In a preferred embodiment —R⁴$^a$ of formula (I') is substituted with -L²-Z or -L²'-Y, i.e. any one of the —H present in —R⁴$^a$ is replaced by -L²-Z or -L²'-Y. Preferably, —R⁴$^a$ is —H which is replaced by -L²-Z or -L²'-Y.

In another embodiment —R⁴ of formula (I) is substituted with -L²-Z, i.e. any one of the —H present in —R⁴ is replaced by -L²-Z. Preferably, —R⁴ is —H which is replaced by -L²-Z.

In another embodiment —$R^4$ of formula (I') is substituted with -$L^2$-Z or -$L^{2'}$-Y, i.e. any one of the —H present in —$R^4$ is replaced by -$L^2$-Z or -$L^{2'}$-Y. Preferably, —$R^4$ is —H which is replaced by -$L^2$-Z or -$L^{2'}$-Y.

In another embodiment —$R^1$ of formula (I) is substituted with -$L^2$-Z, i.e. any one of the —H present in —$R^1$ is replaced by -$L^2$-Z. Preferably, —$R^1$ is —H which is replaced by -$L^2$-Z.

In another embodiment —$R^1$ of formula (I') is substituted with -$L^2$-Z or -$L^{2'}$-Y, i.e. any one of the —H present in —$R^1$ is replaced by -$L^2$-Z or -$L^{2'}$-Y. Preferably, —$R^1$ is —H which is replaced by -$L^2$-Z or -$L^{2'}$-Y.

In another embodiment —$R^{1a}$ of formula (I) is substituted with -$L^2$-Z, i.e. any one of the —H present in —$R^{1a}$ is replaced by -$L^2$-Z. Preferably, —$R^{1a}$ is —H which is replaced by -$L^2$-Z.

In another embodiment —$R^{1a}$ of formula (I') is substituted with -$L^2$-Z or -$L^{2'}$-Y, i.e. any one of the —H present in —$R^{1a}$ is replaced by -$L^2$-Z or -$L^{2'}$-Y. Preferably, —$R^{1a}$ is —H which is replaced by -$L^2$-Z or -$L^{2'}$-Y.

In another embodiment —$R^3$ of formula (I) is substituted with -$L^2$-Z, i.e. any one of the —H present in —$R^3$ is replaced by -$L^2$-Z. Preferably, —$R^3$ is —H which is replaced by -$L^2$-Z.

In another embodiment —$R^3$ of formula (I') is substituted with -$L^2$-Z or -$L^{2'}$-Y, i.e. any one of the —H present in —$R^3$ is replaced by -$L^2$-Z or -$L^{2'}$-Y. Preferably, —$R^3$ is —H which is replaced by -$L^2$-Z or -$L^{2'}$-Y.

Another aspect of the present invention is a method of synthesis of a prodrug or pharmaceutical salt thereof of the present invention.

Preferably, the method of synthesis of a prodrug of the present invention comprises the steps of
  (a) Providing a reagent comprising a moiety Y-$L^{2'}$-$L^1$-Q, wherein
    —Y is a functional group,
    -$L^2$- is a chemical bond or a spacer,
    -$L^1$- is of formula (I') which optionally comprises functional groups protected with protecting groups,
    -Q is —OH or a leaving group;
  (b) Reacting -Q of the reagent of step (a) with a primary or secondary amine or hydroxyl functional group of a drug D-H by forming an amide or ester linkage between -$L^1$- and -D, respectively; wherein the drug optionally comprises further functional groups which may optionally be protected with protecting groups;
  (c) Reacting a reagent comprising Z having at least one functional group —$Y^1$ with —Y of the intermediate of step (b) by forming a linkage between Z and -$L^{2'}$-, resulting in Z being conjugated to at least one moiety -$L^2$-$L^1$-D;
  (d) Optionally removing the protecting groups present.

It is understood that one or more functional groups —$Y^1$ of Z react with a functional group —Y, i.e. that one or more reagents of step (a) are conjugated to Z.

Preferred embodiments for —Y, -$L^1$-, -$L^{2'}$-, -$L^2$-, -D and -Q are as described above.

In an equally preferred embodiment the method of synthesis of a prodrug of the present invention comprises the steps of
  (a) Providing a reagent comprising a moiety Y-$L^{2'}$-$L^1$-Q, wherein
    —Y is a functional group,
    -$L^{2'}$- is a chemical bond or a spacer,
    -L- is of formula (I') which optionally comprises functional groups protected with protecting groups,
    -Q is —OH or a leaving group;
  (b) Reacting a reagent comprising Z having at least one functional group —$Y^1$ with —Y of the reagent of step (a) by forming a linkage between Z and -$L^{2'}$-, resulting in Z being conjugated to at least one moiety -$L^2$-$L^1$-Q;
  (c) Reacting -Q of the intermediate of step (b) with a primary or secondary amine or hydroxyl functional group of a drug D-H by forming an amide or ester linkage between $L^1$ and D, respectively; wherein the drug optionally comprises further functional groups which may optionally be protected with protecting groups;
  (d) Optionally removing the protecting groups present.

It is understood that one or more functional groups —$Y^1$ of Z react with a functional group —Y, i.e. that one or more reagents of step (a) are conjugated to Z.

Preferred embodiments for —Y, -$L^1$-, -$L^{2'}$-, -$L^2$-, -D and -Q are as described above.

Preferred embodiments of —$Y^1$ correspond to the preferred embodiments of —Y as described above.

The person skilled in the art is aware that not every Y can be used in combination with any Y' and will have no problem identifying suitable pairs. Preferred pairs Y/Y' are the following:
  Y is maleimide, Y' is selected from thiol, amine and selenide;
  Y' is maleimide, Y is selected from thiol, amine and selenide;
  Y is selected from formulas (z'vi), (z'iii) and (z'iv), Y' is of formula (z'x);
  Y' is selected from formulas (z'vi), (z'iii) and (z'iv), Y is of formula (z'x);
  Y is selected from formulas (z'ii), (z'v), (z'vii) and a terminal alkynyl, Y' is azide;
  Y' is selected from formulas (z'ii), (z'v), (z'vii) and a terminal alkynyl, Y is azide;
  Y is of formula (z'xx), Y' is azide;
  Y' is of formula (z'xx), Y is azide;
  Y is of formula (z'viii), Y' is of formula (z'i);
  Y' is of formula (z'viii), Y is of formula (z'i);
  Y is of formula (z'ix), Y' is of formula (z'iv);

It is understood that the above listed pairs Y/Y' are preferred examples and do not represent a comprehensive list of all possible pairs.

Another aspect of the present invention is a pharmaceutical composition comprising the prodrug of the present invention and one or more excipients.

A further aspect of the present invention is the prodrug of the present invention or the pharmaceutical composition comprising the prodrug of the present invention for use as a medicament.

Another aspect of the present invention is the prodrug or the pharmaceutical composition comprising the prodrug of the present invention for use in a method of treatment of a disease which can be treated with the corresponding drug released from the prodrug.

Another aspect of the present invention is the use of the prodrug or the pharmaceutical composition comprising the prodrug of the present invention for the manufacture of a medicament for treating a disease which can be treated with the corresponding drug released from the prodrug.

A further aspect of the present invention is a method of treating, controlling, delaying or preventing in a mammalian patient, preferably a human patient, in need of the treatment, control, delay or prevention of one or more diseases which can be treated with the corresponding drug released from the prodrug, comprising the step of administering to said patient in need thereof a therapeutically effective amount of the prodrug or the pharmaceutical composition the prodrug of the present invention.

An additional aspect of the present invention is a method of administering the prodrug or the pharmaceutical composition of the present invention, wherein the method comprises the step of administering the prodrug or the pharmaceutical composition of the present invention via topical, enteral or parenteral administration and by methods of external application, injection or infusion, including intraarticular, periarticular, intradermal, subcutaneous, intramuscular, intravenous, intraosseous, intraperitoneal, intrathecal, intracapsular, intraorbital, intravitreal, intratympanic, intravesical, intracardiac, transtracheal, subcuticular, subcapsular, subarachnoid, intraspinal, intraventricular, intrasternal injection and infusion, direct delivery to the brain via implanted device allowing delivery of the invention or the like to brain tissue or brain fluids (e.g., Ommaya Reservoir), direct intracerebroventricular injection or infusion, injection or infusion into brain or brain associated regions, injection into the subchoroidal space, retro-orbital injection and ocular instillation, preferably via subcutaneous injection.

EXAMPLES

Materials and Methods
Materials:
PEG 2 (example 1) was obtained from Biomatrik Inc., Jiaxing, China.
2-chlorotrityl resin, PyBOP, HATU and amino acids were purchased from Novabiochem, Merck Chemicals GmbH, Schwalbach, Germany.
TFA was purchased from Carl Roth GmbH & Co. KG, Karlsruhe, Germany.
All other chemicals were obtained from Sigma-Aldrich Chemie Gmbh, Munich, Germany.
Methods:
Reactions were performed with dry solvents ($CH_2Cl_2$, DMF, THF) purchased from Sigma-Aldrich Chemie GmbH, Munich, Germany. Generally, reactions were stirred at room temperature and monitored by LCMS.
Preparative HPLC was done on a reverse phase column (XBridge BEH300 C18 OBD Prep 10 μm 30×150 mm) connected to a Waters 600 or 2535 HPLC system and Waters 2489 absorbance detector. Gradients of solution A (0.1% TFA in $H_2O$) and solution B (0.1% TFA in acetonitrile) were used. HPLC fractions containing product were combined and lyophilized.
Preparative LPLC was done on a reverse phase column (Biotage SNAP KP-C18-HS) connected to an Isolera One system from Biotage AB, Sweden. Products were detected at 215 nm. Gradients of solution A (0.1% TFA in $H_2O$) and solution B (0.1% TFA in acetonitrile) were used. Fractions containing product were combined and lyophilized.
Flash chromatography purifications were performed on an Isolera One system from Biotage AB, Sweden, using Biotage KP-Sil silica cartridges and n-heptane, and ethyl acetate as eluents. Products were detected at 254 nm.
Analytical LCMS was performed on a Waters Acquity UPLC with an Acquity PDA detector coupled to a Waters Micromass ZQ or an Agilent technologies 1290 system with a G4212A diode array and a G6120B single quad MS system equipped with a Waters ACQUITY UPLC BEH300 C18 reverse phase column (2.1×50 mm, 300 Å, 1.7 m, flow: 0.25 ml/min; solvent A: $H_2O$+0.04% TFA, solvent B: acetonitrile+0.05% TFA).

Analytical UPLC-MS for protein conjugation reaction was performed on an Agilent 1290 Infinity system with an Acquity PDA detector coupled to an iFunnel QTOF equipped with a Waters ACQUITY UPLC BEH300 C4 reverse phase column (2.1×50 mm, 300 Å, 1.7 μm, flow: 0.25 ml/min; solvent A: $H_2O$+0.05% TFA, solvent B: acetonitrile+0.04% TFA).

Example 1

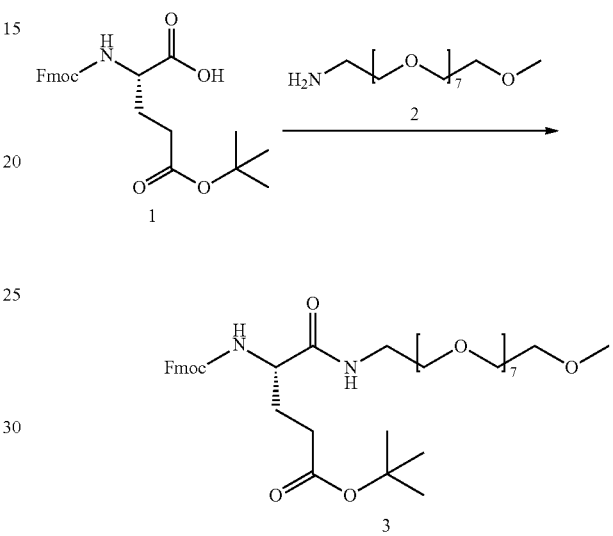

Fmoc-Glu(OtBu)-OH (1) (277.38 mg; 0.65 mmol; 1.00 eq.), m-dPEG8-amine (2) (250.00 mg; 0.65 mmol; 1.00 eq.) and PyBOP (508.89 mg; 0.98 mmol; 1.50 eq.) were dissolved in anhydrous DMF, (5.00 ml). Then DIPEA (340.66 μl; 1.96 mmol; 3.00 eq.) was added and the reaction mixture was stirred at room temperature for 1.5 hours. The reaction mixture was diluted with ethyl acetate (15 ml) and the organic solution was washed with 1 M HCl (3×15 ml) and brine (15 ml). The organic phase was dried over $MgSO_4$, filtered and concentrated. The residue was dried at HV overnight.
The crude product was purified by flash chromatography to yield the PEGylated glutamate 3 as colorless oil.
Yield: 517.00 mg, 100%

Example 2

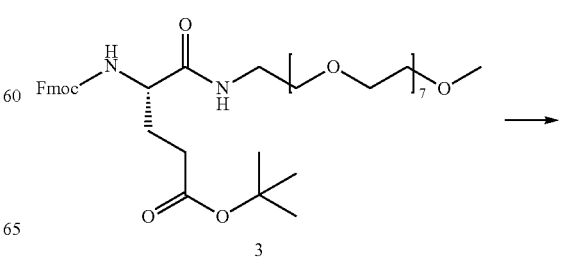

-continued

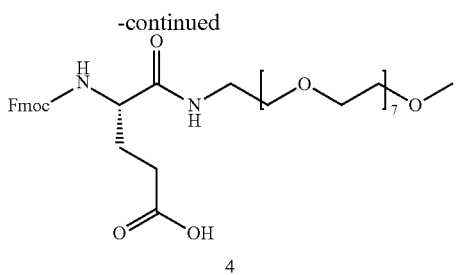

4

Glutamate ester 3 (258.50 mg; 325.98 µmol; 1.00 eq.) was dissolved in trifluoroacetic acid (2.00 ml; 25.96 mmol; 79.64 eq.) and the mixture was stirred at room temperature for 30 minutes. An LCMS chromatogram showed complete conversion to the product. The solvent was evaporated in a stream of argon and the product was dried in vacuo.

Yield: 268.00 mg, 100%

Example 3

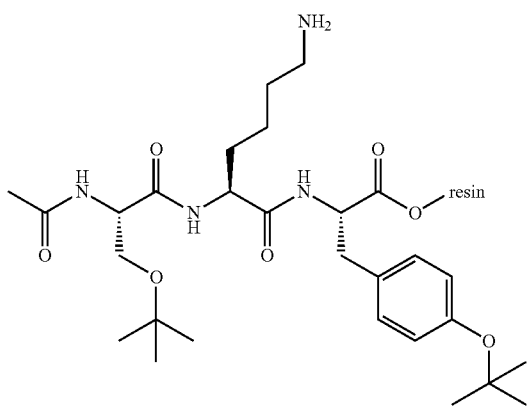

5

Step 1:
2-chlorotrityl chloride resin (1.33 mmol/g; 173 mg; 230 µmol, 1 eq.) was placed in a 5 ml syringe reactor and swollen in 1 ml DCM, and then the solvent was drained. Fmoc-Tyr(OtBu)-OH (317.20 mg; 0.69 mmol; 3.00 eq.) was suspended in DCM (1.00 ml), then DIPEA (0.16 ml; 0.92 mmol; 4.00 eq.) was added. The suspension turned into a clear solution. The solution was added to the pre-swollen resin and the mixture was shaken at room temperature for 1 h. The resin was washed with DCM (5×1 ml) and DMF (5×1 ml).

Step 2:
A solution of 96:2:2 DMF/piperidine/DBU (1 ml) was shaken with the resin for 5 min. The procedure was repeated twice. The resin was washed with DMF (7×1 ml).

Step 3:
A yellow solution of Fmoc-Lys(ivDde)-OH (396.70 mg; 0.69 mmol; 3.00 eq.), HATU (262.46 mg; 0.69 mmol; 3.00 eq.) and DIPEA (0.24 ml; 1.38 mmol; 6.00 eq.) in DMF (1.00 ml) was added to the resin. The reaction mixture was shaken at room temperature for 2 h. The resin was washed with DMF (7×1 ml).

Step 4:
A solution of 96:2:2 DMF/piperidine/DBU (1 ml) was shaken with the resin for 5 min. The procedure was repeated twice. The resin was washed with DMF (7×1 ml).

Step 5:
A yellow, clear solution of Fmoc-Ser(tBu)-OH (194.86 mg; 0.51 mmol; 3.00 eq.), HATU (193.23 mg; 0.51 mmol; 3.00 eq.) and DIPEA (131.36 mg; 1.02 mmol; 6.00 eq.) in DMF (2.00 ml) was added to H-Lys(ivDde)-Tyr(tBu)-O-resin (137.00 mg; 0.17 mmol; 1.00 eq.). The reaction mixture was shaken at room temperature for 3 h. The resin was washed with dimethylformamide (6×2 ml) and dichloromethane (6×2 ml). The resin was dried under high vacuum for 1 hour.

Step 6:
A solution of 96:2:2 DMF/piperidine/DBU (2 ml) was shaken with the resin for 5 min. The procedure was repeated twice. The resin was washed with DMF (7×1 ml).

Step 7:
Acetic anhydride (240.18 µl; 2.54 mmol; 15.00 eq.) and DIPEA (442.58 µl; 2.54 mmol; 15.00 eq.) in DMF (2.00 ml) were added to the resin. The suspension was shaken for 1.5 h at room temperature. The resin was washed with DMF (6×2 ml) and dichloromethane (6×2 ml). The resin was dried under high vacuum for 1 hour.

Step 8:
A solution of 4% hydrazine hydrate (80.00 µl; 1.64 mmol; 9.71 eq.) in DMF (1.92 ml) (v/v) was shaken with the resin for 15 min. The resin was washed with DMF (7×1 ml) and DCM (6×1 ml). The resin was dried under high vacuum for 1 hour.

Example 4

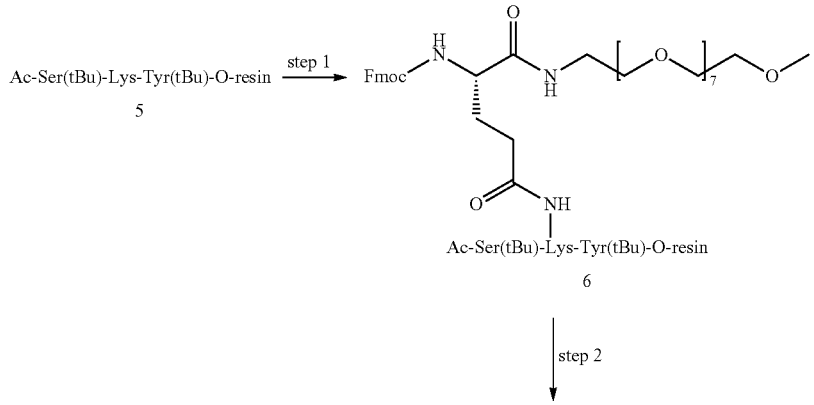

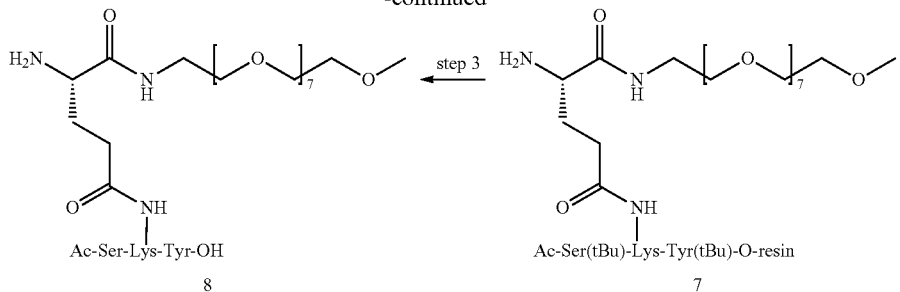

Ac-Ser-Lys-Tyr-OH
8

Ac-Ser(tBu)-Lys-Tyr(tBu)-O-resin
7

Step 1:

Carboxylic acid 4 (151.00 mg; 183.67 µmol; 3.99 eq.) and PyBOP (83.90 mg; 161.22 µmol; 3.50 eq.) were dissolved in DMF (1.00 ml). DIPEA (56.16 µl; 322.44 µmol; 7.00 eq.) was added and the solution was drawn into a 2 ml syringe reactor, containing resin 5 (60.00 mg; 46.06 µmol; 1.00 eq.). The reaction mixture was shaken at room temperature for 3 h. The resin was washed 5 times with 1 ml of DMF and 5 times with 5 ml of DCM. The resin was dried under high vacuum for 10 minutes.

Step 2:

A solution of 20% piperidine in DMF (1 ml) was drawn into the syringe reactor, containing Fmoc protected amine 6. The reaction mixture was shaken for 15 minutes. The procedure was repeated once. The resin was washed 5 times with 1 ml of DMF and 5 times with 5 ml of DCM.

Step 3:

A solution of 95:2.5:2.5 TFA/TES/H$_2$O (1 ml) was added to resin 7 and the mixture was shaken in the syringe reactor for 1 h. The resin was filtered off and washed with DCM (6×1 ml). The filtrate was concentrated and the crude product was purified by preparative HPLC to yield 8.

Yield: 8.5 mg, 18% over 11 steps

Example 5

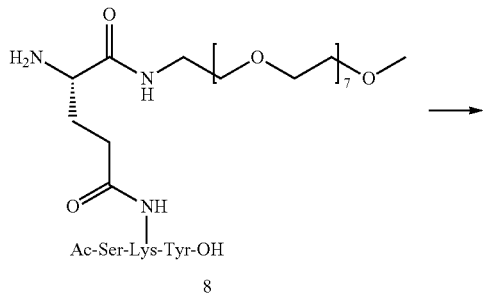

Ac-Ser-Lys-Tyr-OH
8

→

Ac-Ser-Lys-Tyr-OH
9

+

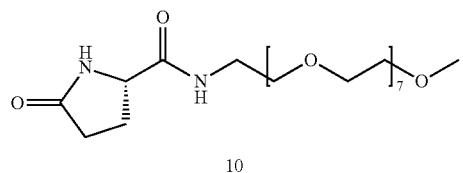

10

The hydrolysis kinetics of PEGylated linker-peptide conjugate 8 were studied at pH 7.4, 37° C. and pH 8.9, 37° C. Therefore, the starting material 8 was dissolved in two different buffers (60 mM phosphate, pH 7.4 and 100 mM borate pH 8.9, respectively). The resulting solutions were incubated in a water bath at 37° C. At given points in time samples were withdrawn, quenched and analyzed by LCMS. Curve fitting software was applied to determine the corresponding half-life of the release.

Ac-Ser-Lys-Tyr-OH (9) was released with a half-life of 56 d at pH 7.4 and 220 d at pH 8.9.

Example 6

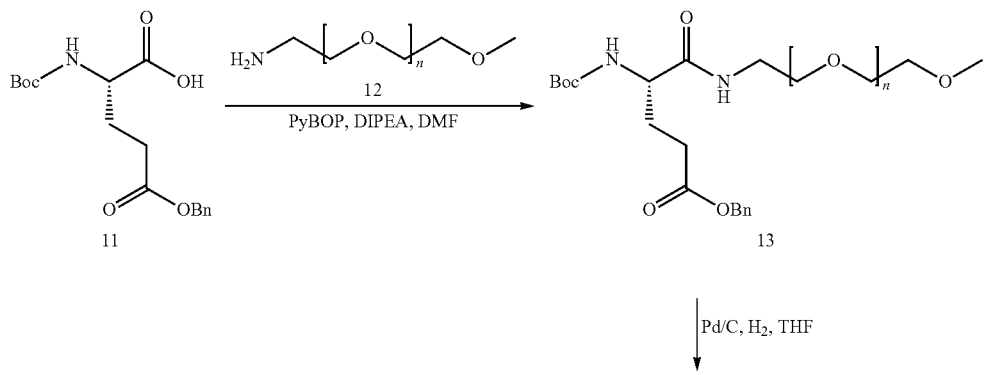

Pd/C, H$_2$, THF

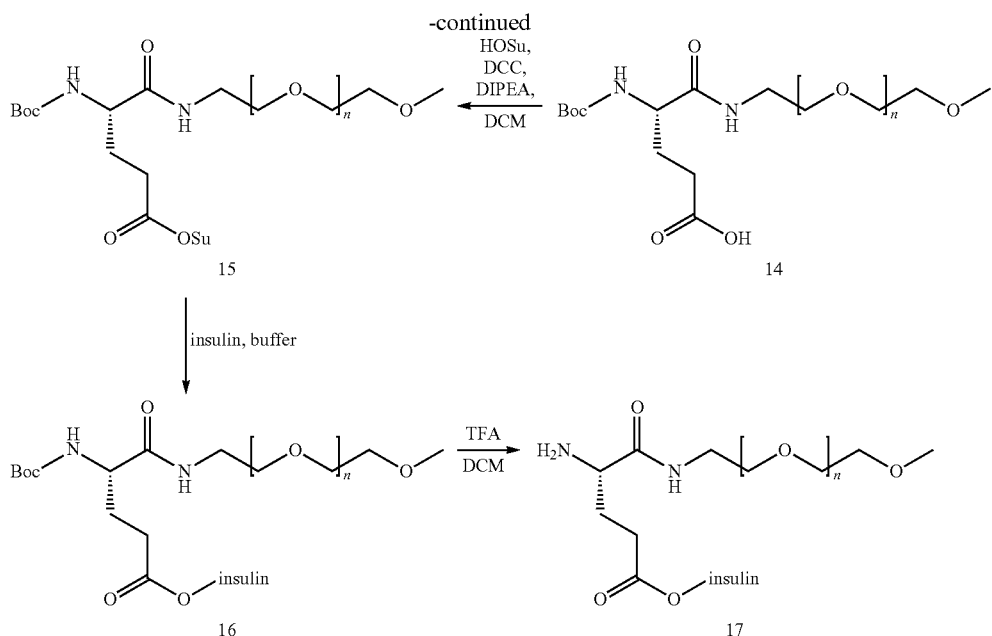

Boc-Glu(Bn)-OH (11) (1 eq), PEG amine 12 (1 eq, n=14), PyBOP (1.5 eq) and DIPEA (3 eq) are stirred in DMF until full conversion is obtained. The reaction mixture is diluted with ethyl acetate and the organic solution is washed with 1 M HCl and brine. The organic phase is dried over MgSO$_4$, filtered and concentrated. The residue is purified by flash chromatography to yield the PEGylated glutamate 13.

Benzyl ester 13 (1 eq) is stirred with Pd/C (10%) in THF under an atmosphere of hydrogen until full conversion of the starting material. The mixture is filtered through Celite and concentrated to yield carboxylic acid 14.

Carboxylic acid 14 (1 eq) is stirred with DCC (1.3 eq), HOSu (1.3 eq) and DIPEA (2.6 eq) in DCM to yield active ester 15. The crude compound is purified by preparative HPLC.

Active ester 15 is conjugated to insulin in a mixture of DMF and buffer (pH 8). Protected insulin-linker conjugate 16 is purified by preparative HPLC.

The protected insulin-linker conjugate 16 is stirred in a mixture of 9:1:0.25 HFIP/TFA/TES until the Boc group is removed completely. The solution is concentrated and the crude product is purified by preparative HPLC to yield final conjugate 17.

Example 7

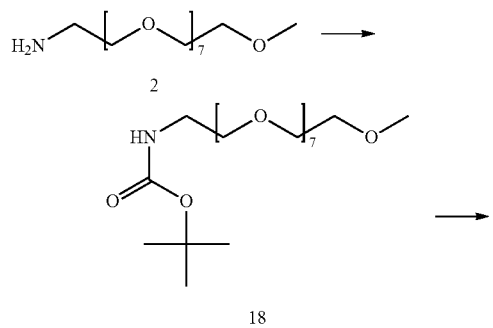

-continued

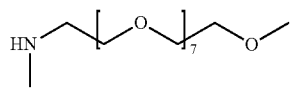

m-PEG$_8$-NH$_2$ (2) (400.00 mg; 1.04 mmol; 1.00 eq.) was dissolved in THF (4 ml) and cooled to 0° C. A solution of di-tert-butyl dicarbonate (295.95 mg; 1.36 mmol; 1.30 eq.) in 4 ml of THF was added dropwise and the reaction mixture was stirred at room temperature for 3 h. The reaction mixture was diluted with dichloromethane (50 ml) and extracted two times with saturated NaHCO$_3$ (50 ml) and once with brine (50 ml). The organic layer was dried over Na$_2$SO$_4$, filtered and concentrated under reduced pressure. The residue was dried under high vacuum overnight yielding a colorless oil (18) (499 mg, 99%).

The residue (18) (499 mg; 1.03 mmol; 1.00 eq.) was dissolved in THF (4.99 ml) and the solution was added dropwise to a cold (0° C.) solution of lithium aluminum hydride (1 M in THF) (1.03 ml; 1.00 mol/l; 1.03 mmol; 1.00 eq.). The reaction mixture was stirred for 10 min at room temperature and was then heated to 60° C. and stirred for 5 h. The reaction mixture was cooled to 0° C., 43 µl of water were added, and the mixture was stirred for 4 min. 42 µl of 3N NaOH and 43 µl of water were added, and the mixture was stirred for 30 min at room temperature. MgSO$_4$ was added, the suspension was filtered through a small bed of celite and the filter cake was washed with THF. The resulting solution was concentrated under reduced pressure and the residue was dried under high vacuum overnight.

Yield: 378 mg, 92%, colorless oil

87

Example 8

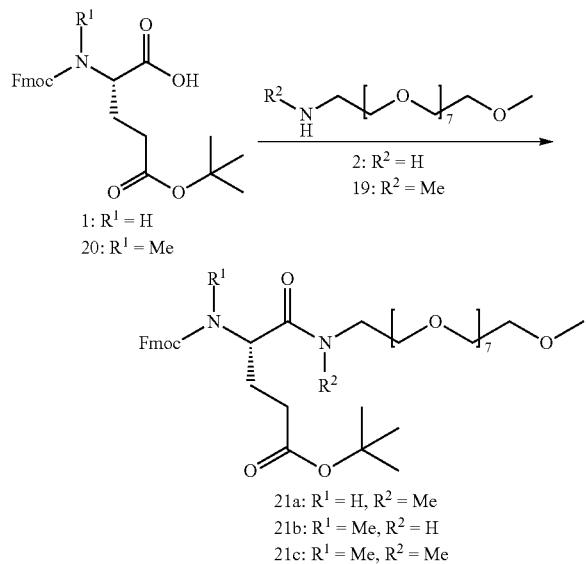

Preparation of 21a: According to example 1 using 19 (378.00 mg; 0.95 mmol; 1.00 eq.) instead of 2. All other reagents were adjusted to scale. Purification by preparative HPLC.

Yield: 427 mg, 56%, colorless oil Preparation of 21b: According to example 1 using 20 (143.26 mg; 0.33 mmol; 1.00 eq.) instead of 1. All other reagents were adjusted to scale.

Yield: 233 mg, 89%, colorless oil Preparation of 21c: According to example 1 using 20 (221.13 mg; 0.50 mmol; 1.00 eq.) instead of 1 and 19 (200.00 mg; 0.50 mmol; 1.00 eq.) instead of 2. All other reagents were adjusted to scale. Purification by preparative HPLC.

Yield: 299 mg, 73%, colorless oil

88

Example 9

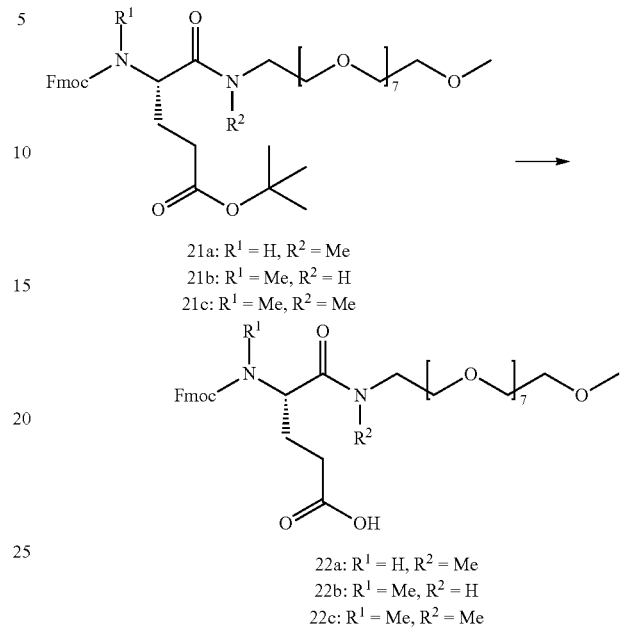

Preparation of 22a: According to example 2 using 21a (426.70 mg; 0.53 mmol; 1.00 eq.). All other reagents were adjusted to scale.

Yield: 397 mg, 100%, colorless oil Preparation of 22b: According to example 2 using 21b (233.00 mg; 0.29 mmol; 1.00 eq.). All other reagents were adjusted to scale.

Yield: 236 mg, 100%, colorless oil

Preparation of 22c: According to example 2 using 21c (299.00 mg; 0.37 mmol; 1.00 eq.). All other reagents were adjusted to scale.

Yield: 348 mg, 100%, colorless oil

Example 10

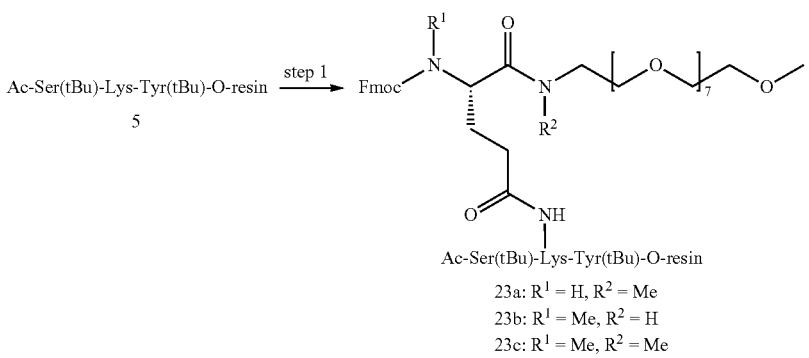

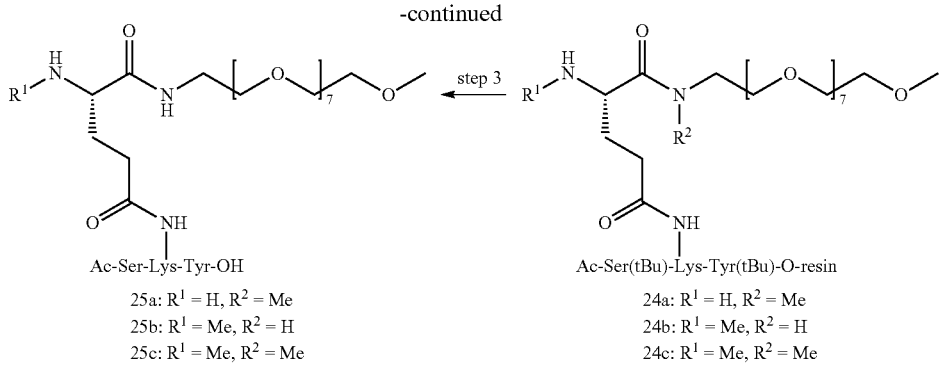

Ac-Ser-Lys-Tyr-OH
25a: R¹ = H, R² = Me
25b: R¹ = Me, R² = H
25c: R¹ = Me, R² = Me

Ac-Ser(tBu)-Lys-Tyr(tBu)-O-resin
24a: R¹ = H, R² = Me
24b: R¹ = Me, R² = H
24c: R¹ = Me, R² = Me Preparation of 25a: According to example 4 using 22a (79.6 mg; 106 µmol; 2.50 eq.). All other reagents were adjusted to scale.

Yield: 31 mg, 77%

Preparation of 25b: According to example 4 using 22b (35.7 mg; 43 µmol; 2.50 eq.). All other reagents were adjusted to scale.

Yield: 10.4 mg, 65%

Preparation of 25c: According to example 4 using 22c (81 mg; 106 µmol; 2.50 eq.). All other reagents were adjusted to scale.

Yield: 31 mg, 76%

Example 11

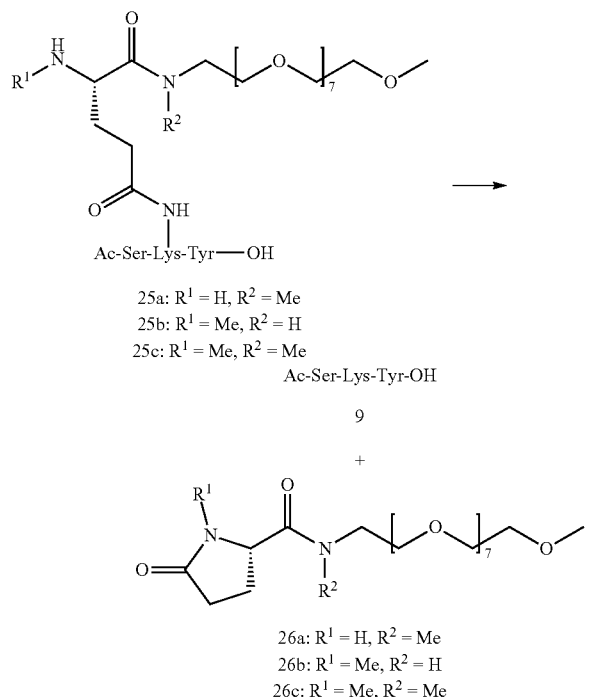

Ac-Ser-Lys-Tyr—OH
25a: R¹ = H, R² = Me
25b: R¹ = Me, R² = H
25c: R¹ = Me, R² = Me

Ac-Ser-Lys-Tyr-OH
9

+

26a: R¹ = H, R² = Me
26b: R¹ = Me, R² = H
26c: R¹ = Me, R² = Me

Release kinetics were setup and analyzed according to example 5 with additional buffers at 37° C. Results are depicted in the table below.

| compound | buffer | pH | half-life |
|---|---|---|---|
| 25a | 100 mM sodium phosphate | 7.4 | 26 d |
| 25b | 100 mM sodium phosphate | 7.4 | 164 d |
| 25c | 100 mM sodium phosphate | 7.4 | 55 d |
| 25c | 30 mM sodium phosphate | 7.4 | 55 d |
| 25c | 60 mM sodium phosphate | 7.4 | 36 d |
| 25c | 200 mM sodium phosphate | 7.4 | 17 d |
| 25c | 100 mM sodium phosphate | 6.5 | 35 d |
| 25c | 30 mM sodium citrate | 6.5 | 339 d |
| 25c | 100 mM sodium citrate | 4.0 | 129 d |
| 25c | 100 mM sodium citrate | 5.5 | 207 d |
| 25c | 100 mM sodium citrate | 6.5 | 336 d |
| 25c | 100 mM sodium borate | 9.0 | 92 d |
| 25c | 60 mM HEPES, 130 mM NaCl | 7.4 | 149 d |

The release is accelerated by phosphate in a concentration dependent matter. Citrate buffer shows good storage stability.

Example 12

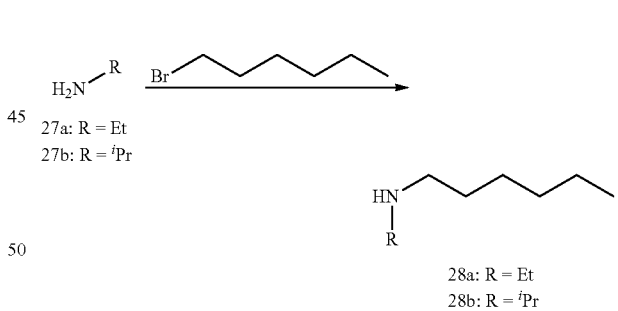

27a: R = Et
27b: R = iPr

28a: R = Et
28b: R = iPr

General procedure for the synthesis of 28a-b: The amine (9.09 mmol, 10.00 eq.) was dissolved in acetonitrile (1.50 ml). n-hexyl bromide (127.55 µL; 0.91 mmol; 1.00 eq.) was added and the reaction was stirred for 16 h. The volatiles were removed in a stream of nitrogen and the residue was purified by preparative HPLC.

Synthesis of 28a: Use of 27a (ethylamine, 2 M solution in THF (4.54 mL; 2.00 mol/l; 9.09 mmol; 10.00 eq.)) yielded 28a as colorless oil (171 mg, TFA salt, 77%)

Synthesis of 28b: Use of 27b (isopropylamine (781 µL; 9.09 mmol; 10.00 eq.)) yielded 28b as colorless oil (207 mg, TFA salt, 89%)

Example 13

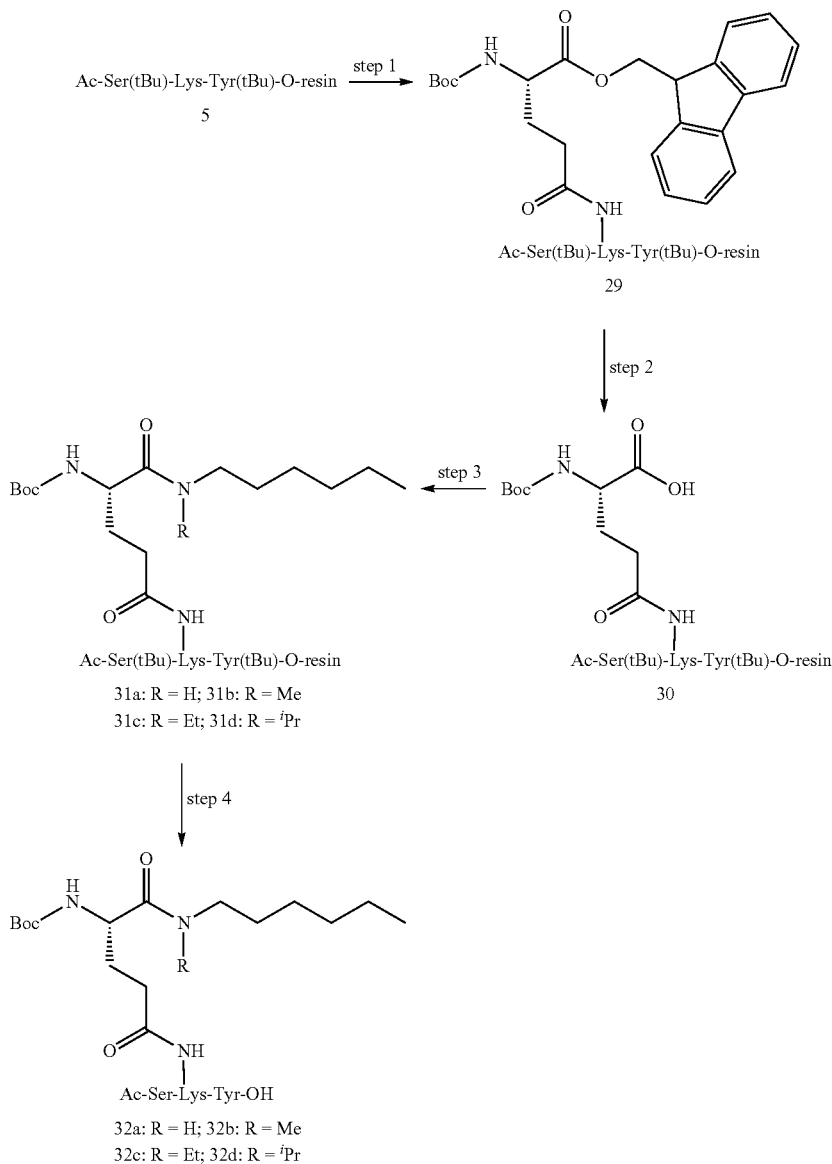

General procedure for the synthesis of 32a-d:

Step 1:

Boc-Glu-OFm (72 mg; 170 μmol; 2.00 eq.) and PyBOP (88.5 mg; 170 μmol; 2.00 eq.) were dissolved in DMF (1.00 ml). DIPEA (0.06 mL; 340 μmol; 4.00 eq.) was added and the solution was drawn into a 2 ml syringe reactor, containing resin 5 (100.00 mg; 85.00 μmol; 1.00 eq.). The reaction mixture was shaken at room temperature for 2 h. The resin was washed 5 times with 1 ml of DMF.

Step 2:

A solution of DMF/piperidine/DBU 96:2:2 (2 ml) was drawn into the syringe reactor, containing Fm protected acid 29. The reaction mixture was shaken for 30 minutes. The procedure was repeated 2× for 15 min. The resin was washed 5 times with 1 ml of DMF and 5 times with 5 ml of DCM and was dried under high vacuum for 10 minutes.

Step 3:

PyBOP (27.32 mg; 52.50 μmol; 2.50 eq.) and DIPEA (0.02 mL; 105.00 μmol; 5.00 eq.) were dissolved in DMF (0.50 ml) and the solution was drawn into a 2 ml syringe reactor, containing 30 (30 mg; 21.00 μmol; 1.00 eq.). The syringe was shaken and a solution of the amine (52.50 μmol; 2.50 eq.) in 0.1 ml DMF was drawn into the syringe. The reaction mixture was shaken at room temperature for 1.5 h. The resin was washed 5 times with 1 ml DMF and 5 times with 1 ml of DCM.

Step 4:

A solution of 95:2.5:2.5 TFA/TES/H$_2$O (1 ml) was added to the resin and the mixture was shaken in the syringe reactor for 30 min. The solution was collected and again a solution of 95:2.5:2.5 TFA/TES/H$_2$O (1 ml) was added to the resin and the mixture was shaken in the syringe reactor for 15 minutes. The resin was filtered off and washed with DCM (3×1 ml). All solutions were combined. The filtrate was concentrated and the crude product was purified by preparative HPLC.

Preparation of 32a: According to general procedure above using 1-hexylamine (5.3 mg; 52.50 µmol; 2.50 eq.) in step 3.
Yield: 6.2 mg, 39%

Preparation of 32b: According to general procedure above using n-hexylmethylamine (6 mg; 52.50 µmol; 2.50 eq.) in step 3.
Yield: 7.8 mg, 48%

Preparation of 32c: According to general procedure above using n-hexylethylamine 28a (12.8 mg; 52.50 µmol; 2.50 eq.) and increasing the DIPEA equivalents to 7.5 eq. in step 3.
Yield: 9.3 mg, 56%

Preparation of 32d: According to general procedure above using n-hexylisopropylamine 28b (12.8 mg; 52.50 µmol; 2.50 eq.) and increasing the DIPEA equivalents to 7.5 eq. in step 3.
Yield: 4.3 mg, 25%

Example 14

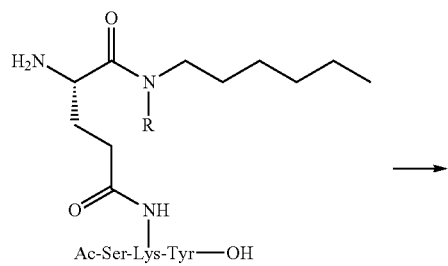

32a: R = H; 32b: R = Me
32c: R = Et; 32d: R = $^i$Pr

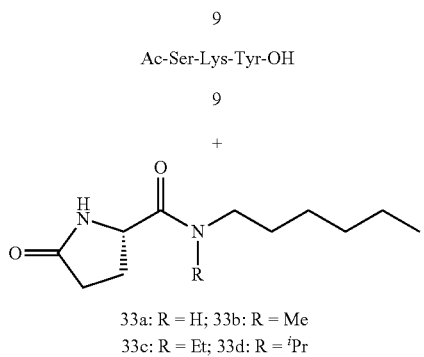

33a: R = H; 33b: R = Me
33c: R = Et; 33d: R = $^i$Pr

Release kinetics were setup and analyzed according to example 5 with changed buffers.
Results are depicted in the table below.

| compound | buffer | pH | halftime |
| --- | --- | --- | --- |
| 32a | 60 mM sodium phosphate | 7.4 | 54 d |
| 32b | 60 mM sodium phosphate | 7.4 | 37 d |
| 32c | 60 mM sodium phosphate | 7.4 | 40 d |
| 32d | 60 mM sodium phosphate | 7.4 | 39 d |
| 32a | 100 mM sodium phosphate | 7.4 | 38 d |
| 32b | 100 mM sodium phosphate | 7.4 | 25 d |
| 32c | 100 mM sodium phosphate | 7.4 | 30 d |
| 32d | 100 mM sodium phosphate | 7.4 | 29 d |

Example 15

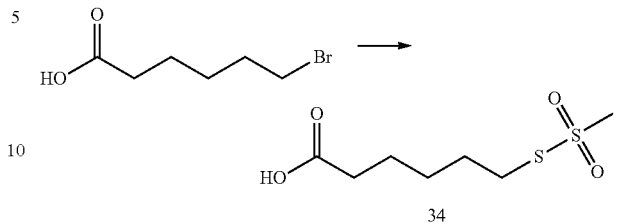

6-bromohexanoic acid (5.89 g; 30.19 mmol; 1.00 eq.) and sodium methanethiosulfonate (4.05 g; 30.19 mmol; 1.00 eq.) were dissolved in DMF (47.10 ml) under argon-atmosphere. The reaction mixture was stirred at 80° C. for 3 hours and then brought to room temperature. The reaction mixture was diluted with 116 ml water and was washed three times with 233 ml of diethyl ether. The organic phase was washed with brine (350 ml), dried over MgSO$_4$, filtered and concentrated under reduced pressure to a volume of 40 ml. The product was precipitated from the resulting solution in 2×1150 ml of cold n-heptane. Precipitation was completed overnight at −18° C. The supernatant was decanted and the precipitate was dissolved in 80 ml diethylether. The product was precipitated from the resulting solution in 2×1000 ml of cold n-heptane. The suspension was stored at −18° C. for 2 hours. The precipitate was filtered and the solid was dried under high vacuum over night to give 34 as white solid.
Yield: 5.62 g, 82%

Example 16

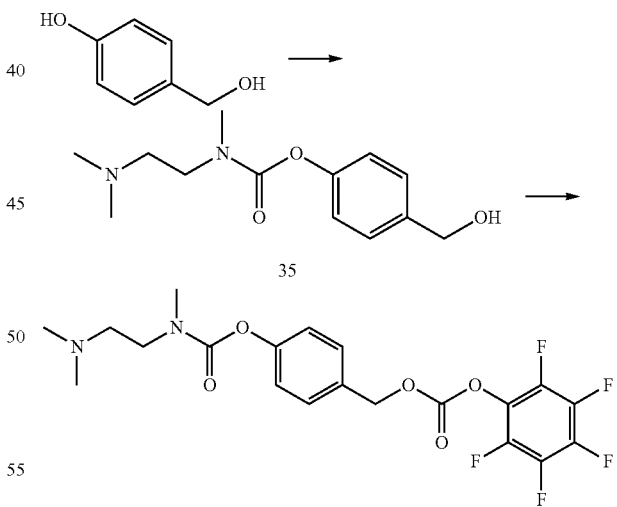

4-Hydroxybenzyl alcohol (1.70 g; 13.69 mmol; 1.00 eq.) was dissolved in THF (20.5 ml) and DIPEA (4.77 mL; 27.39 mmol; 2.00 eq.) was added. 4-nitrophenyl chloroformate (2.90 g; 14.38 mmol; 1.05 eq.) was dissolved in THF (5 ml) and was slowly dosed (via syringe pump within 30 min to the reaction mixture. The reaction was stirred for 30 additional minutes. N,N,N'-trimethylethylenediamine (2.21 mL; 17.12 mmol; 1.25 eq.) was slowly added to the reaction mixture and stirring was continued for 30 minutes. The reaction mixture was cooled to 0° C. with an ice bath and was quenched with TFA (3.17 mL; 41.08 mmol; 3.00 eq.). The solution was diluted with 100 ml of water (pH<2) and was washed three times with 100 ml of ethyl acetate. The aqueous phase was frozen and lyophilized. The residue was co-evaporated with ethyl acetate. The residue was dissolved in 60 ml of dichloromethane and the solution was dried with Na$_2$SO$_4$, filtered and evaporated. The residue was dried under HV for 2 hours.

The residue was dissolved in anhydrous acetonitrile (25 mL) and the solution was cooled with an ice-bath. Bis(pentafluorophenyl) carbonate (10.79 g; 27.38 mmol; 2.00 eq.), 4-(dimethylamino)pyridine (0.33 g; 2.74 mmol; 0.20 eq.) and DIPEA (9.54 mL; 54.76 mmol; 4.00 eq.) were added with stirring. The solution turned blue and a precipitate was visible. The reaction was stirred for 10 min. The reaction was cooled with an ice/NaCl bath to −15° C. and was quenched with a mixture of TFA (4.22 mL; 54.76 mmol; 4.00 eq.) and water/TFA 1:0.001 (13.54 mL). The solution was kept on ice and the product was purified by preparative LPLC.

Yield: 4.87 g (TFA salt), 62%

Example 17

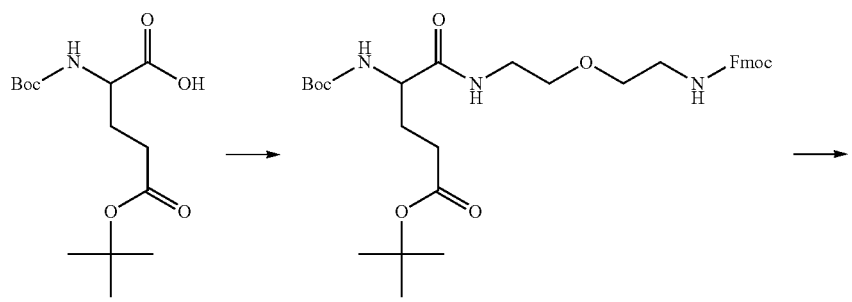

37

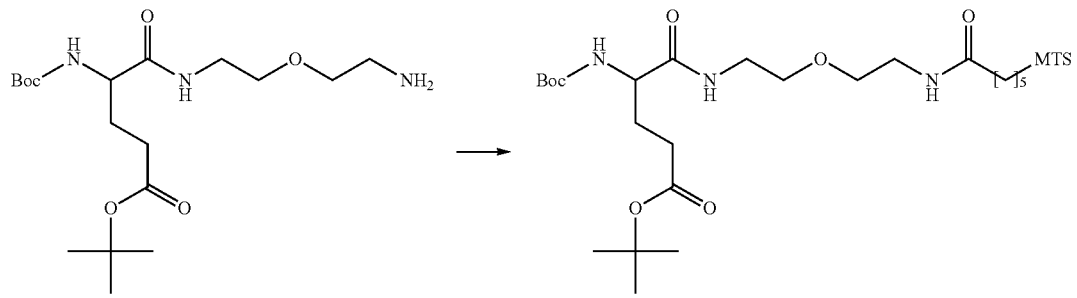

38  39

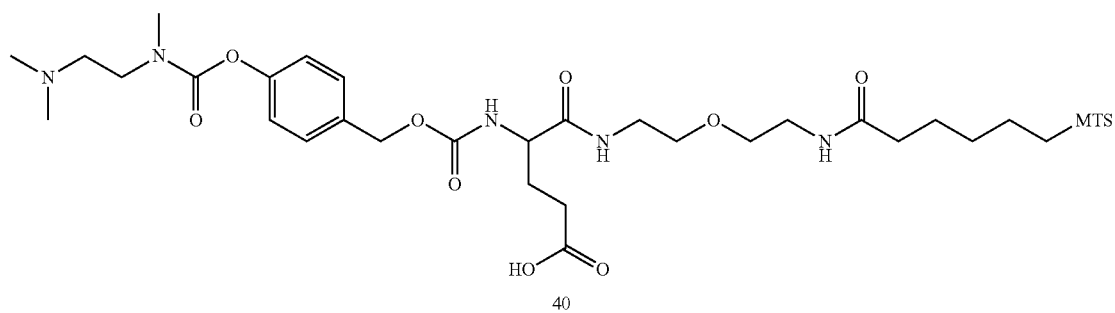

40

-continued

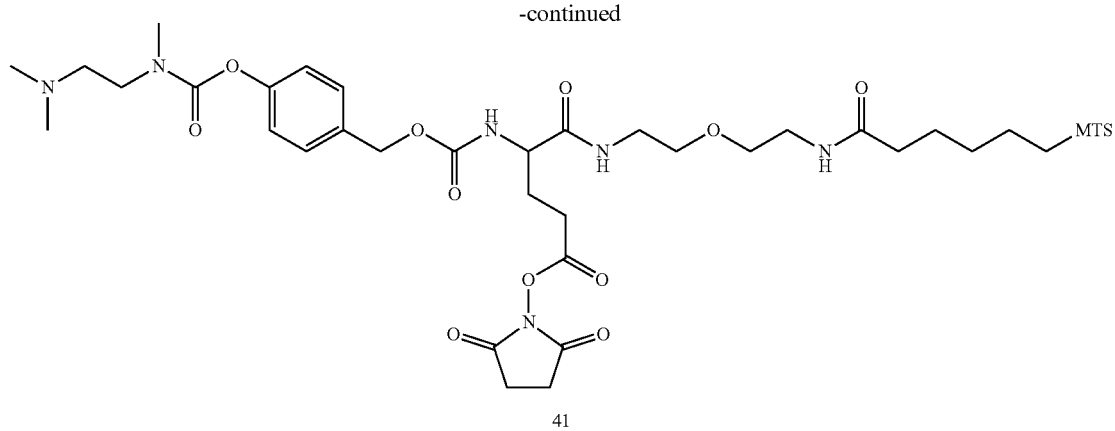

41

Boc-Glu(OtBu)-OH (380.01 mg; 1.25 mmol; 1.00 eq.) was dissolved in DMF (9.09 mL). PyBOP (977.85 mg; 1.88 mmol; 1.50 eq.), DIPEA (1.09 mL; 6.26 mmol; 5.00 eq.) and Fmoc-2-(2-aminoethoxy)-ethylamine hydrochloride (500.00 mg; 1.38 mmol; 1.10 eq.) were added. The mixture was stirred for 1 hour. The reaction mixture was diluted with 50 ml dichloromethane and was washed three times with 50 ml of 0.1 N HCl. The organic layer was washed two times with 50 ml saturated NaHCO$_3$ and once with 50 ml of brine. The organic layer was dried with MgSO$_4$, filtered and evaporated. The crude product was purified by flash chromatography to yield 37 as white foam.

Yield: 688 mg, 90%

This compound (37, 688.00 mg; 1.12 mmol; 1.00 eq.) was dissolved in THF (9.98 mL). DBU (194.72 µL; 1.30 mmol; 1.16 eq.) was added and the mixture was stirred at room temperature for 20 min. The solution was concentrated in a stream of argon and purified by flash chromatography to yield 38 as colorless oil.

Yield: 342 mg, 78%

Compound 38 (342.00 mg; 0.88 mmol; 1.00 eq.) was dissolved in DCM (6.00 mL) and PyBOP (548.33 mg; 1.05 mmol; 1.20 eq.), 34 (238.47 mg; 1.05 mmol; 1.20 eq.) and DIPEA (0.46 mL; 2.63 mmol; 3.00 eq.) were added. The reaction was stirred for 30 min. The reaction was quenched with AcOH (0.46 ml) and diluted with 20 ml DCM, and 20 ml 0.1 M HCl was added. The organic phase was separated and the aqueous phase extracted 2× with 20 mL DCM. The aqueous phase was saturated with NaCl and extracted 3× with DCM. The organic phases were combined and the resulting solution concentrated in vacuo. The residue was purified by preparative HPLC to give 39.

Yield: 421 mg, 80%

This compound (39, 421.00 mg; 0.70 mmol; 1.00 eq.) was dissolved in DCM (4.21 mL) and TFA (4.21 mL) was added with vigorous stirring in an open flask. After 1 h the volatiles were removed in a stream of nitrogen. The residue was further dried in vacuo for 15 min. Compound 39 (527.71 mg; 0.92 mmol; 1.30 eq.) was dissolved in anhydrous acetonitrile (4.21 mL) and DIPEA (1.23 mL; 7.04 mmol; 10.00 eq.) was added while cooling (ice-bath). The residue from above was dissolved in anhydrous acetonitrile (4.21 mL) and dropwise added over 5 minutes to the solution of 36. The reaction was further stirred for 5 min in the ice bath. TFA (0.4 mL; 5.28 mmol; 7.5 eq.) was added to the reaction. The solvent was removed in vacuo and the residue purified by preparative HPLC to give 40.

Yield: 447 mg (TFA salt), 76%

Compound 40 (63.00 mg; 75.55 µmol; 1.00 eq.) was dissolved in DCM (2.00 mL) and HOSu (26.08 mg; 226.65 µmol; 3.00 eq.) and DCC (46.76 mg; 226.65 µmol; 3.00 eq.) were added with stirring. A precipitate formed. After 30 min of stirring the volatiles were removed in vacuo. The residue was suspended in MeCN/H$_2$O/TFA 1:1:0.002 and filtered. The filtrate was purified by preparative HPLC to give 41.

Yield: 58.5 mg, 83%

Abbreviations

Boc tert-butyloxycarbonyl
DIPEA diisopropylethylamine
DCC dicyclohexylcarbodiimide
DBU 1,3-diazabicyclo[5.4.0]undecene
DCM dichloromethane
DMF dimethylformamide
DTT dihiothreitol
Fab fragment antigen-binding
Fm 9-fluorenylmethyl
Fmoc 9-fluorenylmethoxycarbonyl
HATU 1-[bis(dimethylamino)methylene]-1H-1,2,3-triazolo[4,5-b]pyridinium 3-oxid hexafluorophosphate
HFIP hexafluoroisopropanol
HOSu hydroxysuccinimide
HPLC high performance liquid chromatography
HV high vacuum
$^i$Pr isopropyl
ivDde 1-(4,4-dimethyl-2,6-dioxocyclohex-1-ylidene)-3-methylbutyl
LCMS mass spectrometry-coupled liquid chromatography
MS mass spectrum/mass spectrometry
MTS methanethiosulfonate
PEG poly(ethylene glycol)
PyBOP (benzotriazole-1-yl-oxy)-tris-pyrrolidino-phosphonium hexafluorophosphate
tBu tertiary butyl
TES triethylsilane
THF tetrahydrofurane
TFA trifluoroacetic acid
UPLC ultra performance liquid chromatography

The invention claimed is:
1. A conjugate D-L$^1$ or a pharmaceutically acceptable salt thereof,
wherein
-D is a primary or secondary amine-comprising biologically active moiety; and

-$L^1$ is represented by formula (I):

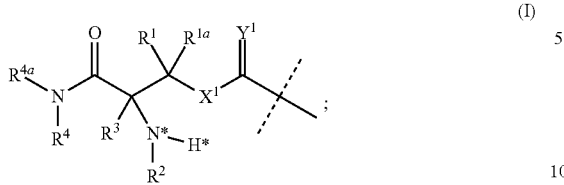

wherein:
the dashed line indicates attachment to the primary or secondary amine of the biologically active moiety;
—$X^1$ is selected from the group consisting of —$C(R^5R^{5a})$—, —O—, —$N(R^5)$—, and —S—;
—$R^4$ is methyl;
—$R^1$, $R^{1a}$, $R^2$, $R^3$, $R^{4a}$, $R^5$, and —$R^{5a}$ are independently of each other selected from the group consisting of —H, $C_{1-6}$ alkyl, $C_{2-6}$ alkenyl, and $C_{2-6}$ alkynyl, wherein:
$C_{1-6}$ alkyl, $C_{2-6}$ alkenyl, and $C_{2-6}$ alkynyl are optionally substituted with one or more $R^6$, which are the same or different; and
$C_{1-6}$ alkyl, $C_{2-6}$ alkenyl, and $C_{2-6}$ alkynyl are optionally interrupted by one or more groups selected from the group consisting of —T—, —C(O)O—, —O—, —C(O)—, —C(O)N($R^7$)—, —S(O)$_2$N($R^7$)—, —S(O)N($R^7$)—, —S(O)$_2$—, —S(O)—, —N($R^7$)S(O)$_2$N($R^{7a}$)—, —S—, —N($R^7$)—, —OC(O$R^7$)($R^{7a}$)—, —N($R^7$)C(O)N($R^{7a}$)—, and —OC(O)N($R^7$)—, provided that the nitrogen marked with the asterisk is connected to —$R^2$ through an $SP^3$-hybridized carbon atom of —$R^2$;
each T is independently of each other selected from the group consisting of phenyl, naphthyl, indenyl, indenyl, tetralinyl, $C_{3-10}$ cycloalkyl, 3- to 10-membered heterocyclyl, and 8- to 11-membered heterobicyclyl, wherein:
each T is independently optionally substituted with one or more $R^6$, which are the same or different;
each —$R^6$, —$R^7$, and —$R^{7a}$ is independently selected from the group consisting of —H and $C_{1-6}$ alkyl, wherein:
$C_{1-6}$ alkyl is optionally substituted with one or more halogen, which are the same or different;
=$Y^1$ is selected from =O and =$NR^5$;
optionally, one or more of the pairs —$R^1$/—$R^{1a}$, —$R^2$/—$R^3$, —$R^5$/—$R^{5a}$, and —$R^4$/—$R^{4a}$ are joined together with the atom to which they are attached to form a $C_{3-10}$ cycloalkyl, 3- to 10-membered heterocyclyl or a 8- to 11-membered heterobicyclyl;
optionally, one or more of the pairs —$R^1$/—$R^2$, —$R^1$/—$R^{5a}$, —$R^{1a}$/—$R^2$, —$R^{1a}$/—$R^3$, —$R^{1a}$/—$R^5$, —$R^{1a}$/—$R^{5a}$, —$R^2$/—$R^5$, —$R^2$/—$R^{5a}$, —$R^3$/—$R^5$, —$R^3$/—$R^{5a}$ are joined together with the atoms to which they are attached to form a ring —A—, where:
—A— is selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl;

wherein -$L^1$ is substituted with one to five moieties -$L^2$-Z, wherein the one to five hydrogens for substitutions are given by —$R^1$, —$R^{1a}$, —$R^2$, —$R^3$, —$R^{4a}$, —$R^5$, —$R^{5a}$, —$R^6$ or —$R^7$ of -$L^1$, wherein:
-$L^2$- is a single chemical bond or a spacer moiety; and
-Z is a carrier moiety.

2. The conjugate or a pharmaceutically acceptable salt thereof of claim 1;
wherein D is a small molecule biologically active moiety, oligonucleotide moiety, peptide nucleic acid moiety, peptide moiety, or protein moiety.

3. The conjugate or pharmaceutically acceptable salt thereof of claim 1;
wherein -Z is a $C_{8-18}$ alkyl group or a polymer with a molecular weight of at least 0.5 kDa.

4. The conjugate or pharmaceutically acceptable salt thereof of claim 1;
wherein -Z is selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly ethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

5. The conjugate or pharmaceutically acceptable salt thereof of claim 1;
wherein -Z is a protein.

6. The conjugate or pharmaceutically acceptable salt thereof of claim 1;
wherein -Z is a PEG-based polymer comprising at least 10% PEG.

7. The conjugate or pharmaceutically acceptable salt thereof of claim 1;
wherein -Z is a water-soluble polymer.

8. The conjugate or pharmaceutically acceptable salt thereof of claim 1;
wherein -Z is a PEG-based hydrogel comprising at least 10% PEG.

9. The conjugate or pharmaceutically acceptable salt thereof of claim 1;
wherein:
-$L^2$- is selected from the group consisting of —T—, —C(O)O—, —O—, —C(O)—, —C(O)N($R^{y1}$)—, —S(O)$_2$N($R^{y1}$)—, —S(O)N($R^{y1}$)—, —S(O)$_2$—, —S(O)—, —N($R^{y1}$)S(O)$_2$N($R^{y1a}$)—, —S—, $N(R^{y1})$—, —$OC(OR^{y1})(R^{y1a})$—, —$N(R^{y1})C(O)N(R^{y1a})$—, —$OC(O)N(R^{y1})$—, $C_{1-50}$ alkyl, $C_{2-50}$ alkenyl, and $C_{2-50}$ alkynyl, wherein:
- —T—, $C_{1-50}$ alkyl, $C_{2-50}$ alkenyl, and $C_{2-50}$ alkynyl are optionally substituted with one or more —$R^{y2}$, which are the same or different; and
- $C_{1-50}$ alkyl, $C_{2-50}$ alkenyl, and $C_{2-50}$ alkynyl are optionally interrupted by one or more groups selected from the group consisting of —T—, —C(O)O—, —O—, —C(O)—, —C(O)N($R^{y3}$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—, —OC(OR$^{y3}$)(R$^{y3a}$)—, —N($R^{y3}$)C(O)N($R^{y3a}$)—, and OC(O)N($R^{y3}$)—;

$R^{y4}$ and $R^{y1a}$ are independently of each other selected from the group consisting of —H, —T, $C_{1-50}$ alkyl, $C_{2-50}$ alkenyl, and $C_{2-50}$ alkynyl, wherein:
- —T, $C_{1-50}$ alkyl, $C_{2-50}$ alkenyl, and $C_{2-50}$ alkynyl are optionally substituted with one or more —$R^{y2}$, which are the same or different; and
- $C_{1-50}$ alkyl, $C_{2-50}$ alkenyl, and $C_{2-50}$ alkynyl are optionally interrupted by one or more groups selected from the group consisting of —T—, —C(O)O—, —O—, —C(O)—, —C(O)N($R^{y4}$)—, —S(O)$_2$N($R^{y4}$)—, —S(O)N($R^{y4}$)—, —S(O)$_2$—, —S(O)—, —N($R^{y4}$)S(O)$_2$N($R^{y4a}$)—, —S—, —N($R^{y4}$)—, —OC(OR$^{y4}$)(R$^{y4a}$)—, —N(R$_{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl, wherein:
- each T is independently optionally substituted with one or more —$R^{y2}$, which are the same or different;

each $R^{y2}$ is independently selected from the group consisting of halogen, —CN, oxo (=O), —COOR$^{y5}$, —OR$^{y5}$, —C(O)R$^{y5}$, —C(O)N(R$^{y5}$R$^{y5a}$), —S(O)$_2$N(R$^{y5}$R$^{y5a}$), —S(O)N(R$^{y5}$R$^{y5a}$), —S(O)$_2$R$^{y5}$, —S(O)R$^{y5}$, —N(R$^{y5}$)S(O)$_2$N(R$^{y5a}$R$^{y5b}$), —SR$^{y5}$, —N(R$^{y5}$R$^{y5a}$), —NO$_2$, —OC(O)R$^{y5}$, —N(R$^{y5}$)C(O)R$^{y5a}$, —N(R$^{y5}$)S(O)$_2$R$^{y5a}$, —N(R$^{y5}$)S(O)R$^{y5a}$, —N(R$^{y5}$)C(O)OR$^{y5a}$, —N(R$^{y5}$)C(O)N(R$^{y5a}$R$^{y5b}$), —OC(O)N(R$^{y5}$R$^{y5a}$), and $C_{1-6}$ alkyl, wherein:
- $C_{1-6}$ alkyl is optionally substituted with one or more halogen, which are the same or different; and
- each —R$^{y3}$, —R$^{y3a}$, —R$^{y4}$, —R$^{y4a}$, —R$^{y5}$, —R$^{y5a}$, and —R$^{y5b}$ is independently selected from the group consisting of —H and $C_{1-6}$ alkyl, wherein:
- $C_{1-6}$ alkyl is optionally substituted with one or more halogen, which are the same or different.

10. The conjugate or pharmaceutically acceptable salt thereof of claim 1;
wherein one hydrogen atom given by —R$^1$, —R$^{1a}$, —R$^2$, —R$^3$, —R$^{4a}$, —R$^5$, —R$^{5a}$, —R$^6$ or —R$^7$ is replaced by one moiety -L$^2$-Z.

11. The conjugate or pharmaceutically acceptable salt thereof of claim 1;
wherein —R$^{4a}$ is —H which is substituted with -L$^2$-Z.

12. The conjugate or pharmaceutically acceptable salt thereof of claim 1;
wherein —R$^1$, —R$^{1a}$, —R$^2$, —R$^3$, —R$^{4a}$, —R$^5$ and —R$^{5a}$ are independently of each other selected from the group consisting of —H, $C_{1-6}$ alkyl, $C_{2-6}$ alkenyl, and $C_{2-6}$ alkynyl.

13. The conjugate or pharmaceutically acceptable salt thereof of claim 1;
wherein —X$^1$— of is —C(R$^5$R$^{5a}$)—.

14. The conjugate or pharmaceutically acceptable salt thereof of claim 1;
wherein =Y$^1$ is =O.

15. A pharmaceutical composition comprising:
the conjugate or pharmaceutically acceptable salt thereof of claim 1; and
one or more excipients.

16. A method comprising:
administering the conjugate or pharmaceutically acceptable salt thereof of claim 1 as a medicament.

* * * * *

UNITED STATES PATENT AND TRADEMARK OFFICE
CERTIFICATE OF CORRECTION

PATENT NO.       : 11,298,427 B2
APPLICATION NO.  : 15/577606
DATED            : April 12, 2022
INVENTOR(S)      : Harald Rau et al.

Page 1 of 2

It is certified that error appears in the above-identified patent and that said Letters Patent is hereby corrected as shown below:

In the Specification

In Column 30, Line 28, "-R$^a$" should be corrected to read "-R$^{1a}$".

In Column 53, within the formula (e-iv) the interrupted line should be corrected to read:

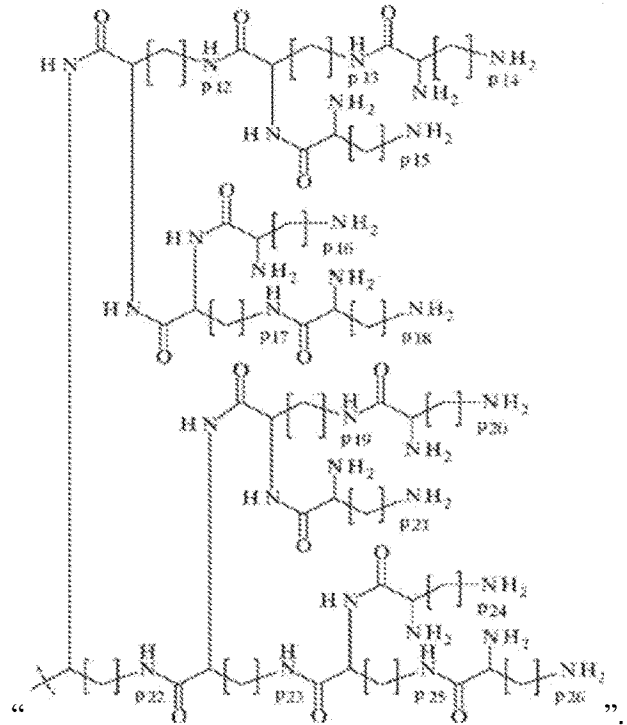

In the Claims

Signed and Sealed this
Eighteenth Day of October, 2022

Katherine Kelly Vidal
*Director of the United States Patent and Trademark Office*

CERTIFICATE OF CORRECTION (continued)
U.S. Pat. No. 11,298,427 B2

In Claim 1, Column 99, Line 20, the variables within the expression should be "-$R^1$, -$R^{1a}$, -$R^2$, -$R^3$, -$R^{4a}$, -$R^5$,".

In Claim 1, Column 99, Lines 58 and 59, should read "optionally, one or more of the pairs -$R^1$/-$R^2$, -$R^1$/-$R^3$, -$R^1$/-$R^5$, -$R^1$/-$R^{5a}$, -$R^{1a}$/-$R^2$, -$R^{1a}$/$R^3$,-$R^{1a}$/-".

In Claim 9, Column 101, Line 12, "-N($R^{y3}$)S(O)$_2$N($R^{y3}$a)-" should read "-N($R^{y3}$)S(O)$_2$N($R^{y3a}$)".

In Claim 9, Column 101, Line 15, should read "-OC(O)N($R^{y3}$)".

In Claim 9, Column 101, Line 16, "$R^{y4}$" should be corrected to read "$R^{y1}$".

In Claim 9, Column 101, Line 28, "-N($R_{y4}$)C" should be corrected to read "-N($R^{y4}$)C".